United States Patent
Novobrantseva et al.

(10) Patent No.: US 10,983,110 B2
(45) Date of Patent: Apr. 20, 2021

(54) ASSAYS FOR THE DETECTION OF AAV NEUTRALIZING ANTIBODIES

(71) Applicant: Voyager Therapeutics, Inc., Cambridge, MA (US)

(72) Inventors: Tatiana I. Novobrantseva, Wellesley, MA (US); Dinah Wen-Yee Sah, Hopkinton, MA (US)

(73) Assignee: VOYAGER THERAPEUTICS, INC., Cambridge, MA (US)

(*) Notice: Subject to any disclaimer, the term of this patent is extended or adjusted under 35 U.S.C. 154(b) by 14 days.

(21) Appl. No.: 15/779,841

(22) PCT Filed: Dec. 2, 2016

(86) PCT No.: PCT/US2016/064616
§ 371 (c)(1),
(2) Date: May 29, 2018

(87) PCT Pub. No.: WO2017/096162
PCT Pub. Date: Jun. 8, 2017

(65) Prior Publication Data
US 2018/0356394 A1 Dec. 13, 2018

Related U.S. Application Data

(60) Provisional application No. 62/417,631, filed on Nov. 4, 2016, provisional application No. 62/262,174, filed on Dec. 2, 2015.

(51) Int. Cl.
*C12Q 1/70* (2006.01)
*C12N 15/86* (2006.01)
*G01N 33/50* (2006.01)
*C07K 16/08* (2006.01)

(52) U.S. Cl.
CPC ........ *G01N 33/502* (2013.01); *C07K 16/081* (2013.01); *C12N 15/86* (2013.01); *C12Q 1/70* (2013.01); *C07K 2319/60* (2013.01); *C12N 2750/14143* (2013.01); *G01N 2469/20* (2013.01); *G01N 2500/10* (2013.01)

(58) Field of Classification Search
None
See application file for complete search history.

(56) References Cited

U.S. PATENT DOCUMENTS

| | | | |
|---|---|---|---|
| 1,004,109 A | 9/1911 | Timmerman |
| 5,474,935 A | 12/1995 | Chatterjee |
| 5,587,308 A | 12/1996 | Carter |
| 5,652,224 A | 7/1997 | Wilson |
| 5,658,785 A | 8/1997 | Johnson |
| 5,693,531 A | 12/1997 | Chiorini |
| 5,856,152 A | 1/1999 | Wilson |
| 5,858,775 A | 1/1999 | Johnson |
| 5,866,552 A | 2/1999 | Wilson |
| 5,866,696 A | 2/1999 | Carter |
| 5,871,982 A | 2/1999 | Wilson |
| 5,952,221 A | 9/1999 | Kurtzman |
| 5,962,313 A | 10/1999 | Podsakoff |
| 5,989,540 A | 11/1999 | Carter |
| 6,083,716 A | 7/2000 | Wilson |
| 6,174,527 B1 | 1/2001 | Wilson |
| 6,200,560 B1 | 3/2001 | Couto |
| 6,251,677 B1 | 6/2001 | Wilson |
| 6,387,368 B1 | 5/2002 | Wilson |
| 6,399,385 B1 | 6/2002 | Croyle |
| 6,416,992 B1 | 7/2002 | Mejza |
| 6,436,392 B1 | 8/2002 | Engelhardt |
| 6,468,771 B1 | 10/2002 | Einerhand |
| 6,509,150 B1 | 1/2003 | Salvetti |
| 6,521,426 B1 | 2/2003 | Ciliberto |
| 6,582,692 B1 | 6/2003 | Podsakoff |
| 6,642,051 B1 | 11/2003 | Lynch |
| 6,670,176 B1 | 12/2003 | Samulski |
| 6,710,036 B2 | 3/2004 | Kurtzman |
| 6,753,419 B1 | 6/2004 | Toniatti |
| 6,759,237 B1 | 7/2004 | Wilson |
| 6,846,665 B1 | 1/2005 | Horer |
| 6,855,314 B1 | 2/2005 | Chiorini |
| 6,887,463 B2 | 5/2005 | Wilson |
| 6,897,045 B2 | 5/2005 | Engelhardt |
| 6,984,517 B1 | 1/2006 | Chiorini |
| 7,056,502 B2 | 6/2006 | Hildinger |
| 7,070,998 B2 | 7/2006 | Johnson |
| 7,105,345 B2 | 9/2006 | Wilson |

(Continued)

FOREIGN PATENT DOCUMENTS

| | | |
|---|---|---|
| EP | 1046711 | 10/2000 |
| EP | 1078096 | 2/2001 |

(Continued)

OTHER PUBLICATIONS

Tomar et al., Use of adeno-associated viral vector for delivery of small interfering RNA, 2003, Oncogene, vol. 22, pp. 5712-5715.*
Pleticha et al., High cerebrospinal fluid levels of interleukin-10 attained by AAV in dogs, 2015, Gene Therapy, vol. 22, pp. 202-208.*
Carter BJ. Adeno-associated virus and the development of adeno-associated virus vectors: a historical perspective. Mol Ther. Dec. 2004;10(6):981-9.
G. S. Banker, Modern Pharmaceutics, Drugs and the Pharmaceutical Sciences, v. 72, Marcel Dekker, New York, Inc., 1996.
Grimm D, et al. Progress in adeno-associated virus type 2 vector production: promises and prospects for clinical use. Hum Gene Ther. Oct. 10, 1999;10(15):2445-50.
Grimson A, et al. MicroRNA targeting specificity in mammals: determinants beyond seed pairing. Mol Cell. Jul. 6, 2007;27(1):91-105.
Hastie E, et al. Adeno-Associated Virus at 50: A Golden Anniversary of Discovery, Research, and Gene Therapy Success—A Personal Perspective. Hum Gene Ther. May 2015, 26(5):257-65.

(Continued)

*Primary Examiner* — Benjamin P Blumel
(74) *Attorney, Agent, or Firm* — DT Ward, PC; Donna T. Ward; Mark J. Hanson

(57) ABSTRACT

The present invention relates to improved methods and assays for the detection of AAV neutralizing antibodies in sera. The present invention provides safe, sensitive and high throughput neutralization assays for antibody detection.

22 Claims, 5 Drawing Sheets

(56) References Cited

U.S. PATENT DOCUMENTS

| | | |
|---|---|---|
| 7,125,705 B2 | 10/2006 | Colosi |
| 7,169,612 B2 | 1/2007 | Kostenis |
| 7,186,552 B2 | 3/2007 | Wilson |
| 7,198,951 B2 | 4/2007 | Gao |
| 7,235,393 B2 | 6/2007 | Gao |
| 7,241,447 B1 | 7/2007 | Engelhardt |
| 7,247,472 B2 | 7/2007 | Wilson |
| 7,271,002 B2 | 9/2007 | Kotin |
| 7,282,199 B2 | 10/2007 | Gao |
| 7,306,794 B2 | 12/2007 | Wilson |
| 7,344,872 B2 | 3/2008 | Gao |
| 7,479,554 B2 | 1/2009 | Chiorini |
| 7,638,120 B2 | 12/2009 | Liu |
| 7,662,627 B2 | 2/2010 | Johnson |
| 7,790,449 B2 | 9/2010 | Gao |
| 7,803,622 B2 | 9/2010 | Engelhardt |
| 7,838,277 B2 | 11/2010 | Gao |
| 7,906,111 B2 | 3/2011 | Wilson |
| 8,105,574 B2 | 1/2012 | Wilson |
| 8,231,880 B2 | 7/2012 | Roy |
| 8,241,622 B2 | 8/2012 | Englehardt |
| 8,273,344 B2 | 9/2012 | Wang |
| 8,318,480 B2 | 11/2012 | Gao |
| 8,318,687 B2 | 11/2012 | Tabira |
| 8,394,386 B2 | 3/2013 | Wilson |
| 8,470,310 B2 | 6/2013 | Roy |
| 8,524,219 B2 | 9/2013 | Roy |
| 8,603,459 B2 | 12/2013 | Wilson |
| 8,637,255 B2 | 1/2014 | Wilson |
| 8,697,665 B2 | 4/2014 | Rom |
| 8,846,389 B2 | 9/2014 | Chiorini |
| 8,906,387 B2 | 12/2014 | Kay |
| 8,906,675 B2 | 12/2014 | Gao |
| 8,927,514 B2 | 1/2015 | Chatterjee |
| 8,962,330 B2 | 2/2015 | Gao |
| 8,962,332 B2 | 2/2015 | Gao |
| 8,999,678 B2 | 4/2015 | Vandenberghe |
| 9,163,260 B2 | 10/2015 | Wilson |
| 9,217,155 B2 | 12/2015 | Gao |
| 9,260,724 B2 | 2/2016 | Bakker |
| 9,441,244 B2 | 9/2016 | Schaffer |
| 9,457,103 B2 | 10/2016 | Schaffer |
| 9,493,788 B2 | 11/2016 | Gao |
| 9,506,083 B2 | 11/2016 | Arbetman |
| 9,546,369 B2 | 1/2017 | Gao |
| 9,567,607 B2 | 2/2017 | Wilson |
| 9,585,971 B2 | 3/2017 | Deverman |
| 9,587,250 B2 | 3/2017 | Gao |
| 9,593,346 B2 | 3/2017 | Roy |
| 9,597,363 B2 | 3/2017 | Roy |
| 9,617,561 B2 | 4/2017 | Roy |
| 9,623,120 B2 | 4/2017 | Chatterjee |
| 9,670,507 B2 | 6/2017 | Xiao |
| 9,677,088 B2 | 6/2017 | Nakai |
| 9,677,089 B2 | 6/2017 | Gao |
| 2001/0006955 A1 | 7/2001 | Wilson |
| 2001/0049144 A1 | 12/2001 | Rivera |
| 2002/0037867 A1 | 3/2002 | Wilson |
| 2002/0131961 A1 | 9/2002 | Wilson |
| 2002/0136710 A1 | 9/2002 | Samulski |
| 2003/0013189 A1 | 1/2003 | Wilson |
| 2003/0100115 A1 | 5/2003 | Raj |
| 2003/0138772 A1 | 7/2003 | Gao |
| 2004/0043490 A1 | 3/2004 | Shimada |
| 2004/0057931 A1 | 3/2004 | Wilson |
| 2004/0057932 A1 | 3/2004 | Wilson |
| 2004/0136963 A1 | 7/2004 | Wilson |
| 2004/0171807 A1 | 9/2004 | Gao |
| 2006/0204479 A1 | 9/2006 | Wilson |
| 2008/0008684 A1 | 1/2008 | Wilson |
| 2008/0050343 A1 | 2/2008 | Wilson |
| 2008/0050345 A1 | 2/2008 | Wilson |
| 2008/0075737 A1 | 3/2008 | Gao |
| 2009/0215871 A1 | 8/2009 | Wilson |
| 2009/0317417 A1 | 12/2009 | Vandenberghe |
| 2010/0247490 A1 | 9/2010 | Roy |
| 2010/0278791 A1 | 11/2010 | Wilson |
| 2011/0223135 A1 | 9/2011 | Roy |
| 2012/0046349 A1 | 2/2012 | Bell |
| 2012/0058102 A1 | 3/2012 | Wilson |
| 2012/0093853 A1 | 4/2012 | Wilson |
| 2012/0137379 A1 | 5/2012 | Gao |
| 2013/0045186 A1 | 2/2013 | Gao |
| 2013/0101558 A1 | 4/2013 | Gao |
| 2013/0195801 A1 | 8/2013 | Gao |
| 2013/0296532 A1 | 11/2013 | Hermens |
| 2013/0323226 A1 | 12/2013 | Wilson |
| 2014/0031418 A1 | 1/2014 | Wilson |
| 2014/0044680 A1 | 2/2014 | Roy |
| 2014/0336245 A1 | 11/2014 | Mingozzi |
| 2014/0341852 A1 | 11/2014 | Srivastava |
| 2015/0023924 A1 | 1/2015 | High |
| 2015/0065562 A1 | 3/2015 | Yazicioglu |
| 2015/0159173 A1 | 6/2015 | Vandenberghe |
| 2015/0315610 A1 | 11/2015 | Nishie |
| 2015/0374803 A1 | 12/2015 | Wolfe |
| 2016/0271192 A1 | 9/2016 | Roy |
| 2016/0289275 A1 | 10/2016 | Chiorini |
| 2016/0333372 A1 | 11/2016 | Srivastava |
| 2016/0340393 A1 | 11/2016 | Schaffer |
| 2017/0000904 A1 | 1/2017 | Wilson |
| 2017/0028082 A1 | 2/2017 | Wilson |
| 2017/0073703 A1 | 3/2017 | Chatterjee |
| 2017/0088858 A1 | 3/2017 | Gao |
| 2017/0128594 A1 | 5/2017 | Wright |
| 2017/0159027 A1 | 6/2017 | Wilson |
| 2018/0280497 A1 | 10/2018 | Seder |
| 2018/0280540 A1 | 10/2018 | Arbetman |
| 2018/0289757 A1 | 10/2018 | Schaffer |
| 2019/0048041 A1 | 2/2019 | Asokan |

FOREIGN PATENT DOCUMENTS

| | | |
|---|---|---|
| EP | 1164195 | 12/2001 |
| EP | 1218035 | 7/2002 |
| EP | 1240345 | 9/2002 |
| EP | 1279740 | 1/2003 |
| EP | 1453547 | 9/2004 |
| EP | 1696036 | 8/2006 |
| EP | 1847614 | 10/2007 |
| EP | 1849872 | 10/2007 |
| EP | 1944043 | 7/2008 |
| EP | 2007795 | 12/2008 |
| EP | 2198016 | 6/2010 |
| EP | 2220241 | 8/2010 |
| EP | 2220242 | 8/2010 |
| EP | 2292779 | 3/2011 |
| EP | 2292780 | 3/2011 |
| EP | 2325298 | 5/2011 |
| EP | 2359866 | 8/2011 |
| EP | 2383346 | 11/2011 |
| EP | 2524037 | 11/2012 |
| EP | 2660325 | 11/2013 |
| EP | 2814958 | 12/2014 |
| EP | 3209311 | 8/2017 |
| EP | 3221453 | 9/2017 |
| EP | 3235827 | 10/2017 |
| WO | 1993009239 | 5/1993 |
| WO | 1995034670 | 12/1995 |
| WO | 1996023810 | 8/1996 |
| WO | 1996030540 | 10/1996 |
| WO | 1999027110 | 6/1999 |
| WO | 1999058700 | 11/1999 |
| WO | 1999061595 | 12/1999 |
| WO | 1999060146 | 5/2000 |
| WO | 2000066780 | 11/2000 |
| WO | 2000075353 | 12/2000 |
| WO | 2001014539 | 3/2001 |
| WO | 2001025465 | 4/2001 |
| WO | 2001032711 | 5/2001 |
| WO | 2001036623 | 5/2001 |
| WO | 2001042444 | 6/2001 |
| WO | 2001068888 | 9/2001 |
| WO | 2001096587 | 12/2001 |

(56) References Cited

FOREIGN PATENT DOCUMENTS

| | | |
|---|---|---|
| WO | 2002012525 | 2/2002 |
| WO | 2002020748 | 3/2002 |
| WO | 2002070719 | 9/2002 |
| WO | 2002071843 | 9/2002 |
| WO | 2003010320 | 2/2003 |
| WO | 2003024502 | 3/2003 |
| WO | 2003042397 | 5/2003 |
| WO | 2003052051 | 6/2003 |
| WO | 2003087382 | 10/2003 |
| WO | 2003087383 | 10/2003 |
| WO | 2004044003 | 5/2004 |
| WO | 2004083441 | 9/2004 |
| WO | 2004108922 | 12/2004 |
| WO | 2004111248 | 12/2004 |
| WO | 2005005610 | 1/2005 |
| WO | 2005012537 | 2/2005 |
| WO | 2005111220 | 11/2005 |
| WO | 2006102072 | 9/2006 |
| WO | 2007130519 | 11/2007 |
| WO | 2009073104 | 6/2009 |
| WO | 2007148971 | 7/2009 |
| WO | 2009134681 | 11/2009 |
| WO | 2011038187 | 3/2011 |
| WO | 2011054976 | 5/2011 |
| WO | 2011122950 | 10/2011 |
| WO | 2010109053 | 11/2011 |
| WO | 2013078199 | 5/2013 |
| WO | 2013164793 | 11/2013 |
| WO | 2013170078 | 11/2013 |
| WO | 2014168953 | 10/2014 |
| WO | 2014194132 | 12/2014 |
| WO | 2014204726 | 12/2014 |
| WO | 2015006743 | 1/2015 |
| WO | 2015054653 | 4/2015 |
| WO | 2015060722 | 4/2015 |
| WO | 2015121501 | 8/2015 |
| WO | 2015164758 | 10/2015 |
| WO | 2015164786 | 10/2015 |
| WO | 2015127128 | 11/2015 |
| WO | 2016065001 | 4/2016 |
| WO | 2016073693 | 5/2016 |
| WO | 2016081811 | 5/2016 |
| WO | 2016137949 | 9/2016 |
| WO | 2016154055 | 9/2016 |
| WO | 2016154344 | 9/2016 |
| WO | 2016176212 | 11/2016 |
| WO | 2016183297 | 11/2016 |
| WO | 2017019994 | 2/2017 |
| WO | 2017058892 | 4/2017 |
| WO | 2017075335 | 5/2017 |
| WO | 2017106236 | 6/2017 |
| WO | 2017143100 | 8/2017 |
| WO | 2017147477 | 8/2017 |
| WO | 2017180854 | 10/2017 |
| WO | 2017192699 | 11/2017 |
| WO | 2017192750 | 11/2017 |
| WO | 2018212842 A1 | 11/2018 |
| WO | 2019018439 A1 | 1/2019 |

OTHER PUBLICATIONS

Aydemir F, et al. Mutants at the 2-fold interface of AAV2 structural proteins suggest a role in viral transcription for AAV capsids. J Virol. Jul. 2016;90(16):7196-204.
Bantel-Schaal U, et al. Human adeno-associated virus type 5 is only distantly related to other known primate helper-dependent parvoviruses. J Virol. Feb. 1999;73(2):939-47.
Berry GE, et al. Cellular transduction mechanisms of adeno-associated viral vectors. Curr Opin Virol. Dec. 2016;21:54-60.
Chiorini JA, et al. Adeno-associated virus (AAV) type 5 Rep protein cleaves a unique terminal resolution site compared with other AAV serotypes. J Virol. May 1999;73(5):4293-8.
Chiorini JA, et al. Cloning and characterization of adeno-associated virus type 5. J Virol. Feb. 1999;73(2):1309-19.
Chiorini JA, et al. Cloning of adeno-associated virus type 4 (AAV4) and generation of recombinant AAV4 particles. J Virol. Sep. 1997;71(9):6823-33.
Earley LF, et al. Adeno-Associated Virus Assembly-Activating Protein Is Not an Essential Requirement for Capsid Assembly of AAV Serotypes 4, 5 and 11. J Virol. Jan. 2017;91(3):pii:e0198-16.
Ding C, et al., Biochemical Characterization of Junonia Coenia Densovirus Nonstructural Protein NS-1. J. Virol., 76(1):338-345 2002.
Bell P, et al. Effects of self-complementarity, codon optimization, transgene, and dose on liver transduction with AAV8. Hum Gene Ther Methods. Dec. 2016;27(6):228-237.
Heim et al., Wavelength mutations and posttranslational autoxidation of green fluorescent protein. Proc. Natl. Acad. Sci. USA (1994).
Hastie E, et al. Recombinant adeno-associated virus vectors in the treatment of rare diseases. Expert Opin Orphan Drugs. 2015;3(6):675-689.
Greig JA, et al. Intramuscular administration of AAV overcomes pre-existing neutralizing antibodies in rhesus macaques. Vaccine. Dec. 2016;34(50):6323-6329.
Maniatis T. et al.,Molecular Cloning. CSH Laboratory, NY, N.Y. (1982).
Merten OW, et al. Viral vectors for gene therapy and gene modification approaches. Biochem Eng J. Apr. 2016;108:98-115.
Muzyczka N, et al. AAV's Golden Jubilee. Mol Ther. May 2015;23(5):807-8.
Philiport, et al. Liposomes as tools in Basic Research and Industry. CRC Press, Ann Arbor, Mich. (1995).
Kailasan S, et al. Parvovirus Family Conundrum: What makes a killer? Annu Rev Virol. Nov. 2015;2(1):425-50.
Rutledge EA, et al. Infectious clones and vectors derived from adeno-associated virus (AAV) serotypes other than AAV type 2. J Virol. Jan. 1998;72(1):309-19.
Pillay S, et al. An essential receptor for adeno-associated virus infection. Nature. Nov. 17, 2016;539(7629):456.
Platt MP, et al. Embryonic disruption of the candidate dyslexia susceptibility gene homolog Kiaa0319-like results in neuronal migration disorders. Neuroscience. Sep. 17, 2013;248:585-93.
Poon MW, et al. Distribution of Kiaa0319-like immunoreactivity in the adult mouse brain—a novel protein encoded by the putative dyslexia susceptibility gene KIAA0319-like. Histol Histopathol. Aug. 2011;26(8):953-63.
Poon MW, et al. Dyslexia-associated kiaa0319-like protein interacts with axon guidance receptor nogo receptor 1. Cell Mol Neurobiol. Jan. 2011;31(1):27-35.
Heim R, et al. Engineering green fluorescent protein for improved brightness, longer wavelengths and fluorescence resonance energy transfer. Curr Biol. Feb. 1, 1996;6(2):178-82.
Heim R,et al. Improved green fluorescence Nature 373, 663-664 (Feb. 23, 1995); doi:10.1038/373663b0.
Nygaard S, et al. A universal system to select gene-modified hepatocytes in vivo. Sci Transl Med. Jun. 2016;8(342):342ra79.
Smith RH, et al. Germline viral "fossils" guide in silico reconstruction of a mid-Cenozoic era marsupial adeno-associated virus. Sci Rep. Jul. 2016;6:28965.
Li L, et al. Production and characterization of novel recombinant adeno-associated virus replicative-form genomes: a eukaryotic source of DNA for gene transfer. PLoS One. Aug. 1, 2013;8(8):e69879. doi: 10.1371/journal.pone.0069879. Print 2013.
O'Reilly DR, et al. Baculovirus expression vectors: a laboratory manual. Oxford University Press, 1994.
Oliva B, et al. An automated classification of the structure of protein loops. J Mol Biol. Mar. 7, 1997;266(4):814-30.
Hinderer C, et al. Neonatal Systemic AAV Induces Tolerance to CNS Gene Therapy in MPS I Dogs and Nonhuman Primates. Mol Ther. Aug. 2015, 23(8)1298-307.
Hudry EM, et al. Exosome-associated AAV vector as a robust and convenient neuroscience tool. Gene Ther. Apr. 2016;23(4):380-92.
Srivastava A. Adeno-Associated Virus: The Naturally Occurring Virus Versus the Recombinant Vector. Hum Gene Ther. Jan. 2016;27(1):1-6.
Thorne B, et al. Gene Therapy. Adv Biochem Eng Biotechnol. Mar. 14, 2017 Epub ahead of print.

(56) References Cited

OTHER PUBLICATIONS

Tratschin JD, et al. Adeno-associated virus vector for high-frequency integration, expression, and rescue of genes in mammalian cells. Mol Cell Biol. Nov. 1985;5(11):3251-60.
Srivastava A, et al. Nucleotide sequence and organization of the adeno-associated virus 2 genome. J Virol. Feb. 1983;45(2):555-64.
Summerford C, et al. AAVR: A multi-serotype receptor for AAV. Mol Ther. Apr. 2016;24(4):663-6.
Xie Q, et al. The atomic structure of adeno-associated virus (AAV-2), a vector for human gene therapy. Proc Natl Acad Sci U S A. Aug. 6, 2002;99(16):10405-10. Epub Jul. 22, 2002.
Wu P, et al. Mutational analysis of the adeno-associated virus type 2 (AAV2) capsid gene and construction of AAV2 vectors with altered tropism. J Virol. Sep. 2000;74(18):8635-47.
Yang C, et al. Sequential adeno-associated viral vector serotype 9-green fluorescent protein gene transfer causes massive inflammation and intense immune response in rat striatum. Hum Gene Ther. Jul. 2016;27(7):528-43.
Afione S, et al. Identification and Mutagenesis of the Adeno-Associated Virus 5 Sialic Acid Binding Region.J Virol. Feb. 2015, 89(3):1660-72.
Drouin LM, et al. Cryo-electron microscopy reconstruction and stability studies of Wild-Type and R432A Variant of AAV2 Reveals Capsid Structural Stability is a Major Factor in Genome Packaging. J Virol. Sep. 2016;90(19):8542-51.
Halder S, et al. Structure of neurotropic adeno-associated virus AAVrh.8. J Struct Biol. Oct. 2015;192(1):21-36.
Huang LY, et al. Characterization of the adeno-associated virus 1 and 6 sialic acid binding site. J Virol. May 2016;90(11):5219-30.
Mao Y, et al. Single point mutation in adeno-associated viral vectors—DJ capsid leads to improvement for gene delivery in vivo. BMC Biotechnol. Jan. 2016;16:1.
Marsic D et al. Altering Tropism of rAAV by Directed Evolution. Methods of Mol Biol. 2016;1382:151-73.
Tu MY, et al. Role of capsid proteins in parvoviruses infection. Virol J. Aug. 2015,4;12:114.
Zeng C, et al. Probing the Link between Genomic Cargo, Contact Mechanics and Nanoindentation in Recombinant Adeno-Associated Virus 2. J Phys Chem B. Mar. 2017;121(8):1843-1853.
Zinn E, et al. In Silico Reconstruction of the Viral Evolutionary Lineage Yields a Potent Gene Therapy Vector. Cell Rep. Aug. 2015, 12(6):1056-68.
Huang LY, et al. Characterization of the Adeno-Associated Virus 1 and 6 Sialic Acid Binding Site. J Virol. May 12, 2016;90(11):5219-30.
Ashley SN, et al. Alternative Start Sites Downstream of Nonsense Mutations Drive Antigen Presentation and Tolerance Induction to C-Terminal Epitopes. Epub ahead of print.
Calcedo R, et al. AAV natural infection induces broad cross-neutralizing antibody responses to multiple AAV serotypes in chimpanzees. Hum Gene Ther Clin Dev. Jun. 2016;27(2):79-82.
Calcedo R, et al. Induction of Immune Tolerance to Foreign Protein via Adeno-Associated Viral Vector Gene Transfer in Mid-Gestation Fetal Sheep. PLoS One. Jan. 2017;12(1):e0171132.
Calcedo R, et al. Pre-existing neutralizing antibodies to adeno-associated virus capsids in large animals other than monkeys may confound in vivo gene therapy studies. Hum Gene Ther Methods. Jun. 2015;26(3):103-5.
Corden A, et al. Neutralizing antibodies against adeno-associated viruses in Sjögren's patients: implications for gene therapy. Gene Ther. Apr. 2017;24(4):241-244.
Ertl HC, et al. The impact of AAV capsid-specific T cell responses on design and outcome of clinical gene transfer trials with recombinant AAV vectors—an evolving controversy. Hum Gene Ther. Apr. 2017;28(4):328-337.
Ferrand M, et al.Serotype-specific Binding Properties and Nanoparticle Characteristics Contribute to the Immunogenicity of rAAV1 Vectors. Mol Ther.Jun. 2015, 23(6):1022-33.
Gernoux G, et al. Regulatory and exhausted T cell responses to AAV capsid. Hum Gene Ther. Apr. 2017;28(4):338-349.
Greenberg B, et al. Prevalence of AAV1 neutralizing antibodies and consequences for a clinical trial of gene transfer for advanced heart failure. Gene Ther. Mar. 2016;23(3):313-9.
Greig JA, et al. Nonclinical Pharmacology/Toxicology Study of AAV8.TBG.mLDLR and AAV8.TBG.hLDLR in a Mouse Model of Homozygous Familial Hypercholesterolemia. Hum Gene Ther Clin Dev. Mar. 2017;28(1):28-38.
Greig JA, et al. Non-Clinical Study Examining AAV8.TBG.hLDLR Vector-Associated Toxicity in Chow-Fed Wild-Type and LDLR+/− Rhesus Macaques. Hum Gene Ther Clin Dev. Mar. 2017;28(1):39-50.
Jungmann A, et al. Cell-based measurement of neutralizing antibodies against adeno-associated virus (AAV). Methods Mol Biol. 2017;1521:109-126.
Meliani A, et al. Determination of Anti-Adeno-Associated Virus Vector Neutralizing Antibody Titer with an In Vitro Reporter System. Hum Gene Ther Methods.Apr. 2015, 26(2):45-53.
Rogers GL, et al. Unique Roles of TLR9-and MyD88-Dependent and -Independent Pathways in Adaptive Immune Responses to AAV-Mediated Gene Transfer. J Innate Immun.Jul. 2015, 7(3):302-14.
Rogers GL, et al. Plasmacytoid and conventional dendritic cells cooperate in cross-priming AAV capsid-specific CD8+ T cells. Blood. May 3, 2017. Epub ahead of print.
Thwaite R, et al. AAVrh. 10 immunogenicity in mice and humans. Relevance of antibody cross-reactivity in human gene therapy. Gene Ther. Feb. 2015;22(2):196-201.
Tseng YS, et al. Generation and characterization of anti-AAV8 and anti-AAV9 monoclonal antibodies. J Virol Methods. Oct. 2016;236:105-10.
Velazquez VM, et al. Effective Depletion of Pre-existing Anti-AAV Antibodies Requires Broad Immune Targeting. Mol Ther Methods Clin Dev. Jan. 25, 2017;4:159-168.
Wang G, et al. Safety and biodistribution assessment of sc-rAAV2. 5IL-1Ra administered via intra-articular injection in a mono-iodoacetate-induced osteoarthritis rat model. Mol Ther Methods Clin Dev. Jan. 2016;3:15052.
Wang M, et al. Prediction of adeno-associated virus neutralizing antibody activity for clinical application. Gene Ther. Dec. 2015;22(12):984-92.
Zygmunt D, et al. Comparison of serum rAAV serotype-specific antibodies in patients with Duchenne Muscular Dystrophy, Becker Muscular Dystrophy, Inclusion Body Myositis or GNE myopathy. Hum Gene Ther. Dec. 29, 2016 Epub ahead of print.
Tseng YS, et al. Adeno-Associated Virus Serotype 1 (AAV1)-and AAV5-Antibody Complex Structures Reveal Evolutionary Commonalities in Parvovirus Antigenic Reactivity. J Virol. Feb. 2015, 89(3):1794-808.
Samaranch L et al. Slow AAV2 Clearance from the Brain of Nonhuman Primates and Anti-capsid Immune Response. Gene Ther. Apr. 2016;23(4):393-8.
Ferla R, et al. Prevalence of anti-adeno-associated virus serotype 8 neutralizing antibodies and arylsulfatase B cross-reactive immunologic material in mucopolysaccharidosis VI patient candidates for a gene therapy trial. Hum Gene Ther. Mar. 2015;26(3):145-52.
Harrington EA, et al. Neutralizing Antibodies Against Adeno-Associated Viral Capsids in Patients with mut Methylmalonic Acidemia. Hum Gene Ther. May 2016;27(5):345-53.
Kotterman MA, et al. Antibody neutralization poses a barrier to intravitreal adeno-associated viral vector gene delivery to non-human primates. Gene Ther. Feb. 2015;22(2):116-26.
Tse LV, et al. Structure-guided evolution of antigenically distinct adeno-associated virus variants for immune evasion. Proc Natl Acad Sci U S A. May 30, 2017. Epub ahead of print.
Li CW, et al. Development of patient-specific AAV vectors after neutralizing antibody selection for enhanced muscle gene transfer. Mol Ther. Feb. 2016;24(1):53-65.
Kern A, et al. Identification of a Heparin-Binding Motif on Adeno-Associated Virus Type 2 Capsids. Journal of Virology. Oct. 2003;11072-11081.
Vandamme C, et al. Unraveling the complex story of immune responses to AAV vectors trial after trial. Hum Gene Ther. Aug. 23, 2017.

(56) References Cited

OTHER PUBLICATIONS

Fu H, et al. Differential prevalence of antibodies against adeno-associated virus in healthy children and patients with mucopolysaccharidosis III: perspective for AAV-mediated gene therapy. Human Gene Ther Clin Dev Sep. 19, 2017 Epub ahead of print.
Mingozzi F, et al. Overcoming the Host Immune Response to Adeno-Associated Virus Gene Delivery Vectors: The Race Between Clearance, Tolerance, Neutralization, and Escape. Annu Rev Virol Sep. 29, 2017;4(1):511-534.
Majowicz A, et al. Successful Repeated Hepatic Gene Delivery in Mice and Non-human Primates Achieved by Sequential Administration of AAV5ch and AAV1. Mol Ther. Jun. 5, 2017. Epub ahead of print.
Kim Y, et al. Mutagenic Analysis of an Adeno-Associated Virus Variant Capable of Simultaneously Promoting Immune Resistance and Robust Gene Delivery. Hum Gene Ther. Jun. 24, 2017. Epub ahead of print.
Pillay S, et al. AAV serotypes have distinctive interactions with domains of the cellular receptor AAVR. J Virol. Jul. 5, 2017. Epub ahead of print.
Grimm et al. Small but increasingly mightly—latest advances in AAV vector research, design and evolution. Hum Gene Ther. Nov. 2017 (Epub Aug. 23, 2017); 28(11):1075-1086.
Pillay S, et al. Host determinants of adeno-associated viral vector entry. Curr Opin Virol. Jun. 30, 2017;24:124-131. Epub ahead of print.
Ahmad M, et al. Engineered Expression of Broadly Neutralizing Antibodies Against Human Immunodeficiency Virus. Annu Rev Virol. Jun. 23, 2017. Epub ahead of print.
Morabito G, Giannelli SG, Ordazzo G, Bido S, Castoldi V, Indrigo M, Cabassi T, Cattaneo S, Luoni M, Cancellieri C, Sessa A, Bacigaluppi M, Taverna S, Leocani L, Lanciego JL, Broccoli V. Mol Ther. Dec. 6, 2017;25(12):2727-2742. Epub Aug. 10, 2017.
Matsuzaki Y, Konno A, Mochizuki R, Shinohara Y, Nitta K, Okada Y, Hirai H. Neurosci Lett. Nov. 23, 2017. [Epub ahead of print].
Dayton RD, et al. More expansive gene transfer to the rat CNS: AAV PHP.EB vector dose—response and comparison to AAV PHP.B. Gene Ther. Jul. 16, 2018 Epub ahead of print.
Naidoo J, et al. Extensive Transduction and Enhanced Spread of a Modified AAV2 Capsid in the Non-human Primate CNS. Mol Ther. Jul. 12, 2018 Epub ahead of print.
Giles AR, et al. Mapping an adeno-associated virus 9-specific neutralizing epitope to develop next-generation gene delivery vectors. J Virol. Aug. 8, 2018 Epub ahead of print.
Deverman BE, et al. Gene therapy for neurological disorders: progress and prospects. Nat Rev Drug Discov. Aug. 10, 2018 Epub ahead of print.
Van Lieshout LP, et al. A Novel Triple-Mutant AAV6 Capsid Induces Rapid and Potent Transgene Expression in the Muscle and Respiratory Tract of Mice. Mol Ther Meth Clin Dev Jun. 15, 2018.
Tordo J, et al. A novel adeno-associated virus capsid with enhanced neurotropism corrects a lysosomal transmembrane enzyme deficiency. Brain Jul. 1, 2018;141(7):2014-2031.
Hudrey E, et al. Efficient gene transfer to the central nervous system by single stranded Anc80L65. Mol Ther Meth Clin Dev. Jul. 15, 2018.
Perocheau D, et al. Age-related seroprevalence of antibodies against AAV-LK03 in a UK pPAULK NK, et al. Bioengineered Viral Platform for Intramuscular Passive Vaccine Delivery to Human Skeletal Muscle. Mol Ther Methods Clin Dev. Jul. 24, 2018;10:144-155.
Smith JK and Agbandje-Mckenna M. Creating an arsenal of Adeno-associated virus (AAV) gene delivery stealth vehicles. PLOS Pathogens. May 3;14(5);e1006929.
Fitzpatrick Z, et al. Influence of Pre-existing Anti-capsid Neutralizing and Binding Antibodies on AAV Vector Transduction. Mol Ther Methods Clin Dev Feb. 13, 2018;9:119-129.
Fu HY, et al. Differential prevalence of antibodies against adeno-associated virus in healthy children and patients with mucopolysaccharidosis III: perspective for AAV-mediated gene therapy. Hum Gene Ther Clin Dev 28(4): 187-196.
Tse LV, et al. Mapping and engineering function domains of the assembly-activating protein of adeno-associated viruses. J. Virol. Jun. 29, 2018;92(14).
Bennett AD, et al. AAV6 K531 serves a dual function in selective receptor and antibody ADK6 recognition. Virology. May 2018;518:369-376.
Ramsingh AI, et al. Sustained AAV9-mediated expression of a non-self protein in the CNS of non-human primates after immunomodulation. PLoS One. Jun. 6, 2018;13(6): e0198154.
Sun J, et al. An Observational Study from Long-Term AAV Re-administration in Two Hemophilia Dogs. Mol Ther Methods Clin Dev Aug. 4, 2018;10:257-267.
Gowanlock D, et al. A designer AAV variant permits efficient retrograde access to projection neurons. Neuron. (2016) Oct. 19;92(2):372-382.
International Search Report issued in corresponding PCT Application No. PCT/US2015/034799 dated Nov. 23, 2015.
Extended European Search Report issued in corresponding EP Application No. EP15807546 dated Oct. 26, 2017.
Muzyczka, et al. Custom adeno-associated virus capsids: the next generation of recombinant vectors with novel tropism. Hum Gene Ther. Apr. 2005;16(4):408-16.
Li, Wuping et al. Engineering and selection of shuffled AAV genomes: a new strategy for producing targeted biological nanoparticles. Mol Ther. Jul. 2008;16(7):1252-60.
Hauck, et al. Generation and characterization of chimeric recombinant AAV vectors. Mol Ther. Mar. 2003;7(3):419-25.
International Search Report issued in corresponding PCT Application No. PCT/US2016/064616 dated Apr. 28, 2017.
Mizukami et al. Adeno-associated virus type 2 binds to a 150-kilodalton cell membrane glycoprotein. Virology. Mar. 1, 1996;217(1):124-30.
Handa et al. Adeno-associated virus (AAV)-3-based vectors transduce haematopoietic cells not susceptible to transduction with AAV-2-based vectors. J Gen Virol. Aug. 2000; 81 (Pt 8):2077-84.
Kay M A et al: "Evidence for gene transfer and expression of Factor IX in haemophilia B patients treated with an AAV vector", Nature Genetics, Nature Publishing Group, New York, US, vol. 24, Mar. 1, 2000 (Mar. 1, 2000), pp. 257-261.
Supplementary European Search Report received in corresponding EP application No. 16871573 dated Jul. 8, 2019.
Mingozzi F, et al. Adeno-associated viral vectors at the frontier between tolerance and immunity. Front Immunol.Mar. 2015, 6:120.
Arruda VR, et al. Obstacles and future of gene therapy for hemophilia. Expert Opin Orphan Drugs. 2015;3(9):997-1010.
George LA, et al. Gene therapy for hemophilia: past, present and future. Semin Hematol. Jan. 2016;53(1):46-54.
Chew WL et al. A multifunctional AAV-CRISPR-Cas9 and its host response. Nat Methods. Oct. 2016;13(10):868-74.
Mendoza SD, et al. AAV-mediated delivery of optogenetic constructs to the macaque brain triggers humoral immune responses. J Neurophysiol. May 2017;117(5):2004-2013.
Calcedo et al., Worldwide Epidemiology of Neutralizing Antibodies to Adeno-Associated Viruses, J Infect Dis. Feb. 1, 2009;199(3):381-90.
Boutin et al., Prevalence of serum IgG and neutralizing factors against adeno-associated virus (AAV) types 1, 2, 5, 6, 8, and 9 in the healthy population: implications for gene therapy using AAV vectors. Hum Gene Ther. Jun. 2010;21(6):704-12.
Martino et al., The genome of self-complementary adeno-associated viral vectors increases Toll-like receptor 9-dependent innate immune responses in the liver. Blood. Jun. 16, 2011;117(24):6459-68.
Bartel et al., Enhancing the Clinical Potential of AAV Vectors by Capsid Engineering to Evade Pre-Existing Immunity. Front Microbiol. Oct. 4, 2011;2:204.
Long BR et al., The Impact of Pre-existing Immunity on the Non-clinical Pharmacodynamics of AAV5-Based Gene Therapy. Molec Ther Clin Dev. Apr. 11, 2019. Epub.

(56) References Cited

OTHER PUBLICATIONS

Kruzik A et al., Detection of Biologically Relevant Low-Titer Neutralizing Antibodies Against Adeno-Associated Virus Require Sensitive In Vitro Assays.Hum Gene Ther Methods. Mar. 29, 2019. [Epub ahead of print].

Giles, April R et al., Mapping an Adeno-associated Virus 9-Specific Neutralizing Epitope to Develop Next-Generation Gene Delivery Vectors. J Virol. Sep. 26, 2018;92(20). Print Oct. 15, 2018.

Barnes C, et al. Engineering the AAV capsid to evade immune responses.Curr Opin Biotechnol. Feb. 23, 2019;60:99-103.

Welles et al., Vectored delivery of anti-SIV envelope targeting mAb via AAV8 protects rhesus macaques from repeated limiting dose intrarectal swarm SIVsmE660 challenge.PLoS Pathog. Dec. 5, 2018;14(12):e1007395.

Chai Z et al., Optimization of Dexamethasone Administration for Maintaining Global Transduction Efficacy of Adeno-Associated Virus 9. Hum Gene Ther. Jan. 31, 2019. [Epub ahead of print].

Ellsworth JL et al., Low Seroprevalence of Neutralizing Antibodies Targeting Two Clade F AAV in Humans.Hum Gene Ther Clin Dev. Feb. 27, 2018.

Reichel FF et al., Humoral Immune Response After Intravitreal But Not After Subretinal AAV8 in Primates and Patients.Invest Ophthalmol Vis Sci. Apr. 1, 2018;59(5):1910-1915.

Gardner MR et al., In Anti-drug antibody responses impair prophylaxis mediated by AAV-delivered HIV-1 broadly neutralizing antibodies. Molecular Therapy. Jan. 12, 2019. In press.

Wang D, et al. Adeno-Associated Virus Neutralizing Antibodies in Large Animals and Their Impact on Brain Intraparenchymal Gene Transfer.Mol Ther Methods Clin Dev. Oct. 4, 2018;11:65-72.

Kuranda K, et al. Exposure to wild-type AAV drives distinct capsid immunity profiles in humans.J Clin Invest. Dec. 3, 2018;128(12):5267-5279.

Jose A, et al. High resolution structural characterization of a new AAV5 antibody epitope toward engineering antibody resistant recombinant gene delivery vectors.J Virol. Dec. 10, 2018;93(1).

Guo P, et al. Rapid AAV Neutralizing Antibody Determination with a Cell-Binding Assay.Molecular. Therapy Methods & Clinical Development. In press.

Ramachandran P, et al. Evaluation of dose and safety of AAV7m8 and AAV8BP2 in the non-human primate retina. Hum Gene Ther. Feb. 2017;28(2):154-167.

Kavita U., et al. Development of a Chemiluminescent ELISA Method for the Detection of Total Anti-Adeno Associated Virus Serotype 9 (AAV9) Antibodies. Hum Gene Ther Methods. Nov. 22, 2018. Epub ahead of print.

Calcedo R et al., Assessment of Humoral, Innate, and T-Cell Immune Responses to Adeno-Associated Virus Vectors. Hum Gene Ther Methods. Apr. 2018;29(2):86-95.

Fuchs et al., Liver-directed but not muscle-directed AAV-antibody gene transfer limits humoral immune responses in rhesus monkeys. Molecular Therapy Methods & Clinical Development. Nov. 25, 2019.

Orlowski et al., Successful Transduction with AAV Vectors After Selective Depletion of Anti-AAV Antibodies by Immunoadsorption. Mol Ther Meth Clin D. 2020.

Perez et al., Management of Neuroinflammatory Responses to AAV-Mediated Gene Therapies for Neurodegenerative Diseases. Brain Sci. Feb. 22, 2020;10(2).

Krotova et al., Modifiers of AAV-mediated gene expression in implication for serotype-universal neutralizing antibody assay. Human Gene Therapy. Jun. 4, 2020, pp. 1124-1131.

* cited by examiner

ASSAYS FOR THE DETECTION OF AAV NEUTRALIZING ANTIBODIES

CROSS REFERENCE TO RELATED APPLICATIONS

This application is a U.S. National Stage Application of International Patent Application No. PCT/US2016/064616, filed Dec. 2, 2016, which claims the benefit of U.S. Provisional Application No. 62/262,174 filed Dec. 2, 2015 and U.S. Provisional Application No. 62/417,631 filed Nov. 4, 2016, the contents of each of which are incorporated by reference herein in their entirety.

FIELD OF THE INVENTION

The present invention provides methods and assays for determining neutralizing antibodies to AAV capsids and/or AAV serotypes in sera, and uses thereof.

BACKGROUND OF THE INVENTION

Gene transfer vectors based on adeno-associated virus (AAV), i.e., AAV vectors/particles, have become favored vectors because of characteristics such as an ability to transduce different types of dividing and non-dividing cells of different tissues and the ability to establish stable, long-term transgene expression. Though adeno-associated virus (AAV) has not been associated with any human diseases, its presence can be detected in many human tissues. The infected individuals develop immune response to AAVs. In the past, a full spectrum of immune responses to AAV capsids and/or AAV serotypes has been assessed to include innate responses, neutralizing antibodies and cytotoxic T cell responses, in human populations. Roughly 70% of the human population has neutralizing antibody (NAb) titers to AAV2 serotype (Erles et al., *J. Med Virol.*, 1999, 59(3): 406-411; and Calcedo et al., *J. of Infectious Diseases*, 2009; 199: 381-390). Additional studies have also estimated the prevalence of NAbs to other AAV capsids, including AAV1, AAV6, AAV7, AAV8 and AAV9 (Calcedo et al., *J. of Infectious Diseases*, 2009, 199: 381-390; and Boutin et al., *Hum Gene Ther.*, 2010, 21(6): 704-712). In addition, evidence that NAbs to AAV2 can reduce transduction efficiency against other AAV capsids and/or AAV serotypes raises the concern for cross-reactivity of capsid specific or serotypic NAbs. In vitro NAb assays and cross administration of AAV vectors in animals demonstrated that several NAbs have strong cross reactivity to different AAV serotypes (Calcedo et al., *J. of Infectious Diseases*, 2009, 199: 381-390; and Harbison et al., *J. Gen Virol.*, 2012, 93(2): 347-355).

The pre-existing neutralizing antibody titers to AAV capsids and/or AAV serotypes and their cross-reactivity, or those induced by administration, have emerged as a concern and challenge for clinical applications of gene therapy and genetic vaccine mediated by AAV vectors. The pre-existing NAbs recognizing viral capsids could inhibit AAV entry and transgene delivery to the host cells, thereby preventing long-term therapy in humans. Determining the presence and cross-reactivity of neutralizing antibodies in a subject is critical for clinical applications of AAV vectors and the design of the serotypic capsids of AAV vectors for gene therapy and genetic vaccine.

Neutralizing antibodies and their cross-reactivity to different AAV capsids and/or AAV serotypes are typically evaluated in various types of viral neutralization assays or tests, which are modified immune assays based on antibody-antigen interaction. In general, these assays involve production of recombinant AAV vectors with the helper adenovirus (Adv). Adenovirus (Adv) is a human pathogenic virus which causes respiratory illnesses and other diseases. There are stringent safety requirements to perform viral neutralization assays in the laboratory, and potential risk of infection to the operators during the assays and tests. Therefore, these assays can hardly be considered appropriate as routine high-throughput tests, particularly in a clinical setting.

Thus, there is a continuing need for routine, safe and reliable methods for viral neutralization assays. The present invention provides a new neutralization assay for determining neutralizing antibodies to specific AAV capsids and/or AAV serotypes and their cross reactivity to different AAV capsids and/or serotypes, without the helper Adv.

SUMMARY OF THE INVENTION

Currently available methods for determining pre-existing neutralizing antibodies in a patient prior to receiving AAV mediated gene therapy are relatively insensitive, do not usually have a large range of detection, and may raise potential safety concerns in the laboratory. Therefore, an object of the present invention is an assay/method of assessing neutralizing antibodies in a patient in a regular laboratory setting without involving pathogenic adenoviruses.

In some embodiments, the assays of the present invention may comprise evaluating AAV neutralizing antibody mediated blockage of AAV entry to AAV permissive cells after exposure of the AAV permissive cells to an AAV vector mixed with the serum sample. In this aspect, no adenovirus and/or its components are used for the present assays.

In some embodiments, the present assays determine AAV infectivity by measuring positively transduced cells, after exposure to the test sample containing AAV neutralizing antibodies, by measuring positively transduced cells. In this aspect, the transduced cells may be detected without cell lysis process. Additionally, the level of expression on a single cell level may be detected in order to monitor both the intensity of the signal in each cell versus the population, as well as to continue to monitor the percentage (%) of the cells expressing the transgene. This dual analysis can significantly enhance the quantitative features of the assay.

In some embodiments, the assays of the present invention may be used to pre-screen a patient prior to receiving an AAV vector mediated gene therapy; to adjust repeat dose of a gene therapy; and/or to design AAV vector using serotypic capsids and variants thereof.

In one aspect, the present invention provides a method of detecting AAV neutralizing antibodies in a serum sample by evaluating AAV neutralizing antibody mediated blockage of AAV entry into AAV permissive cells after exposure to a serum sample containing an AAV vector.

The serum sample used for the method of the present invention may be collected from a patient in need of AAV mediated gene therapy, a patient after a dose of AAV gene therapy or a subject suspected of exposure to AAV or a composition based on AAV. The serum sample may then be mixed with an AAV vector. In one aspect, the AAV vector may be fluorescently tagged, such as with GFP or any other fluorescent protein. The serum sample and AAV mixture may then contact AAV permissive cells, the transduced cells may be measured for fluorescent signal (e.g., GFP signal) using any method known in the art such as, but not limited to, flow cytometry. In order to determine neutralizing antibody response, signal positive AAV transduced cells may be evaluated to determine the AAV neutralizing antibody titer of the serum sample.

In one aspect, the present invention provides a kit for the detection of AAV neutralizing antibodies in serum samples, wherein the kit contains a fluorescently tagged (e.g., GFP) AAV vector, AAV permissive cells for incubating with the mixture of serum and fluorescently tagged AAV vector, and a medium.

In one aspect, the AAV permissive cells used for the method or the kit of the present invention may be any AAV permissive cell, including but not limited to, Huh7, Hela, HelaS3, Hepa1-6, HEK293, HepG2 or IMY-N9 cells. In one embodiment, the cells are Hela S3 cells.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead being placed upon illustrating the principles of various embodiments of the invention.

DETAILED DESCRIPTION OF THE INVENTION

Figure 1:
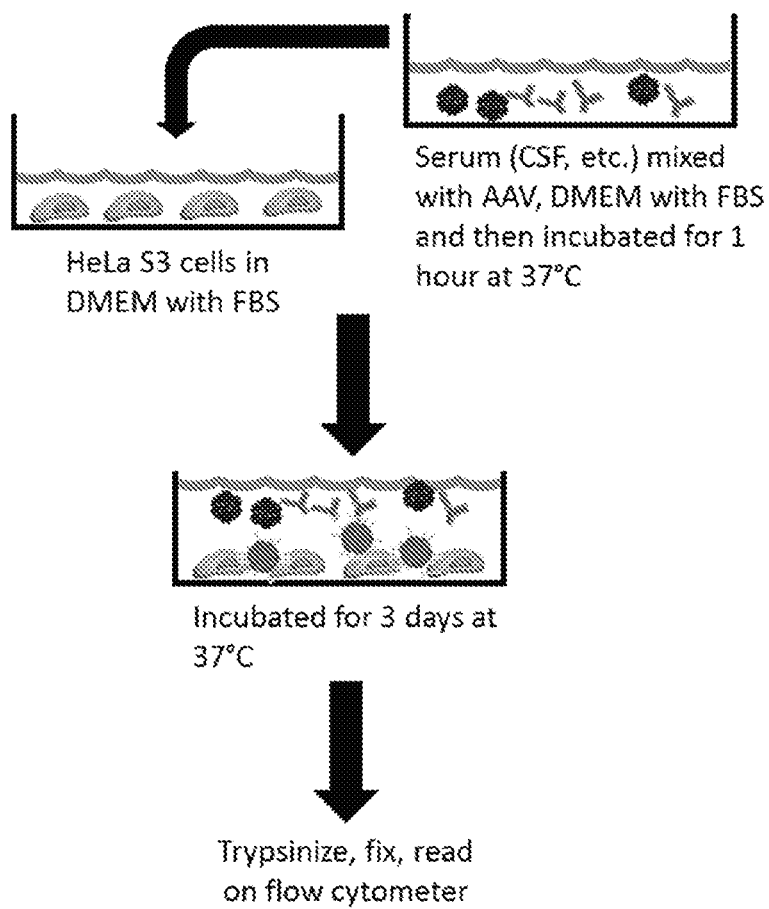
FIG. 1 is a diagram showing one embodiment of the assay described herein.

The details of one or more embodiments of the invention are set forth in the accompanying description below. Although any materials and methods similar or equivalent to those described herein can be used in the practice or testing of the present invention, the preferred materials and methods are now described. Other features, objects and advantages of the invention will be apparent from the description. In the description, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present description will control.

AAV vectors are the most widely used delivery system for in vivo gene therapy and genetic vaccine. The advantages in using AAV vectors include the non-pathogenic nature of AAV, the ability of AAV vectors to drive long-term transgene expression (e.g., in non-dividing cells) and the broad tropism of the AAV capsids and/or AAV serotypes and the 100s of AAV variants. Vectors developed from natural AAV isolates have achieved clinical benefit for a number of patients suffering from monogenetic disorders. However, the use of AAV vectors for gene therapy and genetic vaccine still faces significant hurdles. One of the obstacles is that the presence of pre-existing neutralizing antibodies precludes a number of patients from being treated with the use of a particular AAV vector. Epidemiology studies have predicted that ~70% of the population is seropositive for AAV2 and have estimated a lower degree of seroprevalence for other AAV capsids (Calcedo R et al., J Infect Dis, 2009, 199(3): 381-390; the content of which is incorporated herein by reference in its entirety). The pre-existing neutralizing antibodies cold block viral entry and transgene transduction to the targeted cells. In addition, target cells that are transduced with AAV vectors could become targets of the pre-existing T cell clones (e.g., CD8+ T cells) which react with viral capsid peptides which can cause destruction of transduced cells and even may prevent the expression of the transgene.

Assessment of neutralizing antibodies present in sera of a patient (or a human population) that is in need of AAV mediated gene therapy, and their cross reactivity with AAV capsids and/or AAV serotypes, is critical in selecting what AAV serotype sequences are used for a particular patient or a human population. The information may be used to optimize vector-host interactions in gene therapy and genetic vaccine. Also the detection of neutralizing antibodies induced by administration of AAV vectors is important for a patient's gene therapy such as, but not limited to, repeat administration.

Assessment of the pre-existing anti-AAV NAbs in sera is usually via viral neutralization assays for antibody detection. The current viral neutralization assay for antibody detection involves production of AAV vectors with the helper Adenovirus (Adv). Adenovirus (Adv) is a human pathogen and classified in the "NIH Guidelines" as a Risk Group 2. Infection by adenoviruses could cause respiratory illness and various other illnesses, such as gastroenteritis, conjunctivitis, cystitis (bladder infection), and rash illness. Occupational exposure to Adenovirus, through aerosols, fomite contact, fecal-oral route and/or percutaneous exposure, raises the risk of adenovirus infection in the laboratory. The potential for infection exists even when the workplace meets the laboratory biosafety level criteria.

Although the current assay method is considered reliable, it suffers from the potential of infection in the laboratory and the requirement of establishing a biosafety level workplace. The assessment methods require a rapid turn-around from sample collection and easy operation in a regular laboratory. Moreover, current assays may be influenced by pre-existing adenovirus (e.g., specific neutralizing antibodies) levels of which have no correlation to the levels of AAV-neutralizing antibodies. Additionally, current neutralization assays involve cell lysis for measuring AAV production which can yield inconsistent results.

The present methods in which the entry ability of AAV vectors is assessed can overcome these disadvantages by providing a system that does not necessitate the use of helper viruses, i.e., Adenoviruses; or cell lysis.

Adeno Associated Virus (AAV) Vectors

Adeno-associated viruses (AAVs) are small, single-stranded DNA (ssDNA) dependoviruses belonging to the parvovirus family, which are capable of replication in vertebrate hosts including, but not limited to, human, primate, bovine, canine, equine, and ovine species. AAVs have emerged as one of the most widely studied and utilized viral vectors for gene transfer to mammalian cells. See, e.g., Tratschin et al., Mol. Cell Biol., 1985, 5(11):3251-3260; and Grimm et al., Hum. Gene Ther., 1999, 10(15):2445-2450; the contents of each of which are herein incorporated by reference in their entirety. Importantly, AAV can also infect a wide range of host cells, including non-dividing cells (e.g., neurons in the central nervous system). AAV has not been associated with any human or animal disease, and does not appear to alter the physiological properties of the host cell upon integration. AAV vectors for use in therapeutics and/or diagnostics can be engineered to contain the minimum components necessary for transduction of a nucleic acid agent of interest. For example, viral vectors are engineered as vehicles for specific delivery while lacking the deleterious replication and/or integration features found in a wild-type virus.

The AAV genome is a linear, single-stranded DNA (ssDNA) molecule, including inverted terminal repeats (ITRs) which flank the coding nucleotide sequences for the non-structural proteins (encoded by Rep genes) and the structural proteins (encoded by capsid genes or Cap genes). The self-complementary terminals 145 nt of the 5' and 3' ends of the viral genomic ssDNA form a characteristic T-shaped hairpin structure, which can serve as priming sites for host-cell DNA polymerase to begin synthesis of the second (complementary) strand and as replication origins during productive infection. While not wishing to be bound by theory, an AAV replicating in a mammalian cell may include two ITR sequences. Replication of wild-type ssDNA AAV genomes begins at the 3' end of the genome where the self-complementary portion of the ITR is used as a primer for the initiation of DNA synthesis. Replication continues in the 5' to 3' direction until a double stranded hairpin structure has been formed with a loop at one end. Rep protein binds to the Rep binding sequence region near the end of the hairpin comprising the loop and nicks the DNA, allowing the resolution of the loop and formation of a linear double stranded DNA molecule. The complementary strands are then separated and the replication cycle continues on both resultant strands of ssDNA.

The Rep genes encode the non-structural proteins that regulate functions comprising the replication of the AAV vector genome. Rep78 and Rep68 are transcribed from the p5 promoter, and Rep52 and Rep40 are transcribed from the p19 promoter. The cap gene encodes three capsid proteins, Vp1, Vp2, and Vp3, produced in a 1:1:10 ratio from the same open reading frame but from differential splicing (Vp1) and alternative translational start sites (Vp2 and Vp3, respectively). Vp1, Vp2 and Vp3 subunits assemble to form the capsid. Vp3 is the most abundant subunit and participates in receptor recognition at the cell surface thereby defining the tropism of the virus.

Transduction of a target cell by AAV is dependent on a stepwise series of events including, but not limited to, cell surface binding, endocytic uptake, endosomal escape, nuclear entry, capsid uncoating, release of the ssDNA genome, second strand synthesis, transcription of the genome, and replication of the genome (Murlidharan et al. 2014, *Frontiers in Molecular Neuroscience*. 2014, 7:76). In addition to the few gene products of the AAV genome, productive wild type AAV infection is dependent on the presence of adenovirus co-infection which supplies helper genes E1a, E1b, E2a, E4, and VA. These helper genes provide transactivation activity, aid in transcription of the AAV genome, and facilitate AAV mRNA processing.

Viral vectors used for delivering a polynucleotide of interest may comprise the viral genome, in part or entirety, of any naturally occurring and/or recombinant AAV nucleotide sequence or variant. AAV variants may have genomic sequences of significant homology at the nucleic acid and amino acid levels, produce viral vectors which are generally physical and functional equivalents, replicate by similar mechanisms, and assemble by similar mechanisms, as compared to the parent AAV (Chiorini et al., *J. Vir.* 1997, 71: 6823-33; Srivastava et al., *J. Vir.* 1983, 45:555-564; Chiorini et al., *J. Vir.* 1999, 73:1309-1319; Rutledge et al., *J. Vir.* 1998, 72:309-319; and Wu et al., *J. Vir.* 2000, 74: 8635-47, the contents of each of which are herein incorporated by reference in their entirety).

An AAV vector may use genomic sequences from any viral serotype. Viral serotypes are distinct variations within a species of viruses, e.g., in the context of the present invention, AAVs, which are classified together based on their cell surface antigens (e.g., capsid). Viral variants of the same serotype share common antigens. Hundreds of AAV variants have been isolated from non-primates, primates and humans. An AAV vector may use an AAV sequence or fragment thereof from an AAV serotype such as, but not limited to, AAV1, AAV2, AAV2G9, AAV3, AAV3a, AAV3b, AAV3-3, AAV4, AAV4-4, AAV5, AAV6, AAV6.1, AAV6.2, AAV6.1.2, AAV7, AAV7.2, AAV8, AAV9, AAV9.11, AAV9.13, AAV9.16, AAV9.24, AAV9.45, AAV9.47, AAV9.61, AAV9.68, AAV9.84, AAV9.9, AAV10, AAV11, AAV12, AAV16.3, AAV24.1, AAV27.3, AAV42.12, AAV42-1b, AAV42-2, AAV42-3a, AAV42-3b, AAV42-4, AAV42-5a, AAV42-5b, AAV42-6b, AAV42-8, AAV42-10, AAV42-11, AAV42-12, AAV42-13, AAV42-15, AAV42-aa, AAV43-1, AAV43-12, AAV43-20, AAV43-21, AAV43-23, AAV43-25, AAV43-5, AAV44.1, AAV44.2, AAV44.5, AAV223.1, AAV223.2, AAV223.4, AAV223.5, AAV223.6, AAV223.7, AAV1-7/rh.48, AAV1-8/rh.49, AAV2-15/rh.62, AAV2-3/rh.61, AAV2-4/rh.50, AAV2-5/rh.51, AAV3.1/hu.6, AAV3.1/hu.9, AAV3-9/rh.52, AAV3-11/rh.53, AAV4-8/r11.64, AAV4-9/rh.54, AAV4-19/rh.55, AAV5-3/rh.57, AAV5-22/rh.58, AAV7.3/hu.7, AAV16.8/hu.10, AAV16.12/hu.11, AAV29.3/bb.1, AAV29.5/bb.2, AAV106.1/hu.37, AAV114.3/hu.40, AAV127.2/hu.41, AAV127.5/hu.42, AAV128.3/hu.44, AAV130.4/hu.48, AAV145.1/hu.53, AAV145.5/hu.54, AAV145.6/hu.55, AAV161.10/hu.60, AAV161.6/hu.61, AAV33.12/hu.17, AAV33.4/hu.15, AAV33.8/hu.16, AAV52/hu.19, AAV52.1/hu.20, AAV58.2/hu.25, AAVA3.3, AAVA3.4, AAVA3.5, AAVA3.7, AAVC1, AAVC2, AAVC5, AAV-DJ, AAV-DJ8, AAVF3, AAVF5, AAVH2, AAVrh.72, AAVhu.8, AAVrh.68, AAVrh.70, AAVpi.1, AAVpi.3, AAVpi.2, AAVrh.60, AAVrh.44, AAVrh.65, AAVrh.55, AAVrh.47, AAVrh.69, AAVrh.45, AAVrh.59, AAVhu.12, AAVH6, AAVLK03, AAVH-1/hu.1, AAVH-5/hu.3, AAVLG-10/rh.40, AAVLG-4/rh.38, AAVLG-9/hu.39, AAVN721-8/rh.43, AAVCh.5, AAVCh.5R1, AAVcy.2, AAVcy.3, AAVcy.4, AAVcy.5, AAVCy.5R1, AAVCy.5R2, AAVCy.5R3, AAVCy.5R4, AAVcy.6, AAVhu.1, AAVhu.2, AAVhu.3, AAVhu.4, AAVhu.5, AAVhu.6, AAVhu.7, AAVhu.9, AAVhu.10, AAVhu.11, AAVhu.13, AAVhu.15, AAVhu.16, AAVhu.17, AAVhu.18, AAVhu.20, AAVhu.21, AAVhu.22, AAVhu.23.2, AAVhu.24, AAVhu.25, AAVhu.27, AAVhu.28, AAVhu.29, AAVhu.29R, AAVhu.31, AAVhu.32, AAVhu.34, AAVhu.35, AAVhu.37, AAVhu.39, AAVhu.40, AAVhu.41, AAVhu.42, AAVhu.43, AAVhu.44, AAVhu.44R1, AAVhu.44R2, AAVhu.44R3, AAVhu.45, AAVhu.46, AAVhu.47, AAVhu.48, AAVhu.48R1, AAVhu.48R2, AAVhu.48R3, AAVhu.49, AAVhu.51, AAVhu.52, AAVhu.54, AAVhu.55, AAVhu.56, AAVhu.57, AAVhu.58, AAVhu.60, AAVhu.61, AAVhu.63, AAVhu.64, AAVhu.66, AAVhu.67, AAVhu.14/9, AAVhu.t 19, AAVrh.2, AAVrh.2R, AAVrh.8, AAVrh.8R, AAVrh.10, AAVrh.12, AAVrh.13, AAVrh.13R, AAVrh.14, AAVrh.17, AAVrh.18, AAVrh.19, AAVrh.20, AAVrh.21, AAVrh.22, AAVrh.23, AAVrh.24, AAVrh.25, AAVrh.31, AAVrh.32, AAVrh.33, AAVrh.34, AAVrh.35, AAVrh.36, AAVrh.37, AAVrh.37R2, AAVrh.38, AAVrh.39, AAVrh.40, AAVrh.46, AAVrh.48, AAVrh.48.1, AAVrh.48.1.2, AAVrh.48.2, AAVrh.49, AAVrh.51, AAVrh.52, AAVrh.53, AAVrh.54, AAVrh.56, AAVrh.57, AAVrh.58, AAVrh.61, AAVrh.64, AAVrh.64R1, AAVrh.64R2, AAVrh.67, AAVrh.73, AAVrh.74, AAVrh8R, AAVrh8R A586R mutant, AAVrh8R R533A mutant, AAAV, BAAV, caprine AAV, bovine AAV, AAVhE1.1, AAVhEr1.5, AAVhER1.14, AAVhEr1.8, AAVhEr1.16, AAVhEr1.18, AAVhEr1.35, AAVhEr1.7, AAVhEr1.36, AAVhEr2.29, AAVhEr2.4, AAVhEr2.16, AAVhEr2.30, AAVhEr2.31, AAVhEr2.36, AAVhER1.23, AAVhEr3.1, AAV2.5T, AAV-PAEC, AAV-LK01, AAV-LK02, AAV-LK03, AAV-LK04, AAV-LK05, AAV-LK06, AAV-LK07, AAV-LK08, AAV-LK09, AAV-LK10, AAV-LK11, AAV-LK12, AAV-LK13, AAV-LK14, AAV-LK15, AAV-LK16, AAV-LK17, AAV-LK18, AAV-LK19, AAV-PAEC2, AAV-PAEC4, AAV-PAEC6, AAV-PAEC7, AAV-PAEC8, AAV-PAEC11, AAV-PAEC12, AAV-2-pre-miRNA-101, AAV-8h, AAV-8b, AAV-h, AAV-b, AAV SM 10-2, AAV Shuffle 100-1, AAV Shuffle 100-3, AAV Shuffle 100-7, AAV Shuffle 10-2, AAV Shuffle 10-6, AAV Shuffle 10-8, AAV Shuffle 100-2, AAV SM 10-1, AAV SM 10-8, AAV SM 100-3, AAV SM 100-10, BNP61 AAV, BNP62 AAV, BNP63 AAV, AAVrh.50, AAVrh.43, AAVrh.62, AAVrh.48, AAVhu.19, AAVhu.11, AAVhu.53, AAV4-8/rh.64, AAVLG-9/hu.39, AAV54.5/hu.23, AAV54.2/hu.22, AAV54.7/hu.24, AAV54.1/hu.21, AAV54.4R/hu.27, AAV46.2/hu.28, AAV46.6/hu.29, AAV128.1/hu.43, true type AAV (ttAAV), UPENN AAV 10 and/or Japanese AAV 10 serotypes, and variants thereof.

In some embodiments, the AAV serotype may be, or have, a sequence as described in United States Publication No. US20030138772, the contents of which are herein incorporated by reference in their entirety, such as, but not limited to, AAV1 (SEQ ID NO: 6 and 64 of US20030138772), AAV2 (SEQ ID NO: 7 and 70 of US20030138772), AAV3 (SEQ ID NO: 8 and 71 of US20030138772), AAV4 (SEQ ID NO: 63 of US20030138772), AAV5 (SEQ ID NO: 114 of US20030138772), AAV6 (SEQ ID NO: 65 of US20030138772), AAV7 (SEQ ID NO: 1-3 of US20030138772), AAV8 (SEQ ID NO: 4 and 95 of US20030138772), AAV9 (SEQ ID NO: 5 and 100 of US20030138772), AAV10 (SEQ ID NO: 117 of US20030138772), AAV11 (SEQ ID NO: 118 of US20030138772), AAV12 (SEQ ID NO: 119 of US20030138772), AAVrh10 (amino acids 1 to 738 of SEQ ID NO: 81 of US20030138772), AAV16.3 (US20030138772 SEQ ID NO: 10), AAV29.3/bb.1 (US20030138772 SEQ ID NO: 11), AAV29.4 (US20030138772 SEQ ID NO: 12), AAV29.5/bb.2 (US20030138772 SEQ ID NO: 13), AAV1.3 (US20030138772 SEQ ID NO: 14), AAV13.3 (US20030138772 SEQ ID NO: 15), AAV24.1 (US20030138772 SEQ ID NO: 16), AAV27.3 (US20030138772 SEQ ID NO: 17), AAV7.2 (US20030138772 SEQ ID NO: 18), AAVC1 (US20030138772 SEQ ID NO: 19), AAVC3 (US20030138772 SEQ ID NO: 20), AAVC5 (US20030138772 SEQ ID NO: 21), AAVF1 (US20030138772 SEQ ID NO: 22), AAVF3 (US20030138772 SEQ ID NO: 23), AAVF5 (US20030138772 SEQ ID NO: 24), AAVH6 (US20030138772 SEQ ID NO: 25), AAVH2 (US20030138772 SEQ ID NO: 26), AAV42-8 (US20030138772 SEQ ID NO: 27), AAV42-15 (US20030138772 SEQ ID NO: 28), AAV42-5b (US20030138772 SEQ ID NO: 29), AAV42-1b (US20030138772 SEQ ID NO: 30), AAV42-13 (US20030138772 SEQ ID NO: 31), AAV42-3a (US20030138772 SEQ ID NO: 32), AAV42-4 (US20030138772 SEQ ID NO: 33), AAV42-5a (US20030138772 SEQ ID NO: 34), AAV42-10 (US20030138772 SEQ ID NO: 35), AAV42-3b (US20030138772 SEQ ID NO: 36), AAV42-11 (US20030138772 SEQ ID NO: 37), AAV42-6b (US20030138772 SEQ ID NO: 38), AAV43-1 (US20030138772 SEQ ID NO: 39), AAV43-5 (US20030138772 SEQ ID NO: 40), AAV43-12 (US20030138772 SEQ ID NO: 41), AAV43-20 (US20030138772 SEQ ID NO: 42), AAV43-21 (US20030138772 SEQ ID NO: 43), AAV43-23 (US20030138772 SEQ ID NO: 44), AAV43-25 (US20030138772 SEQ ID NO: 45), AAV44.1 (US20030138772 SEQ ID NO: 46), AAV44.5 (US20030138772 SEQ ID NO: 47), AAV223.1 (US20030138772 SEQ ID NO: 48), AAV223.2 (US20030138772 SEQ ID NO: 49), AAV223.4 (US20030138772 SEQ ID NO: 50), AAV223.5 (US20030138772 SEQ ID NO: 51), AAV223.6 (US20030138772 SEQ ID NO: 52), AAV223.7 (US20030138772 SEQ ID NO: 53), AAVA3.4 (US20030138772 SEQ ID NO: 54), AAVA3.5 (US20030138772 SEQ ID NO: 55), AAVA3.7 (US20030138772 SEQ ID NO: 56), AAVA3.3 (US20030138772 SEQ ID NO: 57), AAV42.12 (US20030138772 SEQ ID NO: 58), AAV44.2 (US20030138772 SEQ ID NO: 59), AAV42-2 (US20030138772 SEQ ID NO: 9), or variants thereof.

In some embodiments, the AAV serotype may be, or have, a sequence as described in United States Publication No. US20150159173, the contents of which are herein incorporated by reference in their entirety, such as, but not limited to, AAV2 (SEQ ID NO: 7 and 23 of US20150159173), rh20 (SEQ ID NO: 1 of US20150159173), rh32/33 (SEQ ID NO: 2 of US20150159173), rh39 (SEQ ID NO: 3, 20 and 36 of US20150159173), rh46 (SEQ ID NO: 4 and 22 of US20150159173), rh73 (SEQ ID NO: 5 of US20150159173), rh74 (SEQ ID NO: 6 of US20150159173), AAV6.1 (SEQ ID NO: 29 of US20150159173), rh.8 (SEQ ID NO: 41 of US20150159173), rh.48.1 (SEQ ID NO: 44 of US20150159173), hu.44 (SEQ ID NO: 45 of US20150159173), hu.29 (SEQ ID NO: 42 of US20150159173), hu.48 (SEQ ID NO: 38 of US20150159173), rh54 (SEQ ID NO: 49 of US20150159173), AAV2 (SEQ ID NO: 7 of US20150159173), cy.5 (SEQ ID NO: 8 and 24 of US20150159173), rh.10 (SEQ ID NO: 9 and 25 of US20150159173), rh.13 (SEQ ID NO: 10 and 26 of US20150159173), AAV1 (SEQ ID NO: 11 and 27 of US20150159173), AAV3 (SEQ ID NO: 12 and 28 of US20150159173), AAV6 (SEQ ID NO: 13 and 29 of US20150159173), AAV7 (SEQ ID NO: 14 and 30 of US20150159173), AAV8 (SEQ ID NO: 15 and 31 of US20150159173), hu.13 (SEQ ID NO: 16 and 32 of US20150159173), hu.26 (SEQ ID NO: 17 and 33 of US20150159173), hu.37 (SEQ ID NO: 18 and 34 of US20150159173), hu.53 (SEQ ID NO: 19 and 35 of US20150159173), rh.43 (SEQ ID NO: 21 and 37 of US20150159173), rh2 (SEQ ID NO: 39 of US20150159173), rh.37 (SEQ ID NO: 40 of US20150159173), rh.64 (SEQ ID NO: 43 of US20150159173), rh.48 (SEQ ID NO: 44 of US20150159173), ch.5 (SEQ ID NO 46 of US20150159173), rh.67 (SEQ ID NO: 47 of US20150159173), rh.58 (SEQ ID NO: 48 of US20150159173), or variants thereof including, but not limited to Cy5R1, Cy5R2, Cy5R3, Cy5R4, rh.13R, rh.37R2, rh.2R, rh.8R, rh.48.1, rh.48.2, rh.48.1.2, hu.44R1, hu.44R2, hu.44R3, hu.29R, ch.5R1, rh64R1, rh64R2, AAV6.2, AAV6.1, AAV6.12, hu.48R1, hu.48R2, and hu.48R3.

In some embodiments, the AAV serotype may be, or have, a sequence as described in U.S. Pat. No. 7,198,951, the contents of which are herein incorporated by reference in their entirety, such as, but not limited to, AAV9 (SEQ ID NO: 1-3 of U.S. Pat. No. 7,198,951), AAV2 (SEQ ID NO: 4 of U.S. Pat. No. 7,198,951), AAV1 (SEQ ID NO: 5 of U.S. Pat. No. 7,198,951), AAV3 (SEQ ID NO: 6 of U.S. Pat. No. 7,198,951), and AAV8 (SEQ ID NO: 7 of U.S. Pat. No. 7,198,951).

In some embodiments, the AAV serotype may be, or have, a mutation in the AAV9 sequence as described by N Pulicherla et al. (Molecular Therapy 19(6):1070-1078 (2011), herein incorporated by reference in its entirety), such as but not limited to, AAV9.9, AAV9.11, AAV9.13, AAV9.16, AAV9.24, AAV9.45, AAV9.47, AAV9.61, AAV9.68, AAV9.84 or derivatives thereof.

In some embodiments, the AAV serotype may be, or have, a sequence as described in U.S. Pat. No. 6,156,303, the contents of which are herein incorporated by reference in their entirety, such as, but not limited to, AAV3B (SEQ ID NO: 1 and 10 of U.S. Pat. No. 6,156,303), AAV6 (SEQ ID NO: 2, 7 and 11 of U.S. Pat. No. 6,156,303), AAV2 (SEQ ID NO: 3 and 8 of U.S. Pat. No. 6,156,303), AAV3A (SEQ ID NO: 4 and 9, of U.S. Pat. No. 6,156,303), or derivatives thereof.

In some embodiments, the AAV serotype may be, or have, a sequence as described in United States Publication No. US20140359799, the contents of which are herein incorporated by reference in their entirety, such as, but not limited to, AAV8 (SEQ ID NO: 1 of US20140359799), AAVDJ (SEQ ID NO: 2 and 3 of US20140359799), or variants thereof.

In some embodiments, the serotype may be AAVDJ or a variant thereof, such as AAVDJ8 (or AAV-DJ8), as described by Grimm et al. (Journal of Virology 82(12): 5887-5911 (2008), herein incorporated by reference in its entirety). The amino acid sequence of AAVDJ8 may comprise two or more mutations in order to remove the heparin binding domain (HBD). As a non-limiting example, the AAV-DJ sequence described as SEQ ID NO: 1 in U.S. Pat. No. 7,588,772, the contents of which are herein incorporated by reference in their entirety, may comprise two mutations: (1) R587Q where arginine (R; Arg) at amino acid 587 is changed to glutamine (Q; Gln) and (2) R590T where arginine (R; Arg) at amino acid 590 is changed to threonine (T; Thr). As another non-limiting example, may comprise three mutations: (1) K406R where lysine (K; Lys) at amino acid 406 is changed to arginine (R; Arg), (2) R587Q where arginine (R; Arg) at amino acid 587 is changed to glutamine (Q; Gln) and (3) R590T where arginine (R; Arg) at amino acid 590 is changed to threonine (T; Thr).

In some embodiments, the AAV serotype may be, or have, a sequence of AAV4 as described in International Publication No. WO1998011244, the contents of which are herein incorporated by reference in their entirety, such as, but not limited to AAV4 (SEQ ID NO: 1-20 of WO1998011244).

In some embodiments, the AAV serotype may be, or have, a mutation in the AAV2 sequence to generate AAV2G9 as described in International Publication No. WO2014144229 and herein incorporated by reference in its entirety.

In some embodiments, the AAV serotype may be, or have, a sequence as described in International Publication No. WO2005033321, the contents of which are herein incorporated by reference in their entirety, such as, but not limited to AAV3-3 (SEQ ID NO: 217 of WO2005033321), AAV1 (SEQ ID NO: 219 and 202 of WO2005033321), AAV106.1/hu.37 (SEQ ID No: 10 of WO2005033321), AAV114.3/hu.40 (SEQ ID No: 11 of WO2005033321), AAV127.2/hu.41 (SEQ ID NO:6 and 8 of WO2005033321), AAV128.3/hu.44 (SEQ ID No: 81 of WO2005033321), AAV130.4/hu.48 (SEQ ID NO: 78 of WO2005033321), AAV145.1/hu.53 (SEQ ID No: 176 and 177 of WO2005033321), AAV145.6/hu.56 (SEQ ID NO: 168 and 192 of WO2005033321), AAV16.12/hu.11 (SEQ ID NO: 153 and 57 of WO2005033321), AAV16.8/hu.10 (SEQ ID NO: 156 and 56 of WO2005033321), AAV161.10/hu.60 (SEQ ID No: 170 of WO2005033321), AAV161.6/hu.61 (SEQ ID No: 174 of WO2005033321), AAV1-7/rh.48 (SEQ ID NO: 32 of WO2005033321), AAV1-8/rh.49 (SEQ ID NOs: 103 and 25 of WO2005033321), AAV2 (SEQ ID NO: 211 and 221 of WO2005033321), AAV2-15/rh.62 (SEQ ID No: 33 and 114 of WO2005033321), AAV2-3/rh.61 (SEQ ID NO: 21 of WO2005033321), AAV2-4/rh.50 (SEQ ID No: 23 and 108 of WO2005033321), AAV2-5/rh.51 (SEQ ID NO: 104 and 22 of WO2005033321), AAV3.1/hu.6 (SEQ ID NO: 5 and 84 of WO2005033321), AAV3.1/hu.9 (SEQ ID NO: 155 and 58 of WO2005033321), AAV3-11/rh.53 (SEQ ID NO: 186 and 176 of WO2005033321), AAV3-3 (SEQ ID NO: 200 of WO2005033321), AAV33.12/hu.17 (SEQ ID NO:4 of WO2005033321), AAV33.4/hu.15 (SEQ ID No: 50 of WO2005033321), AAV33.8/hu.16 (SEQ ID No: 51 of WO2005033321), AAV3-9/rh.52 (SEQ ID NO: 96 and 18 of WO2005033321), AAV4-19/rh.55 (SEQ ID NO: 117 of WO2005033321), AAV4-4 (SEQ ID NO: 201 and 218 of WO2005033321), AAV4-9/rh.54 (SEQ ID NO: 116 of WO2005033321), AAV5 (SEQ ID NO: 199 and 216 of WO2005033321), AAV52.1/hu.20 (SEQ ID NO: 63 of WO2005033321), AAV52/hu.19 (SEQ ID NO: 133 of WO2005033321), AAV5-22/rh.58 (SEQ ID No: 27 of WO2005033321), AAV5-3/rh.57 (SEQ ID NO: 105 of WO2005033321), AAV5-3/rh.57 (SEQ ID No: 26 of WO2005033321), AAV58.2/hu.25 (SEQ ID No: 49 of WO2005033321), AAV6 (SEQ ID NO: 203 and 220 of WO2005033321), AAV7 (SEQ ID NO: 222 and 213 of WO2005033321), AAV7.3/hu.7 (SEQ ID No: 55 of WO2005033321), AAV8 (SEQ ID NO: 223 and 214 of WO2005033321), AAVH-1/hu.1 (SEQ ID No: 46 of WO2005033321), AAVH-5/hu.3 (SEQ ID No: 44 of WO2005033321), AAVhu.1 (SEQ ID NO: 144 of WO2005033321), AAVhu.10 (SEQ ID NO: 156 of WO2005033321), AAVhu.11 (SEQ ID NO: 153 of WO2005033321), AAVhu.12 (WO2005033321 SEQ ID NO: 59), AAVhu.13 (SEQ ID NO: 129 of WO2005033321), AAVhu.14/AAV9 (SEQ ID NO: 123 and 3 of WO2005033321), AAVhu.15 (SEQ ID NO: 147 of WO2005033321), AAVhu.16 (SEQ ID NO: 148 of WO2005033321), AAVhu.17 (SEQ ID NO: 83 of WO2005033321), AAVhu.18 (SEQ ID NO: 149 of WO2005033321), AAVhu.19 (SEQ ID NO: 133 of WO2005033321), AAVhu.2 (SEQ ID NO: 143 of WO2005033321), AAVhu.20 (SEQ ID NO: 134 of WO2005033321), AAVhu.21 (SEQ ID NO: 135 of WO2005033321), AAVhu.22 (SEQ ID NO: 138 of WO2005033321), AAVhu.23.2 (SEQ ID NO: 137 of WO2005033321), AAVhu.24 (SEQ ID NO: 136 of WO2005033321), AAVhu.25 (SEQ ID NO: 146 of WO2005033321), AAVhu.27 (SEQ ID NO: 140 of WO2005033321), AAVhu.29 (SEQ ID NO: 132 of WO2005033321), AAVhu.3 (SEQ ID NO: 145 of WO2005033321), AAVhu.31 (SEQ ID NO: 121 of WO2005033321), AAVhu.32 (SEQ ID NO: 122 of WO2005033321), AAVhu.34 (SEQ ID NO: 125 of WO2005033321), AAVhu.35 (SEQ ID NO: 164 of WO2005033321), AAVhu.37 (SEQ ID NO: 88 of WO2005033321), AAVhu.39 (SEQ ID NO: 102 of WO2005033321), AAVhu.4 (SEQ ID NO: 141 of WO2005033321), AAVhu.40 (SEQ ID NO: 87 of WO2005033321), AAVhu.41 (SEQ ID NO: 91 of WO2005033321), AAVhu.42 (SEQ ID NO: 85 of WO2005033321), AAVhu.43 (SEQ ID NO: 160 of WO2005033321), AAVhu.44 (SEQ ID NO: 144 of WO2005033321), AAVhu.45 (SEQ ID NO: 127 of WO2005033321), AAVhu.46 (SEQ ID NO: 159 of WO2005033321), AAVhu.47 (SEQ ID NO: 128 of WO2005033321), AAVhu.48 (SEQ ID NO: 157 of WO2005033321), AAVhu.49 (SEQ ID NO: 189 of WO2005033321), AAVhu.51 (SEQ ID NO: 190 of WO2005033321), AAVhu.52 (SEQ ID NO: 191 of WO2005033321), AAVhu.53 (SEQ ID NO: 186 of WO2005033321), AAVhu.54 (SEQ ID NO: 188 of WO2005033321), AAVhu.55 (SEQ ID NO: 187 of WO2005033321), AAVhu.56 (SEQ ID NO: 192 of WO2005033321), AAVhu.57 (SEQ ID NO: 193 of WO2005033321), AAVhu.58 (SEQ ID NO: 194 of WO2005033321), AAVhu.6 (SEQ ID NO: 84 of WO2005033321), AAVhu.60 (SEQ ID NO: 184 of WO2005033321), AAVhu.61 (SEQ ID NO: 185 of WO2005033321), AAVhu.63 (SEQ ID NO: 195 of WO2005033321), AAVhu.64 (SEQ ID NO: 196 of WO2005033321), AAVhu.66 (SEQ ID NO: 197 of WO2005033321), AAVhu.67 (SEQ ID NO: 198 of WO2005033321), AAVhu.7 (SEQ ID NO: 150 of WO2005033321), AAVhu.8 (WO2005033321 SEQ ID NO: 12), AAVhu.9 (SEQ ID NO: 155 of WO2005033321), AAVLG-10/rh.40 (SEQ ID No: 14 of WO2005033321), AAVLG-4/rh.38 (SEQ ID NO: 86 of WO2005033321), AAVLG-4/rh.38 (SEQ ID No: 7 of WO2005033321), AAVN721-8/rh.43 (SEQ ID NO: 163 of WO2005033321), AAVN721-8/rh.43 (SEQ ID No: 43 of WO2005033321), AAVpi.1 (WO2005033321 SEQ ID NO: 28), AAVpi.2 (WO2005033321 SEQ ID NO: 30), AAVpi.3 (WO2005033321 SEQ ID NO: 29), AAVrh.38 (SEQ ID NO: 86 of WO2005033321), AAVrh.40 (SEQ ID NO: 92 of WO2005033321), AAVrh.43 (SEQ ID NO: 163 of WO2005033321), AAVrh.44 (WO2005033321 SEQ ID NO: 34), AAVrh.45 (WO2005033321 SEQ ID NO: 41), AAVrh.47 (WO2005033321 SEQ ID NO: 38), AAVrh.48 (SEQ ID NO: 115 of WO2005033321), AAVrh.49 (SEQ ID NO: 103 of WO2005033321), AAVrh.50 (SEQ ID NO: 108 of WO2005033321), AAVrh.51 (SEQ ID NO: 104 of WO2005033321), AAVrh.52 (SEQ ID NO: 96 of WO2005033321), AAVrh.53 (SEQ ID NO: 97 of WO2005033321), AAVrh.55 (WO2005033321 SEQ ID NO: 37), AAVrh.56 (SEQ ID NO: 152 of WO2005033321), AAVrh.57 (SEQ ID NO: 105 of WO2005033321), AAVrh.58 (SEQ ID NO: 106 of WO2005033321), AAVrh.59 (WO2005033321 SEQ ID NO: 42), AAVrh.60 (WO2005033321 SEQ ID NO: 31), AAVrh.61 (SEQ ID NO: 107 of WO2005033321), AAVrh.62 (SEQ ID NO: 114 of WO2005033321), AAVrh.64 (SEQ ID NO: 99 of WO2005033321), AAVrh.65 (WO2005033321 SEQ ID NO: 35), AAVrh.68 (WO2005033321 SEQ ID NO: 16), AAVrh.69 (WO2005033321 SEQ ID NO: 39), AAVrh.70 (WO2005033321 SEQ ID NO: 20), AAVrh.72 (WO2005033321 SEQ ID NO: 9), or variants thereof including, but not limited to, AAVcy.2, AAVcy.3, AAVcy.4, AAVcy.5, AAVcy.6, AAVrh.12, AAVrh.17, AAVrh.18, AAVrh.19, AAVrh.21, AAVrh.22, AAVrh.23, AAVrh.24, AAVrh.25, AAVrh.25/42 15, AAVrh.31, AAVrh.32, AAVrh.33, AAVrh.34, AAVrh.35, AAVrh.36, AAVrh.37, AAVrh14. Non limiting examples of variants include SEQ ID NO: 13, 15, 17, 19, 24, 36, 40, 45, 47, 48, 51-54, 60-62, 64-77, 79, 80, 82, 89, 90, 93-95, 98, 100, 101, 109-113, 118-120, 124, 126, 131, 139, 142, 151, 154, 158, 161, 162, 165-183, 202, 204-212, 215, 219, 224-236, of WO2005033321, the contents of which are herein incorporated by reference in their entirety.

In some embodiments, the AAV serotype may be, or have, a sequence as described in International Publication No. WO2015168666, the contents of which are herein incorporated by reference in their entirety, such as, but not limited to, AAVrh8R (SEQ ID NO: 9 of WO2015168666), AAVrh8R A586R mutant (SEQ ID NO: 10 of WO2015168666), AAVrh8R R533A mutant (SEQ ID NO: 11 of WO2015168666), or variants thereof.

In some embodiments, the AAV serotype may be, or have, a sequence as described in U.S. Pat. No. 9,233,131, the contents of which are herein incorporated by reference in their entirety, such as, but not limited to, AAVhE1.1 (SEQ ID NO:44 of U.S. Pat. No. 9,233,131), AAVhEr1.5 (SEQ ID NO:45 of U.S. Pat. No. 9,233,131), AAVhER1.14 (SEQ ID NO:46 of U.S. Pat. No. 9,233,131), AAVhEr1.8 (SEQ ID NO:47 of U.S. Pat. No. 9,233,131), AAVhEr1.16 (SEQ ID NO:48 of U.S. Pat. No. 9,233,131), AAVhEr1.18 (SEQ ID NO:49 of U.S. Pat. No. 9,233,131), AAVhEr1.35 (SEQ ID NO:50 of U.S. Pat. No. 9,233,131), AAVhEr1.7 (SEQ ID NO:51 of U.S. Pat. No. 9,233,131), AAVhEr1.36 (SEQ ID NO:52 of U.S. Pat. No. 9,233,131), AAVhEr2.29 (SEQ ID NO:53 of U.S. Pat. No. 9,233,131), AAVhEr2.4 (SEQ ID NO:54 of U.S. Pat. No. 9,233,131), AAVhEr2.16 (SEQ ID NO:55 of U.S. Pat. No. 9,233,131), AAVhEr2.30 (SEQ ID NO:56 of U.S. Pat. No. 9,233,131), AAVhEr2.31 (SEQ ID NO:58 of U.S. Pat. No. 9,233,131), AAVhEr2.36 (SEQ ID NO:57 of U.S. Pat. No. 9,233,131), AAVhER1.23 (SEQ ID NO:53 of U.S. Pat. No. 9,233,131), AAVhEr3.1 (SEQ ID NO:59 of U.S. Pat. No. 9,233,131), AAV2.5T (SEQ ID NO:42 of U.S. Pat. No. 9,233,131), or variants thereof.

In some embodiments, the AAV serotype may be, or have, a sequence as described in United States Patent Publication No. US20150376607, the contents of which are herein incorporated by reference in their entirety, such as, but not limited to, AAV-PAEC (SEQ ID NO:1 of US20150376607), AAV-LK01 (SEQ ID NO:2 of US20150376607), AAV-LKO2 (SEQ ID NO:3 of US20150376607), AAV-LKO3 (SEQ ID NO:4 of US20150376607), AAV-LKO4 (SEQ ID NO:5 of US20150376607), AAV-LKO5 (SEQ ID NO:6 of US20150376607), AAV-LKO6 (SEQ ID NO:7 of US20150376607), AAV-LKO7 (SEQ ID NO:8 of US20150376607), AAV-LKO8 (SEQ ID NO:9 of US20150376607), AAV-LKO9 (SEQ ID NO:10 of US20150376607), AAV-LK10 (SEQ ID NO:11 of US20150376607), AAV-LK11 (SEQ ID NO:12 of US20150376607), AAV-LK12 (SEQ ID NO:13 of US20150376607), AAV-LK13 (SEQ ID NO:14 of US20150376607), AAV-LK14 (SEQ ID NO:15 of US20150376607), AAV-LK15 (SEQ ID NO:16 of US20150376607), AAV-LK16 (SEQ ID NO:17 of US20150376607), AAV-LK17 (SEQ ID NO:18 of US20150376607), AAV-LK18 (SEQ ID NO:19 of US20150376607), AAV-LK19 (SEQ ID NO:20 of US20150376607), AAV-PAEC2 (SEQ ID NO:21 of US20150376607), AAV-PAEC4 (SEQ ID NO:22 of US20150376607), AAV-PAEC6 (SEQ ID NO:23 of US20150376607), AAV-PAEC7 (SEQ ID NO:24 of US20150376607), AAV-PAEC8 (SEQ ID NO:25 of US20150376607), AAV-PAEC11 (SEQ ID NO:26 of US20150376607), AAV-PAEC12 (SEQ ID NO:27, of US20150376607), or variants thereof.

In some embodiments, the AAV serotype may be, or have, a sequence as described in U.S. Pat. No. 9,163,261, the contents of which are herein incorporated by reference in their entirety, such as, but not limited to, AAV-2-pre-miRNA-101 (SEQ ID NO: 1 U.S. Pat. No. 9,163,261), or variants thereof.

In some embodiments, the AAV serotype may be, or have, a sequence as described in United States Patent Publication No. US20150376240, the contents of which are herein incorporated by reference in their entirety, such as, but not limited to, AAV-8h (SEQ ID NO: 6 of US20150376240), AAV-8b (SEQ ID NO: 5 of US20150376240), AAV-h (SEQ ID NO: 2 of US20150376240), AAV-b (SEQ ID NO: 1 of US20150376240), or variants thereof.

In some embodiments, the AAV serotype may be, or have, a sequence as described in United States Patent Publication No. US20160017295, the contents of which are herein incorporated by reference in their entirety, such as, but not limited to, AAV SM 10-2 (SEQ ID NO: 22 of US20160017295), AAV Shuffle 100-1 (SEQ ID NO: 23 of US20160017295), AAV Shuffle 100-3 (SEQ ID NO: 24 of US20160017295), AAV Shuffle 100-7 (SEQ ID NO: 25 of US20160017295), AAV Shuffle 10-2 (SEQ ID NO: 34 of US20160017295), AAV Shuffle 10-6 (SEQ ID NO: 35 of US20160017295), AAV Shuffle 10-8 (SEQ ID NO: 36 of US20160017295), AAV Shuffle 100-2 (SEQ ID NO: 37 of US20160017295), AAV SM 10-1 (SEQ ID NO: 38 of US20160017295), AAV SM 10-8 (SEQ ID NO: 39 of US20160017295), AAV SM 100-3 (SEQ ID NO: 40 of US20160017295), AAV SM 100-10 (SEQ ID NO: 41 of US20160017295), or variants thereof.

In some embodiments, the AAV serotype may be, or have, a sequence as described in United States Patent Publication No. US20150238550, the contents of which are herein incorporated by reference in their entirety, such as, but not limited to, BNP61 AAV (SEQ ID NO: 1 of US20150238550), BNP62 AAV (SEQ ID NO: 3 of US20150238550), BNP63 AAV (SEQ ID NO: 4 of US20150238550), or variants thereof.

In some embodiments, the AAV serotype may be or may have a sequence as described in United States Patent Publication No. US20150315612, the contents of which are herein incorporated by reference in their entirety, such as, but not limited to, AAVrh.50 (SEQ ID NO: 108 of US20150315612), AAVrh.43 (SEQ ID NO: 163 of US20150315612), AAVrh.62 (SEQ ID NO: 114 of US20150315612), AAVrh.48 (SEQ ID NO: 115 of US20150315612), AAVhu.19 (SEQ ID NO: 133 of US20150315612), AAVhu.11 (SEQ ID NO: 153 of US20150315612), AAVhu.53 (SEQ ID NO: 186 of US20150315612), AAV4-8/rh.64 (SEQ ID No: 15 of US20150315612), AAVLG-9/hu.39 (SEQ ID No: 24 of US20150315612), AAV54.5/hu.23 (SEQ ID No: 60 of US20150315612), AAV54.2/hu.22 (SEQ ID No: 67 of US20150315612), AAV54.7/hu.24 (SEQ ID No: 66 of US20150315612), AAV54.1/hu.21 (SEQ ID No: 65 of US20150315612), AAV54.4R/hu.27 (SEQ ID No: 64 of US20150315612), AAV46.2/hu.28 (SEQ ID No: 68 of US20150315612), AAV46.6/hu.29 (SEQ ID No: 69 of US20150315612), AAV128.1/hu.43 (SEQ ID No: 80 of US20150315612), or variants thereof.

In some embodiments, the AAV serotype may be, or have, a sequence as described in International Publication No. WO2015121501, the contents of which are herein incorporated by reference in their entirety, such as, but not limited to, true type AAV (ttAAV) (SEQ ID NO: 2 of WO2015121501), "UPenn AAV10" (SEQ ID NO: 8 of WO2015121501), "Japanese AAV10" (SEQ ID NO: 9 of WO2015121501), or variants thereof.

According to the present invention, AAV capsid serotype selection or use may be from a variety of species. In one embodiment, the AAV may be an avian AAV (AAAV). The AAAV serotype may be, or have, a sequence as described in U.S. Pat. No. 9,238,800, the contents of which are herein incorporated by reference in their entirety, such as, but not limited to, AAAV (SEQ ID NO: 1, 2, 4, 6, 8, 10, 12, and 14 of U.S. Pat. No. 9,238,800), or variants thereof.

In one embodiment, the AAV may be a bovine AAV (BAAV). The BAAV serotype may be, or have, a sequence as described in U.S. Pat. No. 9,193,769, the contents of which are herein incorporated by reference in their entirety, such as, but not limited to, BAAV (SEQ ID NO: 1 and 6 of U.S. Pat. No. 9,193,769), or variants thereof. The BAAV serotype may be or have a sequence as described in U.S. Pat. No. 7,427,396, the contents of which are herein incorporated by reference in their entirety, such as, but not limited to, BAAV (SEQ ID NO: 5 and 6 of U.S. Pat. No. 7,427,396), or variants thereof.

In one embodiment, the AAV may be a caprine AAV. The caprine AAV serotype may be, or have, a sequence as described in U.S. Pat. No. 7,427,396, the contents of which are herein incorporated by reference in their entirety, such as, but not limited to, caprine AAV (SEQ ID NO: 3 of U.S. Pat. No. 7,427,396), or variants thereof.

In other embodiments the AAV may be engineered as a hybrid AAV from two or more parental serotypes. In one embodiment, the AAV may be AAV2G9 which comprises sequences from AAV2 and AAV9. The AAV2G9 AAV serotype may be, or have, a sequence as described in United States Patent Publication No. US20160017005, the contents of which are herein incorporated by reference in its entirety.

In one embodiment, the AAV may be a serotype generated by the AAV9 capsid library with mutations in amino acids 390-627 (VP1 numbering) as described by Pulicherla et al. (Molecular Therapy 19(6):1070-1078 (2011), the contents of which are herein incorporated by reference in their entirety. The serotype and corresponding nucleotide and amino acid substitutions may be, but is not limited to, AAV9.1 (G1594C; D532H), AAV6.2 (T1418A and T1436X; V473D and I479K), AAV9.3 (T1238A; F413Y), AAV9.4 (T1250C and A1617T; F417S), AAV9.5 (A1235G, A1314T, A1642G, C1760T; Q412R, T548A, A587V), AAV9.6 (T1231A; F411I), AAV9.9 (G1203A, G1785T; W595C), AAV9.10 (A1500G, T1676C; M559T), AAV9.11 (A1425T, A1702C, A1769T; T568P, Q590L), AAV9.13 (A1369C, A1720T; N457H, T574S), AAV9.14 (T1340A, T1362C, T1560C, G1713A; L447H), AAV9.16 (A1775T; Q592L), AAV9.24 (T1507C, T1521G; W503R), AAV9.26 (A1337G, A1769C; Y446C, Q590P), AAV9.33 (A1667C; D556A), AAV9.34 (A1534G, C1794T; N512D), AAV9.35 (A1289T, T1450A, C1494T, A1515T, C1794A, G1816A; Q430L, Y484N, N98K, V6061), AAV9.40 (A1694T, E565V), AAV9.41 (A1348T, T1362C; T450S), AAV9.44 (A1684C, A1701T, A1737G; N562H, K567N), AAV9.45 (A1492T, C1804T; N498Y, L602F), AAV9.46 (G1441C, T1525C, T1549G;

G481R, W509R, L517V), 9.47 (G1241A, G1358A, A1669G, C1745T; S414N, G453D, K557E, T5821), AAV9.48 (C1445T, A1736T; P482L, Q579L), AAV9.50 (A1638T, C1683T, T1805A; Q546H, L602H), AAV9.53 (G1301A, A1405C, C1664T, G1811T; R134Q, S469R, A555V, G604V), AAV9.54 (C1531A, T1609A; L5111, L537M), AAV9.55 (T1605A; F535L), AAV9.58 (C1475T, C1579A; T4921, H527N), AAV.59 (T1336C; Y446H), AAV9.61 (A1493T; N4981), AAV9.64 (C1531A, A1617T; L5111), AAV9.65 (C1335T, T1530C, C1568A; A523D), AAV9.68 (C1510A; P504T), AAV9.80 (G1441A; G481R), AAV9.83 (C1402A, A1500T; P468T, E500D), AAV9.87 (T1464C, T1468C; S490P), AAV9.90 (A1196T; Y399F), AAV9.91 (T1316G, A1583T, C1782G, T1806C; L439R, K5281), AAV9.93 (A1273G, A1421G, A1638C, C1712T, G1732A, A1744T, A1832T; S425G, Q474R, Q546H, P571L, G578R, T582S, D611V), AAV9.94 (A1675T; M559L) and AAV9.95 (T1605A; F535L).

In one embodiment, the AAV serotype may be, or may have a sequence as described in International Patent Publication WO2015038958, the contents of which are herein incorporated by reference in their entirety, such as, but not limited to, AAV9 (SEQ ID NO: 2 and 11 of WO2015038958), PHP.B (SEQ ID NO: 8 and 9 of WO2015038958), G2B-13 (SEQ ID NO: 12 of WO2015038958), G2B-26 (SEQ ID NO: 13 of WO2015038958), TH1.1-32 (SEQ ID NO: 14 of WO2015038958), TH1.1-35 (SEQ ID NO: 15 of WO2015038958) or variants thereof. Further, any of the targeting peptides described in WO2015038958, may be inserted into any parent AAV serotype, such as, but not limited to, AAV9.

A wild type AAV genome may be engineered as a viral vector to deliver a polynucleotide of interest into a target cell with improved transduction efficiencies and less immunogenicity. The engineered AAV may be self-complementary (scAAV), wherein, the single strand genomic DNA of AAV and the complementary strand for gene expression are packaged as a single duplex DNA molecule.

The scAAV duplex molecule may be produced by engineering certain components of the AAV genome which promotes the generation of scAAV during the replication process. In general, the viral vector comprises a parvovirus capsid and a self-complementary parvoviral genome encoding a heterologous nucleotide sequence of interest. In one non-limiting example, a self-complementary ssDNA genome comprises in the 5' to 3' direction an ITR, a first complementary sequence, an ITR comprising an engineered Rep binding sequence region, a second complementary sequence, and an ITR. The ssDNA spontaneously folds to form a double stranded hairpin comprising an engineered Rep binding sequence region forming a closed loop at one end of the molecule, a double stranded DNA encoding region, and at least two ITR hairpins at the end of the molecule opposite the closed end.

Recombinant AAVs (rAAVs) can be engineered to comprise the minimal number of components to produce a non-replicative virus designed to deliver a polynucleotide of interest to a target cell. The genome of a rAAV is comprised of ITRs flanking a payload sequence that replaces the wild type Rep and Cap genes. Genes provided in trans for AAV replication comprise Rep and Cap genes expressing the three capsid proteins VP1, VP2, and VP3 and the non-structural protein.

A heterogeneous polynucleotide of interest may be included in an AAV vector for transduction into a target cell. The heterogeneous polynucleotide may be a polynucleotide encoding a protein, a regulatory nucleic acid sequence, a siRNA, a microRNA, a polynucleotide used for vaccine, an antibody, and/or polynucleotides with other biological functions.

Anti-AAV Serotype Neutralizing Antibodies

Humoral Immune Response and Antibodies

Viral infection to a host can stimulate the host's immune defense system to protect the infected host from the virus. One of the immune responses a host activates to defend itself from the attack of a foreign agent is the humoral immune response, which produces antibody-mediated immunity.

As used herein, the term "humoral immunity" refers to the antibody-mediated beta cellular immune system, which is mediated by macromolecules (as opposed to cell-mediated immunity) found in extracellular fluids such as secreted antibodies, complement proteins and certain antimicrobial peptides. In particular, it refers to the antibody mediated immune response of a host.

An antibody, also known as an immunoglobulin (Ig), is a large, Y-shaped glycoprotein produced by plasma cells (B cells) that is used by the immune system to identify and neutralize pathogens such as bacteria and viruses. Typically, an antibody has a high affinity and specificity for an antigen or for an antigenic determinant which is a unique molecule of the pathogen. An antibody is commonly composed of 4 chains (2 heavy and 2 light chains) and is thus tetrameric. An antibody usually has both variable and constant regions whereby the variable regions are mostly responsible for determining the specificity of the antibody and comprise complementarity determining regions (CDRs) from both heavy chains and light chains. The variable region of an antibody, usually the tip of the Y shape structure of the antibody, binds to one particular epitope on an antigen, with precision. Using this binding mechanism, an antibody can tag a pathogen (e.g., an AAV) or an infected cell for attack by other parts of the immune system, or can neutralize its target directly, for example, by blocking a part of a pathogen that is essential for its invasion and survival. The ability of an antibody to communicate with the other components of the immune system is mediated via its Fc region which is located at the base of the "Y". The production of antibodies is the main function of the humoral immune system.

As used herein, the term "specificity" refers to the ability of an immunoglobulin, such as an antibody, to bind preferentially to one antigenic target versus a different antigenic target and does not necessarily imply high affinity.

As used herein, the term "affinity" refers to the degree to which an immunoglobulin, such as an antibody, binds to an antigen so as to shift the equilibrium of antigen and antibody toward the presence of a complex formed by their binding. Thus, where an antigen and antibody are combined in relatively equal concentration, an antibody of high affinity will bind to the available antigen so as to shift the equilibrium toward high concentration of the resulting complex.

As used herein, the term "complementarity determining region" or "CDR" refers to variable regions of either H (heavy) or L (light) chains (also abbreviated as VH and VL, respectively) and contains the amino acid sequences capable of specifically binding to antigenic targets. These CDR regions account for the basic specificity of the antibody for a particular antigenic determinant structure. Such regions are also referred to as "hypervariable regions." The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The variable heavy and light chains of all canonical antibodies each have 3 CDR regions, each non-contiguous with the others (termed L1, L2, L3, H1, H2, H3) for the respective light (L) and heavy (H) chains. The accepted CDR regions have been described by Kabat et al. (*J Immunol.*, 1991, 147(5): 1709-1719).

As used herein, the term "light chain" refers to a component of an antibody from any vertebrate species assigned to one of two clearly distinct types, called kappa (κ) and lambda (λ) based on amino acid sequences of constant domains. Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2.

Naturally occurring antibodies are secreted by cells of the adaptive immune system (B cells), and more specifically, differentiated B cells called plasma cells. Antibodies can occur in two physical forms, a soluble form that is secreted from the cell, and a membrane-bound form that is attached to the surface of a B cell and is referred to as the B cell receptor (BCR). Soluble antibodies are released into the blood and tissue fluids, as well as many secretions to continue to survey for invading microorganisms (e.g., viruses). Antibodies in sera can be detected by an immuno assay such as ELISA.

Antibodies may also be used in the broadest sense and specifically include (but are not limited to) whole antibodies, monoclonal antibodies, polyclonal antibodies, multispecific antibodies (e.g. bispecific antibodies formed from at least two intact antibodies), antibody fragments, diabodies, antibody variants, and antibody-derived binding domains that are part of or associated with other peptides. Antibodies are primarily amino-acid based molecules but may also comprise one or more modifications (including, but not limited to the addition of sugar moieties, fluorescent moieties, chemical tags, etc.).

As used herein, the term "antibody fragment" refers to any portion of an intact antibody. In some embodiments, antibody fragments comprise antigen binding regions from intact antibodies. Examples of antibody fragments may include, but are not limited to Fab, Fab', F(ab')2, and Fv fragments; diabodies; linear antibodies; single-chain antibody molecules; and multispecific antibodies formed from antibody fragments. Papain digestion of antibodies produces two identical antigen-binding fragments, called "Fab" fragments, each with a single antigen-binding site. Also produced is a residual "Fc" fragment, whose name reflects its ability to crystallize readily. Pepsin treatment yields an F(ab')$_2$ fragment that has two antigen-binding sites and is still capable of cross-linking antigens. Kits of the present invention may comprise one or more of these fragments. For the purposes herein, antibodies may comprise a heavy and light variable domain as well as an Fc region.

As used herein, the term "native antibody" refers to a usually heterotetrameric glycoprotein of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain.

As used herein, the term "variable domain" refers to specific antibody domains that differ extensively in sequence among antibodies and are responsible for binding and specificity of each particular antibody for its particular antigen.

As used herein, the term "Fv" refers to antibody fragments comprising complete antigen-recognition and antigen-binding sites. These regions consist of a dimer of one heavy chain and one light chain variable domain in tight, non-covalent association.

As used herein, the term "Single-chain Fv" or "scFv" refers to a fusion protein of $V_H$ and $V_L$ antibody domains, wherein these domains are linked together into a single polypeptide chain. Fv polypeptide linkers may enable scFvs to form desired structures for antigen binding.

As used herein, the term "diabody" refers to a small antibody fragment with two antigen-binding sites. Diabodies comprise a heavy chain variable domain $V_H$ connected to a light chain variable domain $V_L$ in the same polypeptide chain. By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al. (Hollinger, P. et al., *PNAS.* 1993. 90:6444-8) the contents of each of which are incorporated herein by reference in their entirety.

As used herein, the term "monoclonal antibody" refers to an antibody obtained from a population of substantially homogeneous cells (or clones), i.e., the individual antibodies comprising the population are identical and/or bind the same epitope, except for possible variants that may arise during production of the monoclonal antibodies, such variants generally being present in minor amounts. In contrast to polyclonal antibody preparations that typically include different antibodies directed against different determinants (epitopes), each monoclonal antibody is directed against a single determinant on the antigen.

The modifier "monoclonal" indicates the character of the antibody as being obtained from a substantially homogeneous population of antibodies, and is not to be construed as requiring production of the antibody by any particular method. The monoclonal antibodies herein include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies.

As used herein, the term "humanized antibody" refers to a chimeric antibody comprising a minimal portion from one or more non-human (e.g., murine) antibody sources with the remainder derived from one or more human immunoglobulin sources. For the most part, humanized antibodies are human immunoglobulins (recipient antibody) in which residues from the hypervariable region from an antibody of the recipient are replaced by residues from the hypervariable region from an antibody of a non-human species (donor antibody) such as mouse, rat, rabbit or nonhuman primate having the desired specificity, affinity, and/or capacity.

As used herein, the term "antigen" refers to a structure, often a polypeptide or protein, for which an immunoglobulin, such as an antibody, has affinity and specificity. The terms "antigenic determinant," "antigenic target" and "epitope" all refer to a specific binding site on an antigen or on an antigenic structure for which an immunoglobulin, such as an antibody, has specificity and affinity. In the context of the present invention, the capsids of AAV serotypes are the main antigens.

Neutralizing Antibodies

Viral infection can induce an immunogenic reaction of a host to attack the invading pathogens, for example, production of antibodies by activating B cells. Antibody based immunity consists of neutralizing and non-neutralizing antibodies. Non-neutralizing antibodies makeup the greater part of the antibody pool generated during the immune response, but only a small fraction is functional and participates in the clearance of infected cells, sometimes through interaction with other immune cells and/or with the complement system. Neutralizing antibodies specifically bind epitopes crucial for viral function, and interfere with viral infectivity, for example, blocking viral entry to the host cell.

A full spectrum of immune responses to adeno-associated viruses has been assessed to include innate immunity, cytotoxic T-cell (CTL) responses and humoral responses. The pre-existing anti-AAV immunity, in particular, neutralizing antibodies (NAbs) to AAV serotypes has emerged as a challenge for clinical applications of AAV vector mediated gene delivery. Several studies have discussed the prevalence of pre-existing NAbs against the commonly used AAV serotypes (e.g. AAV serotypes 1-9). In addition, the NAbs generated as a result of the therapeutic use of AAV vectors is also problematic. Several studies have shown that the induction of antibodies by natural exposure to AAV early in life can compromise the subsequent use of AAV as a gene therapy vector (Hurlbut et al., *Mol Ther,* 2010, 18(11):1983; Manno et al., *Nat Med,* 2006, 12(3):342; and Wang et al., *Blood,* 2006, 107(5):1810; the contents of each of which are incorporated herein by reference in their entirety).

To date, the prevalence of NAbs against AAV2 is the most common around the world. Almost 70 percent of the human population has neutralizing antibody titers to AAV2 serotype that can interfere with gene therapy using AAV2 vector or vectors derived from AAV2 (Erles K et al., *J Med Virol,* 1999, 59(3):406; Blacklow N R, et al., *J Natl Cancer Inst,* 1968, 40(2):319-27; Boutin S, et al., *Hum Gene Ther,* 2010, 21(6):704; and Calcedo R et al., *J Infect Dis,* 2009, 199(3): 381-390). A comprehensive study conducted by Calcedo et al (Calcedo R et al., *J Infect Dis,* 2009, 199(3): 381-390) provides anti-AAV antibodies against several AAV serotypes in several countries and continents. In this study, the prevalence of NAbs against AAV2 is the highest in all populations tested, as compared to NAbs against other tested AAV serotypes.

Interestingly, it is also suggested that the prevalence of anti-AAV antibodies is age dependent. Calcedo et al (Calcedo et al., *Clin. Vaccine Immunol.,* 2011, 18; 1586-1588) demonstrated that anti-AAV antibodies can be detected at birth and appear to decrease over early life. Of the immunoglobulin subclasses, IgG1 is usually the highest. Some individuals have a higher IgG2/3 level (Murphy et al., *J Med. Virol.,* 2009, 81: 65-74).

Neutralizing antibodies (NAbs) bind and inhibit AAV transduction of target cells through several mechanisms. AAV neutralizing antibodies have been the focus of many studies because of their significant deleterious effect on the efficacy of AAV-mediated gene therapy. Recent studies have shown that AAV binding antibodies may also have an impact on AAV vector distribution and safety (Klasse et al., *J Gen Virol,* 2002, 83(Pt 9):2091; and Wang et al., *Hum Gene Ther,* 2011, 22(11):1389; the contents of each of which are incorporated herein by reference in their entirety).

Neutralizing antibodies (NAbs), as used herein, refer to antibodies that defend a cell from an antigen or infectious agent by inhibiting or neutralizing any effect it has biologically. In general, an antibody binds to an antigen and signals to white blood cells that this antigen has been targeted (i.e. flagged). The flagged antigen is processed and consequently destroyed, while neutralizing antibodies neutralize the biological effect of the antigen itself. A NAb may be a broadly neutralizing antibody (bNAb) that works on multiple serotypes of a virus, or a specific NAb that specifically recognizes one serotype.

"Neutralization" to viruses, in particular to AAV capsids and AAV serotypes, is defined here as the abrogation of virus infectivity in vitro or in vivo by the binding of a neutralizing compound (e.g., antibody) to the virus serotype and/or the binding of a cell surface and preventing the interaction with AAV. In the context of the present invention, the definition does not include the blocking of infection by a neutralizing compound that binds to a receptor for the virus on the (host) cell surface. The neutralization ability of an antibody is usually measured via the expression of a reporter gene such as luciferase or GFP. In order to determine and compare the activity of a neutralizing antibody, the antibody tested should display a neutralizing activity of 50% or more in one of the neutralization assays described in the present invention.

In some examples, neutralizing capacity is determined by measuring the activity of a reporter gene product (e.g., luciferase, GFP). The neutralizing capacity of an antibody to a specific AAV serotype may be at least 50%, e.g., at least 55%, 60%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99%.

Detection of pre-existing neutralizing antibodies to AAV capsids and AAV serotypes in AAV gene delivery is critical for developing appropriate approaches on how to overcome the challenge posited by these antecedent antibodies. The use of different/alternative AAV capsids and AAV serotypes, to which lower titers or absences of neutralizing antibodies are detected in a patient or a group of patients, may overcome this challenge.

Viral Neutralization Assays

Neutralization Assay

Antibody detection and assessment is usually measured using an immunological assay which is based on antibody-antigen (e.g., a targeted virus or viral antigen) interaction. As used herein, the term "immunological assay" refers to any assay comprising the use of antibodies for one or more means of detection and/or measurement. An immunoassay takes advantage of the specific binding of antibody to its antigen. The antibodies have a high affinity for the antigen of interest (e.g., the AAV capsid) to allow a very high proportion of the antigen to bind to the antibody in order to ensure that the assay has adequate sensitivity. Immunological assays may include enzyme immunoassay (EIA), radioimmunoassay (IA), which uses radioactive isotopes, fluoroimmunoassay (FIA) which uses fluorescent materials, chemiluminescent immunoassay (CLIA) which uses chemiluminescent materials and counting immunoassay (CIA) which employs particle-counting techniques, other modified assays such as western blot, immunohistochemistry (IHC) and agglutination. One of the most common enzyme immunoassays is enzyme-linked immunosorbent assay (ELISA).

A neutralization assay is a specific immunoassay adapted for quantifying the titer of neutralizing antibody of a virus. In general, a test sample. e.g., serum sample and a solution of antibody, is diluted and mixed with a viral suspension. The mixture is added to a confluent monolayer of host cells after being incubated to allow the neutralizing antibody to react with the virus. The virus infectivity to the host cells is quantitated. The most common assay is called plaque reduction neutralization test (PRNT). In this assay, the concentration of plaque forming units is estimated by the number of plaques (regions of infected cells) formed in the culture after a period of incubation (typically a few days). Depending on the virus, the plaque forming units are measured by microscopic observation, fluorescent antibodies or specific dyes that react with infected cells. The concentration of serum to reduce the number of plaques by 50% compared to the serum free virus gives the measure of how much antibody is present or how effective it is.

Variations on the plaque assay include the fluorescent-focus assay and the infectious center assay. In infectious center assay, the infected cells are suspended, counted, and plated onto monolayers of susceptible cells. The number of plaques which form in the indicator cells provides a measure of the number of virus-infected cells in the original culture. In contrast, the fluorescent-focus assay does not rely on the induction of cell death (e.g., the infected cells), rather the use of antibody staining methods to detect virus antigens within infected cells in the monolayer. These infected cells are then visualized using a fluorescent label on the virus-specific antibody, and counted (Kraus et al., *J. Clin. Microbiol.* 2007, 45: 3777). These assays are helpful in titering viruses that do not kill their host cells.

The plaque reduction neutralization test is currently considered as a standard assay for detecting and measuring antibodies that can neutralize the viruses that cause many diseases. It is widely used for studying antibody response to anti-viral defense and the efficacy of anti-viral vaccines. It has a higher sensitivity than other immunoassays such as EIA.

A microneutralization method using enzyme-linked immunosorption was developed. In this assay, the level of virus infectivity with or without tested sera is estimated by measuring nuclear protein (NP) of virus expressed in the target cells by staining the permeabilized fixed cells with the NP-specific monoclonal Ab labeled with horseradish peroxidase (HRP) (Rowe et al. *J. Clin. Microbiol.* 1999, 37: 937-943). Another direct microneutralization (MN) assay is also practiced in the field. In the MN assay, a confluent layer of target cells is infected with a diluted virus culture either in the presence or absence of a test serum/sera or antibody solution(s) of interest, and the rate of virus reproduction is evaluated by measuring released virus concentrations with a standard hemagglutination assay (HA) technique.

Other methods, including the detection of viral nucleic acids are used to measure viral infectivity after antibody incubation. One of the most widely used methods for detection of viral nucleic acids is the polymerase chain reaction (PCR).

Virus neutralization assays are also widely used for detecting and measuring neutralizing antibodies to AAVs. Several assays have been proposed in the art to detect neutralizing antibodies to different AAV serotypes. Some of these methods detect total binding antibodies to AAV capsids and others detect antibodies that neutralize transduction of AAV vectors in vitro or in vivo. Early methods to evaluate total antibody responses to AAV vector included ELISA and Western blot (Blacklow et al., *J Natl Cancer Inst,* 1968, 40(2):319; Mayor et al., *Am J Obstet Gynecol,* 1976, 126(1):100; and Parks et al., *Infect Immun,* 1970; 2(6):716). ELISAs can detect the total amount of antibody in sera that bind to an AAV serotype, including non-neutralizing antibodies and neutralizing antibodies (Chirmule et al., *Gene Ther.*, 1999, 6: 1574-1583); Erles et al., *J Med. Virol.*, 1999, 59: 406-411; and Boutin et al., *Hum. Gene Ther.*, 2010, 21: 704-712). Though ELISA-based assays are easy to set up and give a relatively sensitive measurement of total antibodies binding to AAV, the results do not necessarily reflect their neutralizing activity.

The neutralization of anti-AAV antibodies have been evaluated mainly using cell based in vitro neutralization assays to detect anti-AAV neutralizing antibodies. Currently the standard neutralization assay includes in vitro transduction inhibition assay. The assay is usually carried out in a 48- or a 96-well plate format allowing a high throughput sample analysis. Specific cell lines have been used for this assay, such as, but not limited to: HeLa, 2V6.11, 293, and Huh7 (Calcedo et al., *J. of Infectious Diseases,* 2009; 199: 381-390; Rapti et al., *Mol Ther,* 2011, 19(11):2084; and Veron et al., *J Immunol,* 2012, 188(12): 6418).

All these assays, ELISAs or in vitro viral neutralization assays, involve detecting the infectivity of AAV to the host cells with the use of helper adenoviruses. Chirmule et al (*Gene Ther.*, 1999, 6: 1574-1583), in his western blot and ELISA detection of anti-AAV antibodies, produced recombinant AAV2/LacZ vector, by plasmid transfections in 293 cells infected with E1-deleted recombinant adenovirus based on serotype 5 (Ad) that express β-galactosidase. An 84-31 line, a subclone of 293 cells that stably expresses E4 of Ad that renders it permissive for AAV transduction, was used for analyzing neutralizing antibody titers in Chirmule's viral neutralization assays.

Calcedo et al. (*J. of Infectious Diseases,* 2009; 199: 381-390), in his comprehensive study of the prevalence of neutralizing antibodies to AAVs use adenovirus helper plasmid to produce AAV vectors with different combinations of serotypic capsids. In his assay to detect neutralization of antibody titers, AAV vector, mixed with sera to be tested, was transduced to Huh7 cells that have been infected previously with Human adenovirus serotype 5 (HAdv 5). More recently, Meliani et al. (Meliani et al., *Human Gene Therapy Methods,* 2015, 26: 45-53) reported an assay using an in vitro luciferase reporter system. Transduction of AAV-luciferase vector was carried out using 2V6.11 cells which were induced to express the adenoviral gene E4.

In summary, these assays include procedures of 1): preparation of an AAV vector, or an AAV vector expressing a reporter gene (e.g., luciferase); 2): preparation of a cell culture that is induced to express adenoviral components (e.g., adenoviral gene E4), or induced with adenovirus; 3): preparation of a mix of the AAV vector with serial dilutions of the test and control samples (e.g., sera and antibody solutions); 4): transduction of the cell culture with the mix from 3) and incubation of the transduced cells; and 5): analysis of the infectivity of AAV vector in the presence of the test sera, as compared to the control sample. The analysis could be done by measuring the expression/activity of the reporter gene using cell lysis.

In addition to the safety concerns raised by the use of disease-causing adenovirus during the assay, neutralizing antibody titers are usually analyzed by assessing the ability of serum antibody to inhibit transduction of Adenovirus and AAVs. Meanwhile, measurement of AAV infection using cell lysis can yield inconsistent results due to the lysing process.

The present invention provides an optimized neutralization assay for the detection of neutralizing antibodies against AAV. The present assay avoids the use of adenovirus during the assay and the detection of antibodies specific to adenovirus. Furthermore, the present assay directly detects a fluorescent signal from transduced live cells without lysis, which increases the consistency of the assay.

AAV Neutralization Assays of the Present Invention

In accordance with the present invention, methods for detecting neutralizing antibodies against AAV in a sample, comprise: a): production of an AAV vector including a particular serotypic capsid, wherein said AAV vector may contain a GFP tag or the equivalent; b): preparation of a cell culture of choice that is suitable for the assay; c): preparation of a dilution cascade of test samples and controls; d): preparation of the mix of the AAV vector with the diluted test samples and controls; e): transduction of the cell from step b) with the mixture of d) and incubation; and f): harvesting the cells from step e) and measuring fluorescence positive target cells.

In some embodiments of the present invention, the optimized assay comprises the following steps, which are also shown in FIG. 1:

Step 1: A construct of an AAV vector used for the assay is produced. The AAV vector may include wild type or mutated capsids from a specific AAV serotype and a GFP tag. The AAV particles are diluted to certain titers. In some aspects, AAV particles may be stocked at −80° C. for later use.

Step 2: Serum or other bodily fluid sample(s) from a patient is collected, heat inactivated (56° C., for 30 minutes), and diluted in serial concentration using a medium, for example, a DMEM culture medium.

Step 3: A cell culture at a certain cell density (e.g., a density to achieve 70-100% confluency if adherent cells are used and equivalent numbers if suspension cells are used) is prepared prior to the neutralization assay. The cell culture may be a cell line suitable for viral transduction, for example, HELA cells.

Step 4: The serial dilutions of serum samples from the patient and control sera are added to AAV viral particles at a titer pre-determined to yield detectable infectivity; the sera/virus mixture is incubated at 37° C. for 1 hour.

Step 5: The mix of AAV vector and serum samples is added to the cell culture. The cell is cultured 37° C. in a 5% humidified $CO_2$ atmosphere for 2 to 7 days.

Step 6: At the end of incubation, the cells are harvested and the GFP positive cells are counted accompanied by detecting the intensity of the GFP signal in each of those cells. In one embodiment, the counted GFP positive cells are used to determine the neutralizing capacity of the test serum sample, such as calculating anti-AAV neutralizing antibody titer in the test sample.

In some embodiments, any cell lines to which an AAV vector is tropic may be used for the present assay. As non-limiting examples, AAV permissive cells may be Huh7 cells, human cancer cell line HeLa cells, Hela S3 cells, murine hepatoma Hepa1-6 cells, HEK293, human hepatoma cells HepG2 and IMY-N9 (a cell line derived from fusing human hepatocytes and HepG2 cells). In one example, Hela S3 cells are used for the present assay.

In accordance with the present invention, any culture media capable of supporting cell growth and replication of AAV vectors may be used. Other factors that improve viral replication or infectivity may be used in various embodiments of the present invention.

In some embodiments, the bodily fluid may be collected from a patient in need of an AAV mediated gene therapy, a patient after a dose of AAV gene therapy, or a subject suspected of exposure to AAV or a composition based on AAV.

Not wishing to be bound by any theory, the present assay is based on the ability of the anti-AAV antibody to block entry of the AAV into a host cell. Therefore, the helper adenovirus or its components, which are used for assisting the replication of AAV, can be omitted in the present assay. An advantage of such an assay is to allow the neutralization test to be performed without extensive safety precautions. Such optimization is important in a preclinical setting such as in an AAV gene therapy study. The present assay may be used preclinically, as well as clinically after validation. Additionally, the present assay avoids detecting the presence of anti-adenovirus antibodies which may be produced due to the use of the helper adenovirus and therefore may be more precise. As a non-limiting example, the assay is of clinically approved quality.

In some embodiments, the AAV vectors may be GFP tagged. variants and derivatives of GFP may also be used to tag AAV vectors, including, but not limited to, enhanced GFP (EGFP), blue fluorescent protein (EBFP, EBFP2, Azurite, mKalama1), cyan fluorescent protein (ECFP, Cerulean, CyPet, mTurquoise2), and yellow fluorescent protein derivatives (YFP, Citrine, Venus, YPet).

In some embodiments, cells harvested from the transduction assay, after washing, are directly used for measuring GFP signal. The cell lysis procedure, as used in traditional assays, may be skipped. The number of GFP positive cells which are transduced by the AAV-GFP vector, is counted directly and compared to controls.

In some embodiments, measuring of fluorescence may be through the use of a flow cytometer. Flow cytometry techniques have been used in viral neutralization assays. Several recent studies have proposed that viral infection of target cells in the presence or absence of a test serum/sera or antibody solution(s) can be monitored by flow cytometric methods to detect the fluorescent tags (Klingen et al., *J. Virol.* 2008, 82: 237; and Collins & Buchholz, *J. Virol. Meth.* 2005, 128: 192-197).

In some embodiments, dilutions of a test serum sample, which defines the sensitivity of the assay, may vary between ranges from 1:2 to 1:1,000,000. As a non-limiting example, the range may be 1:2 to 1:100. As another non-limiting example, the range may be 1:2 to 1:1,000. As yet another non-limiting example, the range may be 1:2 to 1:10,000.

In some embodiments, the present methods, optimized as routine laboratory tests, may be high-throughput, screening multiple samples simultaneously, for example, 50-500 samples.

Applications

Methods of the present invention provide highly desirable assays which eliminate the need for special laboratory facilities and techniques, and provide notably quicker turnaround time in order to assess the AAV neutralizing antibody titers in serum.

The methods described herein have a variety of uses, including, but not limited to, quantitative assessment of AAV neutralizing antibodies in a biological sample without the necessity of conducting an AAV infection assay with the Adv helper virus, a tedious (two to seven day), complex, and biohazardous procedure.

In one aspect of the present invention, the present assays and methods may be used to evaluate a patient who is in need of a gene therapy, to determine whether said patient is absent of pre-existing neutralization antibodies against the AAV capsids used for the gene therapy.

In another aspect of the present invention, the present assays and methods may be used to assess the prevalence of pre-existing neutralization antibodies against AAV capsids and/or AAV serotypes in a population; which may be used to design AAV vectors with different serotypic capsids for gene delivery.

In a third aspect of the present invention, the present assays and methods may be used to evaluate repeat administration of AAV mediated gene therapy. Additionally, the assays may be used to assist in monitoring/adjusting AAV mediated gene therapy, including, but not limited to, dose adjustment that may be used to overcome pre-existing immunity in a patient; assessment of difference in administration routes, and the timing of successive administrations.

Definitions

Unless defined otherwise, all technical and scientific terms used herein have the same meaning as commonly understood by one of ordinary skill in the art to which this invention belongs. Furthermore, the following terms shall have the definitions set out below.

Assay: As used herein, the term "assay" refers to a method of laboratory analysis, and may be used interchangeably with the term "method."

Hela S3 cells: HeLa S3 is one of the mutants of the original HeLa cell that has different growth requirements. HeLa S3, is able to grow larger and in spherical colonies. S3 can form colonies with a lower concentration of human serum in media, compared to that of normal HeLa cells, and is perfectly suited for fetal calf serum.

In vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In vivo: As used herein, the term "in vivo" refers to events that occur within an organism (e.g., animal, plant, or microbe or cell or tissue thereof).

Neutralization assay: also called "serum virus neutralization assay": as used herein, the term "neutralization assay" and "serum virus neutralization assay" refers to a serological test to detect the presence of systemic antibodies that may prevent infectivity of a virus. Such assays may also qualitatively or quantitatively discern the binding capacity (e.g., magnitude) or efficiency of the antibodies to neutralize a target.

MOI (multiplicity of infection): As used herein, the term "MOI" refers to the ratio of AAV vectors to the transduced cells. For example, when referring to a group of cells inoculated with virus particles, the multiplicity of infection or MOI is the ratio of the number of virus particles to the number of target cells present in a defined space (e.g., a culture plate well).

Patient: As used herein, the term "patient" includes human and other mammalian subjects that receive either prophylactic or therapeutic treatment.

Polynucleotide: As used herein, the term "polynucleotide" refers to a polymeric form of nucleotides of any length, either ribonucleotides or deoxyribonucleotides, and includes both double- and single-stranded DNA and RNA. A polynucleotide may include nucleotide sequences having different functions, such as coding regions, and non-coding regions such as regulatory sequences (e.g., promoters or transcriptional terminators). A polynucleotide can be obtained directly from a natural source, or can be prepared with the aid of recombinant, enzymatic, or chemical techniques. A polynucleotide can be linear or circular in topology. A polynucleotide can be, for example, a portion of a vector, such as an expression or cloning vector, or a fragment.

Subject: As used herein, the term "subject" includes any human or non-human animal.

Vector: As used herein, the term "vector" refers to any molecule or moiety which transports, transduces or otherwise acts as a carrier of a heterologous molecule such as the polynucleotides. A "viral vector" is a vector which comprises one or more polynucleotide regions encoding or comprising a molecule of interest, e.g., a transgene, a polynucleotide encoding a polypeptide or multi-polypeptide or a modulatory nucleic acid. In the context of the present invention, the viral vectors may be produced recombinantly and may be based on adeno-associated virus (AAV) parent or reference sequences.

Equivalents and Scope

Those skilled in the art will recognize, or be able to ascertain using no more than routine experimentation, many equivalents to the specific embodiments in accordance with the invention described herein. The scope of the present invention is not intended to be limited to the above description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any antibiotic, therapeutic or active ingredient; any method of production; any method of use;

etc.) can be excluded from any one or more claims, for any reason, whether or not related to the existence of prior art.

It is to be understood that the words which have been used are words of description rather than limitation, and that changes may be made within the purview of the appended claims without departing from the true scope and spirit of the invention in its broader aspects.

EXAMPLES

Example 1: Measurement of AAV-DJ-Binding Immunoglobulin Through In Vitro Neutralization Assay Protocol of AAV Vector Neutralization Assay First, HeLa S3 cells were seeded at 10,000/well in a 96-well plate; maintained in Dulbecco's modified Eagle medium (DMEM) supplemented with 10% FBS (fetal bovine serum); and cultured overnight to reach a density of about 20,000/well.

Next, AAV-DJ vectors containing the polynucleotide sequence encoding GFP (AAV-DJ-GFP) were titered across $10^6$, $10^5$, $10^4$, and $10^3$ MOI in serum-free DMEM. The serial titer $10^6$ indicates $10^6$ genomic copies of virus.

Viral titrations of AAV-DJ vectors containing the polynucleotide sequence encoding GFP (AAV-DJ-GFP) were added to the HeLa S3 cell culture at MOIs of $10^6$, $10^5$, $10^4$ or $10^3$ in each plate, as non-neutralized controls for staining intensity.

Serum samples collected from non-human primate (NHP) were heated at 56° C. for 30 minutes and then cooled by placing them on ice. Next, NHP serum samples were diluted serially at ¼; ¹⁄₁₆; ¹⁄₆₄ and ¹⁄₂₅₆ in serum-free DMEM.

Serum samples collected from human volunteers with or without IgG depletion from the sample, as well as NHP serum samples were diluted and prepared at the same dilutions as noted above (¼; ¹⁄₁₆, ¹⁄₆₄ and ¹⁄₂₅₆). Serum samples were heated at 56° C. for 30 min and cooled on ice prior to dilution.

AAV-DJ-GFP vectors at MOIs of $10^5$, or $10^4$ were mixed and incubated with heat-inactivated, serial diluted non-human primate and human volunteer serum samples in DMEM supplemented with 10% FBS for 1 hour at 37° C.

Subsequently, the serum-AAV vector mixtures from were added to 96-well plates seeded with HeLa S3 cells and incubated for 72 hours at 37° C.

After 72 hours of incubation/transduction, cells from each well were trypsinized and collected for flow cytometry analysis and microscopic imaging.

The Mean Fluorescent Intensity (MFI) was measured and compared.

Flow Cytometry Outcomes

Viral titration of control AAV-DJ vectors without neutralization (as shown in Step 3) were analyzed by flow cytometry and measure for MFI in each condition (Table 1). Cells transduced with AAV-DJ-GFP vectors were imaged.

TABLE 1

MFI of non-neutralized AAV-DJ-GFPs

| AAV Genomic Copies | % Positive Cells | MFI |
|---|---|---|
| $10^6$ | 98 | 540,000 |
| $10^5$ | 96 | 298,000 |
| $10^4$ | 79 | 118,000 |
| $10^3$ | 0.4 | 4,300 |

Neutralization Assessed at $10^5$ AAV-DJ-GFP/Well

As discussed in steps 4-7, human serum samples with or without IgG depletion and NHP serum samples in serial dilutions (from ¼ to ¹⁄₂₅₆) were incubated with diluted AAV-DJ-GFP vectors at $10^5$ or $10^4$ MOIs. The serum and vector mixture was used to transduce HELA S3 cell cultures as described. MFI measurement suggests that for AAV-DJ, an MOI of $10^4$ as higher MOI oversaturates the assay with AAV viral particles and does not allow quantitative assessment of neutralization (Tables 2 and 3).

TABLE 2

MFI of AAV-DJ-GFP ($10^5$) neutralized with serum samples

| Serum Sample | | % Positive | |
|---|---|---|---|
| Serum | Dilution | Cells | MFI |
| Human serum | ¼ | >99 | $4.6 \times 10^5$ |
| | ¹⁄₁₆ | >99 | $5.3 \times 10^5$ |
| | ¹⁄₆₄ | >99 | $5.9 \times 10^5$ |
| | ¹⁄₂₅₆ | >99 | $5.1 \times 10^5$ |
| Human serum with depleted IgG | ¼ | >99 | $8.2 \times 10^5$ |
| | ¹⁄₁₆ | >99 | $8.1 \times 10^5$ |
| | ¹⁄₆₄ | >99 | $7.0 \times 10^5$ |
| | ¹⁄₂₅₆ | >99 | $6.1 \times 10^5$ |
| NHP serum | ¼ | 90 | $2.1 \times 10^5$ |
| | ¹⁄₁₆ | >99 | $6.9 \times 10^5$ |
| | ¹⁄₆₄ | >99 | $8.2 \times 10^5$ |
| | ¹⁄₂₅₆ | >99 | $9.0 \times 10^5$ |

Neutralization Assessed at $10^4$ AAV-DJ-GFP/Well

TABLE 3

MFI of AAV-DJ-GFP ($10^4$) neutralized with serum samples

| Serum Sample | | % Positive | |
|---|---|---|---|
| Serum | Dilution | Cells | MFI |
| Human serum | ¼ | 18 | $0.06 \times 10^5$ |
| | ¹⁄₁₆ | 74 | $0.5 \times 10^5$ |
| | ¹⁄₆₄ | 91 | $12.3 \times 10^5$ |
| | ¹⁄₂₅₆ | 98 | $17.2 \times 10^5$ |
| Human serum with depleted IgG | ¼ | 98 | $17.8 \times 10^5$ |
| | ¹⁄₁₆ | 99 | $32.7 \times 10^5$ |
| | ¹⁄₆₄ | 99 | $31.6 \times 10^5$ |
| | ¹⁄₂₅₆ | 99 | $29.2 \times 10^5$ |
| NHP serum | ¼ | 1 | $0.3 \times 10^5$ |
| | ¹⁄₁₆ | 2 | $0.4 \times 10^5$ |
| | ¹⁄₆₄ | 39 | $2.3 \times 10^5$ |
| | ¹⁄₂₅₆ | 84 | $12.6 \times 10^5$ |

Following the protocol described above, several samples were assessed for antibody neutralization by measuring the preclusion of viral transduction of AAV-DJ-GFP at $10^4$ MOI. Several NHP serum samples were tested as shown in Table 4.

TABLE 4

Serum neutralization assessment at AAV-DJ-GFP ($10^4$ MOI)

| Serum Sample | | % Positive | |
|---|---|---|---|
| Serum | Dilution | Cells | MFI |
| C62087 | ¼ | <1 | $0.03 \times 10^5$ |
| | ¹⁄₁₆ | <1 | $0.03 \times 10^5$ |
| | ¹⁄₆₄ | <1 | $0.04 \times 10^5$ |
| | ¹⁄₂₅₆ | 3 | $0.04 \times 10^5$ |

TABLE 4-continued

Serum neutralization assessment at AAV-DJ-GFP ($10^4$ MOI)

| Serum Sample | | % Positive | |
|---|---|---|---|
| Serum | Dilution | Cells | MFI |
| C62128 | 1/4 | 65 | $0.52 \times 10^5$ |
|  | 1/16 | 82 | $14.6 \times 10^5$ |
|  | 1/64 | 98 | $23.8 \times 10^5$ |
|  | 1/256 | 99 | $24.1 \times 10^5$ |
| C62142 | 1/4 | 92 | $24.8 \times 10^5$ |
|  | 1/16 | 99 | $33.7 \times 10^5$ |
|  | 1/64 | 99 | $34.9 \times 10^5$ |
|  | 1/256 | 99 | $28.2 \times 10^5$ |
| C62162 | 1/4 | 3 | $0.08 \times 10^5$ |
|  | 1/16 | 1 | $0.07 \times 10^5$ |
|  | 1/64 | 3 | $0.07 \times 10^5$ |
|  | 1/256 | 16 | $0.12 \times 10^5$ |
| C62185 | 1/4 | 5 | $0.07 \times 10^5$ |
|  | 1/16 | 29 | $0.22 \times 10^5$ |
|  | 1/64 | 77 | $1.02 \times 10^5$ |
|  | 1/256 | 98 | $1.80 \times 10^5$ |
| C62199 | 1/4 | 94 | $2.42 \times 10^5$ |
|  | 1/16 | 99 | $3.74 \times 10^5$ |
|  | 1/64 | 99 | $3.51 \times 10^5$ |
|  | 1/256 | 99 | $2.28 \times 10^5$ |
| C62202 | 1/4 | 59 | $5.1 \times 10^5$ |
|  | 1/16 | 92 | $17.5 \times 10^5$ |
|  | 1/64 | 98 | $26.0 \times 10^5$ |
|  | 1/256 | 99 | $26.4 \times 10^5$ |
| C62217 | 1/4 | 1 | $0.04 \times 10^5$ |
|  | 1/16 | 1 | $0.03 \times 10^5$ |
|  | 1/64 | 1 | $0.03 \times 10^5$ |
|  | 1/256 | 20 | $0.08 \times 10^5$ |

These outcomes from the in vitro AAV-DJ neutralization assay in Example 1 concludes that no neutralizing antibodies were detected in samples C62199 and C62142; and that the neutralizing antibody titer in C62087 is more than 1/256 (>1/256). The other samples contained anti-AAV antibody titers at 1/4 (C62202 and C62128), 1/16 (C62185), or 1/256 (C62217 and C62162). By running these assays, we also decided to later only use % transduction inhibition to assess neutralization, while preserving MFI values in determining the appropriate MOI for each AAV capsid and viral serotype.

The results from this initial assessment of neutralizing antibodies in serum samples using the present AAV-DJ-GFP neutralization assay in vitro indicate that the present assay can consistently rank the samples across viral concentrations and exhibit a wide range of detection, for example, >1/64 titration.

Example 2: AAV-DJ Neutralization Assay In Vitro: Serial Samples

To test serial dilutions of serum samples for AAV-DJ neutralization, a similar protocol was used. Hela S3 cells were seeded at 10,000/well in a 96-well plate; maintained in Dulbecco's modified Eagle medium (DMEM) supplemented with 10% FBS (fetal bovine serum); and cultured overnight to reach a density of about 20,000/well. Four NHP serum samples previously tested for neutralizing antibodies to AAV-DJ vector, which were drawn from 4 animals (i.e., C62199, C62202, C64882 and C62185) prior to doing (p), or at day 3 (D3) after dosing, or at necropsy (n), were tested in the present assays. These NHP serum samples were diluted serially at 1/4, 1/16, 1/64, 1/256, 1/1024, 1/4096, and 1/16,384. Additionally, human serum with depleted IgG, NHP serum from commercial sources, as well as two samples: C62142 with a titer of 1/4 or less and C62217 with a titer of 1/256, were used as controls and measure standards. Tested serum samples were mixed with AAV-DJ-GFP vectors at a MOI of $10^4$/well and incubated for 1 hour at 37° C.; and then the serum-AAV mixture was added to HELA S3 cell culture and incubated for 72 hours at 37° C. Transduced cells were then harvested and analyzed by flow cytometry. Data analysis was performed blindly.

The GFP positive cells were quantified and compared for different samples (Table 5).

TABLE 5

Percentage of GFP positive cells quantification

| | Dilution (data given as %) | | | | | | |
|---|---|---|---|---|---|---|---|
| Serum samples | 1/4 | 1/16 | 1/64 | 1/256 | 1/1024 | 1/4096 | 1/16384 |
| Human serum without IgG | 52.5 | 77.8 | 90.2 | 90.2 | 91.9 | 91.6 | 91.5 |
| NHP serum | 0.5 | 0.8 | 49 | 86.3 | 90.4 | 92.4 | 90.2 |
| C62142 | 75.3 | 86.9 | 91.1 | 91.9 | 90.6 | 92.6 | 89.9 |
| C62217 | 0.2 | 0.2 | 66.1 | 66.1 | 87.6 | 92.2 | 90.8 |
| C62199 p | 557.8 | 80.0 | 88.1 | 82.3 | 83.4 | 89.2 | 85.0 |
| D3 | 61.7 | 76.6 | 83.8 | 82.7 | 87.1 | 87.2 | 85.9 |
| n | 0.4 | 0.3 | 0 | 0.3 | 0.4 | 0.6 | 2.5 |
| C62202 p | 1.3 | 13.5 | 67.7 | 84.2 | 84.3 | 83.6 | 88.7 |
| D3 | 0.2 | 20.2 | 81.6 | 79.5 | 88.2 | 88.6 | 80.9 |
| n | 18.2 | 0.3 | 0.7 | 0.7 | 0.8 | 1.0 | 9.5 |
| C64882 p | 50 | 85.4 | 96.3 | 96.5 | 97.0 | 96.5 | 95.8 |
| D3 | 62.6 | 92.2 | 97.3 | 95.0 | 96.5 | 97.3 | 96.1 |
| n | 0.4 | 0.4 | 0.5 | 1.1 | 21.4 | 90.6 | 96.4 |
| C62185 p | 28.5 | 87.2 | 96.2 | 96.2 | 97.4 | 97.6 | 97.1 |
| D3 | 9.3 | 63.5 | 95.8 | 97.3 | 96.2 | 97.7 | 97.0 |
| n | 0.2 | 0.7 | 0.2 | 0.4 | 4.5 | 53.1 | 93.1 |

Example 3: AAV1 Neutralization Assay In Vitro: Serial Samples

In this test, Hela S3 cells were seeded at 10,000/well in a 96-well plate; maintained in Dulbecco's modified Eagle medium (DMEM) supplemented with 10% FBS (fetal bovine serum); and cultured overnight to reach a density of about 20,000/well. NHP serum samples previously tested for neutralizing antibodies to AAV6 vector, which were drawn from 4 animals (i.e., C62104, C62105, C62109 and C62564) prior to dosing with AAV6 (p), or at day 3 (D3) after dosing, or at necropsy at day 43 (N), were tested in the present assay. These NHP serum samples were diluted serially at 1/4, 1/16, 1/64, 1/256, 1/1024, 1/4096, and 1/16,384. Additionally, human serum without IgG, NHP serum from commercial sources, as well as two samples: C62142 with the titer of 1/4 or less for AAV-DJ, and C64882 with the titer of 1/1024 for AAV-DJ, were used as controls and measure standards. Tested serum samples were mixed with AAV1-GFP vectors at a MOI of $10^4$/well and incubated for 1 hour at 37° C.; and then the serum-AAV mixture was added to HELA S3 cell culture and incubated for 72 hours at 37° C. Transduced cells were then harvested and analyzed by flow cytometry. Data analysis was performed blindly The AAV1-GFP positive cells which are not inhibited by antibodies were quantified and compared for different samples (Table 6).

TABLE 6

Percentage of AAV1-GFP positive cells quantification

| Serum samples | | 1/4 | 1/16 | 1/64 | 1/256 | 1/1024 | 1/4096 | 1/16384 |
|---|---|---|---|---|---|---|---|---|
| Human serum without IgG | | 1.5 | 3.8 | 17.4 | 28.8 | 31.9 | 37.1 | 35.6 |
| NHP serum | | 0.9 | 1.1 | 1.2 | 3.6 | 21.7 | 33.3 | 34.2 |
| C62142 | p | 4.8 | 25.5 | 37.0 | 34.1 | 35.5 | 38.4 | 39.1 |
| C64882 | D43 | 1.0 | 0.9 | 1.1 | 1.6 | 8.1 | 25.3 | 31.7 |
| C62104 | p | 3.9 | 41.0 | 41.4 | 31.9 | 33.8 | 37.6 | 33.2 |
| | D3 | 18.2 | 45.6 | 44.6 | 39.0 | 34.1 | 35.6 | 39.4 |
| | N | 0.7 | 1.1 | 1.0 | 1.3 | 1.8 | 2.5 | 2.0 |
| C62109 | p | 3.9 | 41.0 | 41.4 | 31.9 | 33.8 | 37.6 | 33.2 |
| | D3 | 18.2 | 45.6 | 44.6 | 39.0 | 34.1 | 35.6 | 39.4 |
| | N | 0.7 | 1.1 | 1.0 | 1.3 | 1.8 | 2.5 | 2.0 |
| C62564 | p | 1.0 | 3.7 | 21.5 | 29.2 | 32.2 | 37.0 | 37.9 |
| | D3 | 8.4 | 44.3 | 44.7 | 36.1 | 36.3 | 38.1 | 36.5 |
| | N | 0.8 | 0.9 | 0.7 | 1.3 | 1.7 | 1.0 | 2.1 |

Similar to the results observed in the AAV-DJ neutralization assay, the AAV1 neutralization assay exhibits a wide dynamic titer range measured from 1/4 to less than 1/16,384. The results in Table 6 also indicate that all animals (C62104, C62105, C62109 and C62564) injected with AAV6 vectors demonstrate at least 1000-fold increase in neutralization antibody titers, which are internally consistent with increased neutralizing titers after AAV exposure, as expected.

Example 4: Pre-Screening NHP Serum-In Vivo Assay

An in vitro assay is used to determine neutralization titers in animals. Animals are pre-screened for neutralization in vitro before initiation of the assay. A specific or broad range of neutralization titers will be induced in each animal cohort to cover titers from 1/4 to 1/16000. Next animals are then subjected to different routes of administration of different AAV capsids encoding a reporter gene such as GFP or tag coding for a soluble protein that can be measured in the serum. Next animals with and without detectable (and pre-determined) in vitro neutralization titers are assessed for the amount of AAV-mediated tag expression. The ratio between expression level of the AAV-encoded tag in non-neutralizing animals and neutralizing animals is assessed in order to determine the level of in vitro neutralization determined by the in vitro assays described here to be predictive of in vivo neutralizing effect.

Example 5: AAV DJ Neutralizing Antibody Screening in Serum and CSF

Using the same test protocol as discussed in Example 2, AAV DJ neutralizing activity in several mammalian sera and CSF were screened. Similarly, Hela S3 cells were seeded at 10,000/well in a 96-well plate; maintained in Dulbecco's modified Eagle medium (DMEM) supplemented with 10% FBS (fetal bovine serum); and cultured overnight to reach a density of about 20,000/well. HS in Table 8 indicates human serum sample, and NHPS indicates non-human primate serum sample.

TABLE 7

AAV DJ Neutralization in Dog Serum (MOI = $10^{x4}$)

| Dilution | Samples (data given as %) | | | | | | | |
|---|---|---|---|---|---|---|---|---|
| | #1 | #2 | #3 | #4 | #5 | #6 | #7 | #8 |
| 1:16 | 76.7 | 76.4 | 67.6 | 76.4 | 67.7 | 69.5 | 67.6 | 65.0 |
| 1:64 | 84.4 | 79.5 | 84.3 | 86.6 | 76.6 | 76.9 | 79.9 | 79.2 |
| | #9 | #10 | #11 | #12 | #13 | #14 | #15 | control |
| 1:16 | 19.7 | 76.6 | 69.6 | 67.5 | 75.3 | 67.5 | 70.2 | 75.7 |
| 1:64 | 52.8 | 73.4 | 79.2 | 74.5 | 70.8 | 69.0 | 66.3 | 69.7 |
| control | | | | | | | | |
| 1:16 | 73.6 | | | | | | | |
| 1:64 | 67.9 | | | | | | | |

TABLE 8

AAV DJ Neutralizing Assay Using China Monkey Serum

| Dilution | Samples (data given as %) | | | | | | | |
|---|---|---|---|---|---|---|---|---|
| | #1 | #2 | #3 | #4 | #5 | #6 | #7 | #8 |
| 1:16 | 5.2 | 22.6 | 15.1 | 0.8 | 32.2 | 28.7 | 4.7 | 0.5 |
| 1:64 | 39.5 | 63.2 | 57.9 | 28.2 | 62.0 | 63.6 | 0.1 | 7.7 |
| 1:256 | 60.5 | 76.7 | 76.3 | 70.6 | 76.8 | 73.1 | 33.3 | 43.4 |
| | #9 | #10 | #11 | #12 | #13 | #14 | #15 | #16 |
| 1:16 | 1.2 | 0.6 | 39.5 | 0.5 | 0.2 | 24.3 | 32.2 | 0.3 |
| 1:64 | 34.5 | 32.3 | 71.6 | 7.6 | 0.1 | 59.5 | 64.8 | 0.4 |
| 1:256 | 58.9 | 69.2 | 76.5 | 60.0 | 0.6 | 74.0 | 73.1 | 0.4 |
| | #17 | #18 | #19 | #20 | #21 | #22 | #23 | #24 |
| 1:16 | 0.0 | 13.5 | 0.1 | 7.0 | 2.5 | 6.7 | 25.8 | 0.5 |
| 1:64 | 0.1 | 48.3 | 0.4 | 0.4 | 0.4 | 56.8 | 54.3 | 15.2 |
| 1:256 | 9.9 | 58.0 | 23.9 | 10.4 | 0.3 | 58.8 | 61.6 | 38.8 |
| | CTL HS | CTL NHPS | | | | | | |
| 1:16 | 8.3 | 0.1 | | | | | | |
| 1:64 | 60.8 | 18.3 | | | | | | |
| 1:256 | 77.9 | 65.0 | | | | | | |

AAV DJ neutralization was tested in China Monkey #19, #20, #21 and #22 at Day 1 and Day 43. Both Cerebrospinal fluid and serum samples were collected and analyzed.

TABLE 9

AAV-DJ Neutralizing Assay in CSF and Serum

| Dilution | #19D1 CSF | #19D1 serum | #19D43 CSF | #19D43 Serum |
|---|---|---|---|---|
| 1:256 | 43.3 | 51.6 | 4.6 | 2.7 |
| 1:4096 | 57.6 | 53.1 | 46.9 | 4.1 |
| 1:16384 | 58.7 | 53.4 | 55.0 | 28.0 |
| 1:65536 | 61.8 | 39.4 | 57.7 | 38.8 |
| | #20D1 CSF | #20D1 serum | #20D43 CSF | #20D43 Serum |
| 1:256 | 43.1 | 54.3 | 3.5 | 54.3 |
| 1:4096 | 59.3 | 52.1 | 24.7 | 52.1 |
| 1:16384 | 58.1 | 55.1 | 47.4 | 55.1 |
| 1:65536 | 59.5 | 39.3 | 52.4 | 39.3 |

TABLE 9-continued

AAV-DJ Neutralizing Assay in CSF and Serum

Samples (data given as %)

| Dilution | #19D1 CSF | #19D1 serum | #19D43 CSF | #19D43 Serum |
|---|---|---|---|---|
| | #21D1 CSF | #21D1 serum | #21D43 CSF | #21D43 Serum |
| 1:256 | 37.7 | 41.0 | 2.6 | 1.2 |
| 1:4096 | 56.9 | 50.3 | 10.6 | 0.8 |
| 1:16384 | 55.3 | 54.6 | 38.0 | 2.1 |
| 1:65536 | 58.4 | 41.7 | 46.7 | 22.6 |
| | #22D1 CSF | #22D1 serum | #22D43 CSF | #22D43 Serum |
| 1:256 | 43.9 | 54.5 | 2.5 | 1.0 |
| 1:4096 | 51.7 | 50.3 | 19.7 | 1.1 |
| 1:16384 | 58.6 | 53.0 | 46.6 | 1.5 |
| 1:65536 | 61.8 | 39.3 | 48.1 | 21.3 |

| | Control CSF | Control Serum |
|---|---|---|
| 1:256 | 33.0 | 42.8 |
| 1:4096 | 42.2 | 39.3 |
| 1:16384 | 37.7 | 36.0 |
| 1:65536 | 46.9 | 29.0 |

Example 6: AAV2 Neutralizing Antibody Screening in CSF and Serum of Monkey

AAV2 neutralization activity was tested in China Monkey #1 and #2 at Day 1 and Day 43. Both Cerebrospinal fluid and serum samples were collected and analyzed. In Table 10, the "/" indicates that no data were collected for that sample at that dilution.

TABLE 10

AAV2 neutralizing assay in CSF and serum

Samples (data given as %)

| Dilution | #1D1 CSF | #1D1 serum | #1D43 CSF | #1D43 Serum |
|---|---|---|---|---|
| 1:256 | 94.6 | 92.0 | 2.0 | 1.6 |
| 1:1024 | 92.9 | 91.9 | 61.6 | 49.6 |
| 1:4096 | 92.0 | 91.6 | 86.0 | 85.2 |
| 1:16384 | 91.7 | 89.8 | 90.4 | 88.6 |
| 1:65536 | 90.3 | 88.4 | 90.6 | 88.1 |
| 1:262144 | 90.7 | 88.7 | 89.0 | 88.4 |
| 1:1048576 | 90.0 | 90.0 | 89.2 | 89.6 |
| 0 | 92.9 | 91.5 | 93.3 | 92.2 |
| | #2D1 CSF | #2D1 serum | #2D43 CSF | #2D43 Serum |
| 1:256 | 95.5 | 90.1 | 2.5 | 1.4 |
| 1:1024 | 94.2 | 90.8 | 0.8 | 2.3 |
| 1:4096 | 90.6 | 90.1 | 49.3 | 64.5 |
| 1:16384 | 92.0 | 87.5 | 85.2 | 82.9 |
| 1:65536 | 89.3 | 88.5 | 87.8 | 88.4 |
| 1:262144 | 88.6 | 88.2 | 88.0 | 86.0 |
| 1:1048576 | 89.9 | 87.4 | 90.0 | 86.6 |
| 0 | 93.6 | 90.7 | 92.6 | 91.0 |

| Control | | | | |
|---|---|---|---|---|
| 1:256 | 92.5 | | | |
| 1:1024 | 89.6 | | | |
| 1:4096 | 90.9 | | | |
| 1:16384 | 90.1 | | | |
| 1:65536 | 85.7 | | | |
| 1:262144 | / | | | |
| 1:1048576 | / | | | |
| 0 | / | | | |

Example 7: AAV Serotype Neutralizing Antibody Screening Using Non-Human Primate Serum AAV serotype (AAV1 and AAV-DJ) neutralization was tested using 84 non-human primate (NHP) serum samples. AAV1 or AAV-DJ at MOI $10^5$ was incubated with NHP serum diluted at 1:16 or 1:64.

TABLE 11

AAV1 neutralizing assay using non-human primate serum (MOI $10^5$)

Samples (data given as %)

| | 1 | 2 | 3 | 4 | 5 | 6 | 7 | 8 | 9 | 10 |
|---|---|---|---|---|---|---|---|---|---|---|
| 1:16 | 0.3 | 90.6 | 12.7 | 94.4 | 94.7 | 0.7 | 28.6 | 94.3 | 94.7 | 96.9 |
| 1:64 | 33.3 | 91.2 | 77.7 | 92.1 | 92.7 | 46.2 | 81.6 | 92.7 | 92.0 | 93.3 |
| | 11 | 12 | 13 | 14 | 15 | 16 | 17 | 18 | 19 | 20 |
| 1:16 | 0.9 | 96.9 | 96.6 | 96.4 | 13.9 | 93.4 | 1.3 | 0.7 | 0.9 | 86.3 |
| 1:64 | 0.5 | 93.1 | 92.5 | 92.5 | 77.2 | 92.8 | 3.2 | 0.2 | 15.3 | 91.4 |
| | 21 | 22 | 23 | 24 | 25 | 26 | 27 | 28 | 29 | 30 |
| 1:16 | 96.9 | 2.8 | 0.4 | 36.8 | 2.5 | 0.2 | 0.4 | 1.9 | 13.2 | 96.5 |
| 1:64 | 93.4 | 27.1 | 0.8 | 90.0 | 73.0 | 1.9 | 1.7 | 2.0 | 58.2 | 92.9 |
| | 31 | 32 | 33 | 34 | 35 | 36 | 37 | 38 | 39 | 40 |
| 1:16 | 90.4 | 2.1 | 95.0 | 33.2 | 79.4 | 93.0 | 1.2 | 0.9 | 30.5 | 98.9 |
| 1:64 | 91.4 | 27.4 | 92.3 | 1.4 | 92.4 | 91.5 | 5.2 | 1.7 | 89.3 | 95.1 |
| | 41 | 42 | 43 | 44 | 45 | 46 | 47 | 48 | 49 | 50 |
| 1:16 | 67.7 | 3.1 | 82.7 | 1.4 | 2.1 | 87.9 | 84.1 | 2.6 | 0.8 | 93.4 |
| 1:64 | 88.6 | 4.2 | 92.7 | 4.0 | 1.3 | 95.2 | 94.2 | 0.9 | 1.0 | 94.5 |

TABLE 11-continued

AAV1 neutralizing assay using non-human primate serum (MOI 10$^5$)

Samples (data given as %)

| | 51 | 52 | 53 | 54 | 55 | 56 | 57 | 58 | 59 | 60 |
|---|---|---|---|---|---|---|---|---|---|---|
| 1:16 | 13.9 | 94.6 | 97.4 | 87.6 | 81.4 | 84.9 | 17.0 | 57.6 | 90.7 | 96.4 |
| 1:64 | 81.9 | 95.5 | 95.3 | 94.8 | 94.0 | 94.5 | 85.3 | 92.9 | 94.8 | 95.0 |

| | 61 | 62 | 63 | 64 | 65 | 66 | 67 | 68 | 69 | 70 |
|---|---|---|---|---|---|---|---|---|---|---|
| 1:16 | 94.8 | 95.0 | 61.3 | 96.3 | 2.2 | 0.6 | 2.4 | 93.0 | 3.7 | 59.1 |
| 1:64 | 95.1 | 95.0 | 88.7 | 92.9 | 44.4 | 1.0 | 2.8 | 91.5 | 70.1 | 85.5 |

| | 71 | 72 | 73 | 74 | 75 | 76 | 77 | 78 | 79 | 80 |
|---|---|---|---|---|---|---|---|---|---|---|
| 1:16 | 1.7 | 89.8 | 0.9 | 22.6 | 2.0 | 1.4 | 0.2 | 93.1 | 72.2 | 76.9 |
| 1:64 | 21.6 | 92.9 | 0.3 | 76.2 | 46.0 | 0.2 | 1.6 | 90.3 | 85.5 | 88.1 |

| | 81 | 82 | 83 | 84 | Control 1 | Control 2 |
|---|---|---|---|---|---|---|
| 1:16 | 94.3 | 91.5 | 88.5 | 93.4 | 86.8 | 0.7 |
| 1:64 | 89.9 | 88.9 | 87.8 | 88.6 | 90.0 | 0.3 |

TABLE 12

AAV-DJ neutralizing assay using non-human primate serum (MOI 10$^5$)

Samples (data given as %)

| | 1 | 2 | 3 | 4 | 5 | 6 | 7 | 8 | 9 | 10 |
|---|---|---|---|---|---|---|---|---|---|---|
| 1:16 | 1.4 | 1.1 | 10.7 | 61.1 | 17.8 | 72.9 | 54.0 | 64.3 | 3.7 | 0.9 |
| 1:64 | 1.2 | 69.2 | 92.5 | 93.6 | 94.8 | 96.4 | 96.0 | 97.5 | 58.7 | 42.9 |

| | 11 | 12 | 13 | 14 | 15 | 16 | 17 | 18 | 19 | 20 |
|---|---|---|---|---|---|---|---|---|---|---|
| 1:16 | 1.6 | 93.8 | 84.4 | 1.5 | 1.5 | 78.5 | 77.7 | 1.6 | 77.4 | 81.8 |
| 1:64 | 1.3 | 97.7 | 97.1 | 70.3 | 1.0 | 97.2 | 95.1 | 1.5 | 96.7 | 97.3 |

| | 21 | 22 | 23 | 24 | 25 | 26 | 27 | 28 | 29 | 30 |
|---|---|---|---|---|---|---|---|---|---|---|
| 1:16 | 27.2 | 1.9 | 1.0 | 0.9 | 6.3 | 1.5 | 2.5 | 1.1 | 2.2 | 1.1 |
| 1:64 | 93.4 | 71.8 | 0.7 | 38.3 | 87.0 | 1.2 | 1.4 | 2.8 | 19.4 | 29.1 |

| | 31 | 32 | 33 | 34 | 35 | 36 | 37 | 38 | 39 | 40 |
|---|---|---|---|---|---|---|---|---|---|---|
| 1:16 | 0.5 | 10.9 | 3.3 | 1.4 | 0.7 | 66.0 | 2.29 | 3.1 | 0.6 | 66.0 |
| 1:64 | 1.4 | 80.8 | 79.2 | 1.1 | 8.0 | 88.0 | 0.75 | 92.0 | 0.1 | 95.7 |

| | 41 | 42 | 43 | 44 | 45 | 46 | 47 | 48 | 49 | 50 |
|---|---|---|---|---|---|---|---|---|---|---|
| 1:16 | 60.6 | 0.2 | 0.1 | 0.6 | 53.7 | 3.0 | 0.7 | 0.1 | 0.7 | 9.0 |
| 1:64 | 93.6 | 0.2 | 2.1 | 0.8 | 89.3 | 47.5 | 0.2 | 20.2 | 0.1 | 88.76 |

| | 51 | 52 | 53 | 54 | 55 | 56 | 57 | 58 | 59 | 60 |
|---|---|---|---|---|---|---|---|---|---|---|
| 1:16 | 0.7 | 0.8 | 88.9 | 61.4 | 0.7 | 90.1 | 91.5 | 72.6 | 68.3 | 77.2 |
| 1:64 | 68.8 | 0.9 | 95.9 | 87.5 | 67.6 | 97.7 | 97.1 | 94.1 | 92.8 | 91.5 |

| | 61 | 62 | 63 | 64 | 65 | 66 | 67 | 68 | 69 | 70 |
|---|---|---|---|---|---|---|---|---|---|---|
| 1:16 | 65.7 | 0.4 | 1.1 | 80.7 | 0.4 | 3.1 | 81.7 | 1.0 | 2.4 | 6.7 |
| 1:64 | 93.0 | 0.7 | 69.8 | 89.3 | 15.3 | 0.4 | 91.0 | 1.1 | 87.8 | 77.3 |

| | 71 | 72 | 73 | 74 | 75 | 76 | 77 | 78 | 79 | 80 |
|---|---|---|---|---|---|---|---|---|---|---|
| 1:16 | 0.6 | 67.2 | 0.2 | 17.2 | 10.5 | 5.7 | 3.3 | 47.5 | 10.4 | 38.0 |
| 1:64 | 0.3 | 81.4 | 2.3 | 88.9 | 83.3 | 69.1 | 8.8 | 89.6 | 70.5 | 88.7 |

| | 81 | 82 | 83 | 84 | Control 1 | Control 2 |
|---|---|---|---|---|---|---|
| 1:16 | 39.6 | 52.9 | 80.2 | 60.7 | 0.6 | 0.7 |
| 1:64 | 49.7 | 93.7 | 94.0 | 88.7 | 0.2 | 0.3 |

Example 8: AAV Serotype (DJ8, AAV9, AAV6 and DJ) Neutralization Studies in Monkey 35 monkey serum samples were tested for AAV-DJ8, AAV6 and AAV9 neutralization. In Table 13, the "/" indicates that no data were collected for that sample at that dilution.

TABLE 13

AAV-DJ8 neutralization in Monkey serum (MOI $10^4$)

| Dilution | Samples (data given as %) | | | | | | | |
|---|---|---|---|---|---|---|---|---|
| | #1 | #2 | #3 | #4 | #5 | #6 | #7 | #8 |
| 1:16 | 47.3 | 60.8 | 46.4 | 48.2 | 53.3 | 30.6 | 45.1 | 58.2 |
| 1:64 | 38.5 | 55.5 | 46.9 | / | 44.9 | 58.2 | 57.8 | 54.0 |
| | #9 | #10 | #11 | #12 | #13 | #14 | #15 | #16 |
| 1:16 | 58.2 | 46.3 | 63.7 | 48.7 | 67.1 | 68.5 | 63.5 | 66.6 |
| 1:64 | 54.0 | 51.0 | 55.9 | 57.3 | 47.3 | 58.9 | 60.3 | 54.9 |
| | #17 | #18 | #19 | #20 | #21 | #22 | #23 | #24 |
| 1:16 | 59.6 | 21.8 | 57.7 | 54.0 | 59.5 | 47.2 | 57.7 | 49.5 |
| 1:64 | 46.0 | 42.0 | 43.1 | 39.1 | 47.0 | 41.2 | 51.2 | 45.6 |
| | #25 | #26 | #27 | #28 | #29 | #30 | #31 | #32 |
| 1:16 | 71.0 | 42.9 | 61.2 | 39.1 | 49.9 | 39.6 | 39.3 | 59.2 |
| 1:64 | 50.3 | 47.8 | 48.0 | 23.1 | 0.0 | 38.3 | 51.2 | 48.8 |
| | #33 | #34 | #35 | control | | | | |
| 1:16 | 61.4 | 34.7 | 65.7 | 57.9 | | | | |
| 1:64 | 39.2 | 34.0 | 56.0 | 53.0 | | | | |

TABLE 14

AAV6 neutralization in Monkey serum (MOI $10^4$)

| Dilution | Samples (data given as %) | | | | | | | |
|---|---|---|---|---|---|---|---|---|
| | #1 | #2 | #3 | #4 | #5 | #6 | #7 | #8 |
| 1:16 | 29.7 | 7.7 | 7.7 | 15.9 | 9.7 | 26.4 | 37.9 | 13.9 |
| 1:64 | 22.4 | 21.3 | 19.2 | 19.7 | 12.6 | 20.7 | 24.1 | 18.5 |
| | #9 | #10 | #11 | #12 | #13 | #14 | #15 | #16 |
| 1:16 | 28.6 | 37.1 | 34.3 | 32.0 | 32.1 | 29.8 | 24.6 | 49.4 |
| 1:64 | 25.9 | 22.3 | 29.8 | 25.0 | 19.7 | 36.6 | 32.1 | 29.3 |
| | #17 | #18 | #19 | #20 | #21 | #22 | #23 | #24 |
| 1:16 | 52.6 | 52.0 | 9.3 | 21.1 | 35.6 | 18.6 | 27.3 | 5.8 |
| 1:64 | 25.9 | 35.0 | 15.4 | 19.1 | 33.5 | 34.4 | 28.3 | 2.5 |
| | #25 | #26 | #27 | #28 | #29 | #30 | #31 | #32 |
| 1:16 | 30.0 | 16.3 | 31.4 | 45.6 | 42.9 | 55.4 | 50.2 | 26.0 |
| 1:64 | 37.7 | 25.7 | 43.8 | 31.6 | 41.7 | 24.6 | 25.8 | 28.9 |
| | #33 | #34 | #35 | control | | | | |
| 1:16 | 30.6 | 15.0 | 26.0 | 17.6 | | | | |
| 1:64 | 28.1 | 19.3 | 17.9 | 21.6 | | | | |

TABLE 15

AAV9 neutralization in Monkey serum (MOI $10^5$)

| Dilution | Samples (data given as %) | | | | | | | |
|---|---|---|---|---|---|---|---|---|
| | #1 | #2 | #3 | #4 | #5 | #6 | #7 | #8 |
| 1:16 | 22.0 | 50.0 | 32.2 | 17.3 | 42.7 | 44.6 | 32.3 | 42.1 |
| 1:64 | 39.7 | 47.4 | 46.0 | 33.7 | 39.4 | 34.1 | 48.3 | 34.4 |
| | #9 | #10 | #11 | #12 | #13 | #14 | #15 | #16 |
| 1:16 | 38.7 | 54.5 | 53.6 | 54.3 | 56.3 | 51.1 | 39.7 | 50.1 |
| 1:64 | 38.6 | 46.7 | 50.1 | 52.3 | 44.1 | 46.4 | 50.2 | 44.7 |
| | #17 | #18 | #19 | #20 | #21 | #22 | #23 | #24 |
| 1:16 | 3.7 | 2.3 | 27.0 | 57.3 | 56.9 | 1.1 | 26.7 | 12.1 |
| 1:64 | 28.2 | 1.7 | 42.7 | 45.9 | 44.1 | 27.6 | 39.4 | 30.5 |
| | #25 | #26 | #27 | #28 | #29 | #30 | #31 | #32 |
| 1:16 | 23.7 | 52.3 | 43.3 | 27.0 | 57.3 | 56.9 | 1.1 | 26.7 |
| 1:64 | 33.0 | 42.8 | 37.4 | 42.7 | 45.9 | 44.1 | 27.6 | 39.4 |
| | #33 | #34 | #35 | control | | | | |
| 1:16 | 12.1 | 23.7 | 52.3 | 43.3 | | | | |
| 1:64 | 30.5 | 33.0 | 42.8 | 37.4 | | | | |

TABLE 16

AAV-DJ neutralization in Monkey serum (MOI = $10^4$)

| Dilution | Samples (data given as %) | | | | | | | |
|---|---|---|---|---|---|---|---|---|
| | #1 | #2 | #3 | #4 | #5 | #6 | #7 | #8 |
| 1:16 | 26.8 | 43.3 | 16.5 | 0.4 | 15.6 | 4.7 | 36.8 | 24.6 |
| 1:64 | 77.4 | 77.1 | 75.8 | 44.9 | 64.1 | 53.4 | 76.0 | 65.8 |
| | #9 | #10 | #11 | #12 | #13 | #14 | #15 | #16 |
| 1:16 | 32.3 | 74.5 | 70.4 | 13.1 | 40.0 | 39.6 | 12.0 | 44.9 |
| 1:64 | 37.2 | 75.1 | 69.6 | 58.8 | 74.6 | 75.2 | 73.6 | 77.0 |
| | #17 | #18 | #19 | #20 | #21 | #22 | #23 | #24 |
| 1:16 | 11.4 | 0.3 | 38.3 | 55.6 | 48.6 | 1.8 | 9.1 | 6.7 |
| 1:64 | 67.8 | 12.1 | 68.9 | 66.4 | 80.7 | 61.6 | 61.8 | 70.2 |
| | #25 | #26 | #27 | #28 | #29 | #30 | #31 | #32 |
| 1:16 | 58.5 | 0.6 | 62.8 | 49.6 | 74.2 | 54.0 | 17.5 | 40.7 |
| 1:64 | 76.4 | 8.8 | 69.2 | 64.0 | 75.1 | 68.2 | 56.6 | 59.7 |
| | #33 | #34 | #35 | control | | | | |
| 1:16 | 31.5 | 53.6 | 39.1 | 49.0 | | | | |
| 1:64 | 53.6 | 58.4 | 56.7 | 45.1 | | | | |

Example 9: Cross Neutralizing Reaction Between AAV Serotypes

To test the induction of cross-reactive antibodies to an AAV capsid serotype that has never been seen by an animal, cross reaction assays were performed. In these assays, mice were injected with a first AAV serotype ($AAV_X$). Serum samples were collected after each injection and subjected to ELISA assays for measurement of reactivity to a second AAV serotype ($AAV_Y$). To perform the ELISA assays, the plates were coated with $AAV_Y$ and different serum dilutions were monitored for $AAV_X$ reactivity. $AAV_X$ may or may not be the same capsid serotype as $AAV_Y$.

AAV2 Cross Neutralization

Cross reaction: mice were injected with AAV2 viruses, serum samples were collected after each injection and subject to ELISA assays for testing anti-AAV-DJ and AAVrh10 mouse IgG. For the ELISA assay, the plates were coated with AAV-DJ, AAVrh10 or AAV2 mouse IgG, then different serum dilutions were monitored for AAV2 reactivity.

TABLE 17

AAV-DJ Binding After AAV2 Injection

| Dilution | 1st injection | | | 2nd injection | | |
|---|---|---|---|---|---|---|
| | #1 | #2 | #3 | #4 | #5 | #6 |
| 1:50 | 0.7 | 0.7 | 0.6 | 0.8 | 0.8 | 1.3 |
| 1:400 | 1.1 | 1.0 | 0.9 | 1.1 | 0.9 | 1.2 |
| 1:3200 | 0.4 | 0.3 | 0.4 | 1.1 | 0.9 | 0.9 |
| 1:25600 | 0.1 | 0.1 | 0.1 | 0.4 | 0.2 | 0.3 |
| 1:204800 | 0.1 | 0.1 | 0.1 | 0.1 | 0.1 | 0.1 |
| 1:1638400 | 0.2 | 0.1 | 0.1 | 0.1 | 0.1 | 0.1 |
| 1:13107200 | 0.1 | 0.1 | 0.1 | 0.1 | 0.1 | 0.1 |
| 0 | 0.1 | 0.1 | 0.1 | 0.1 | 0.1 | 0.1 |

| Dilution | 3rd injection | | | 3 time point control | | |
|---|---|---|---|---|---|---|
| | #7 | #8 | #9 | #10 | #11 | #12 |
| 1:50 | 1.1 | 1.2 | 0.9 | 0.5 | 0.6 | 0.5 |
| 1:400 | 1.1 | 1.2 | 0.9 | 0.2 | 0.2 | 0.2 |
| 1:3200 | 0.6 | 0.7 | 1.0 | 0.1 | 0.1 | 0.1 |
| 1:25600 | 0.2 | 0.2 | 0.3 | 0.1 | 0.1 | 0.1 |
| 1:204800 | 0.1 | 0.1 | 0.1 | 0.1 | 0.1 | 0.1 |
| 1:1638400 | 0.1 | 0.1 | 0.1 | 0.1 | 0.1 | 0.1 |
| 1:13107200 | 0.1 | 0.1 | 0.1 | 0.1 | 0.1 | 0.1 |
| 0 | 0.1 | 0.1 | 0.1 | 0.1 | 0.1 | 0.1 |

TABLE 18

AAVrh10 binding after AAV2 injection

| Dilution | 1st injection | | | 2nd injection | | |
|---|---|---|---|---|---|---|
| | #1 | #2 | #3 | #4 | #5 | #6 |
| 1:50 | 0.3 | 0.3 | 0.2 | 0.3 | 0.5 | 0.9 |
| 1:400 | 0.1 | 0.1 | 0.1 | 0.1 | 0.2 | 0.3 |
| 1:3200 | 0.1 | 0.1 | 0.1 | 0.1 | 0.1 | 0.1 |
| 1:25600 | 0.1 | 0.1 | 0.1 | 0.1 | 0.1 | 0.1 |
| 1:204800 | 0.1 | 0.1 | 0.1 | 0.1 | 0.1 | 0.1 |
| 1:1638400 | 0.1 | 0.1 | 0.1 | 0.1 | 0.1 | 0.1 |
| 1:13107200 | 0.1 | 0.1 | 0.1 | 0.1 | 0.1 | 0.1 |
| 0 | 0.1 | 0.1 | 0.1 | 0.1 | 0.1 | 0.1 |

| Dilution | 3rd injection | | | 3 time point control | | |
|---|---|---|---|---|---|---|
| | #7 | #8 | #9 | #10 | #11 | #12 |
| 1:50 | 0.7 | 0.9 | 0.5 | 0.5 | 0.5 | 0.4 |
| 1:400 | 0.8 | 0.9 | 0.2 | 0.2 | 0.2 | 0.2 |
| 1:3200 | 0.1 | 0.1 | 0.1 | 0.1 | 0.1 | 0.1 |
| 1:25600 | 0.1 | 0.1 | 0.1 | 0.1 | 0.1 | 0.1 |
| 1:204800 | 0.1 | 0.1 | 0.1 | 0.1 | 0.1 | 0.1 |
| 1:1638400 | 0.1 | 0.1 | 0.1 | 0.1 | 0.1 | 0.1 |
| 1:13107200 | 0.1 | 0.1 | 0.1 | 0.1 | 0.1 | 0.1 |
| 0 | 0.1 | 0.1 | 0.1 | 0.1 | 0.1 | 0.1 |

TABLE 19

AAV2 mouse IgG binding after AAV2 injection

| Dilution | 1st injection | | | 2nd injection | | |
|---|---|---|---|---|---|---|
| | #1 | #2 | #3 | #4 | #5 | #6 |
| 1:50 | 0.4 | 0.4 | 0.4 | 0.4 | 0.6 | 1.0 |
| 1:400 | 0.3 | 0.3 | 0.3 | 0.4 | 0.3 | 0.7 |
| 1:3200 | 0.7 | 0.6 | 0.6 | 0.7 | 0.7 | 0.8 |
| 1:25600 | 0.3 | 0.5 | 0.6 | 0.9 | 0.9 | 0.9 |
| 1:204800 | 0.2 | 0.3 | 0.3 | 0.8 | 0.8 | 0.6 |
| 1:1638400 | 0.2 | 0.2 | 0.2 | 0.5 | 0.5 | 0.3 |
| 1:13107200 | 0.1 | 0.1 | 0.2 | 0.5 | 0.4 | 0.3 |
| 0 | 0.1 | 0.1 | 0.1 | 0.1 | 0.1 | 0.1 |

| Dilution | 3rd injection | | | 3 time point control | | |
|---|---|---|---|---|---|---|
| | #7 | #8 | #9 | #10 | #11 | #12 |
| 1:50 | 0.8 | 0.9 | 0.6 | 0.5 | 0.5 | 0.4 |
| 1:400 | 0.5 | 0.6 | 0.4 | 0.2 | 0.2 | 0.2 |
| 1:3200 | 0.8 | 0.8 | 0.7 | 0.1 | 0.1 | 0.1 |
| 1:25600 | 0.9 | 0.8 | 0.9 | 0.1 | 0.1 | 0.1 |
| 1:204800 | 0.6 | 0.5 | 0.6 | 0.1 | 0.1 | 0.1 |
| 1:1638400 | 0.4 | 0.3 | 0.2 | 0.1 | 0.1 | 0.1 |
| 1:13107200 | 0.3 | 0.2 | 0.2 | 0.1 | 0.1 | 0.1 |
| 0 | 0.1 | 0.1 | 0.1 | 0.1 | 0.1 | 0.1 |

AAV6 Cross Neutralization

Cross reaction: mice were injected with AAV6 viruses, serum samples were collected after each injection and subject to ELISA assay for testing anti-AAV-DJ, AAVrh10 and AAV2 mouse IgG. For the ELISA assay, the plates were coated with AAV-DJ, AAVrh10 or AAV2, then different serum dilutions were monitored for AAV6 reactivity.

TABLE 20

AAV-DJ binding after AAV6 injection

| Dilution | 1st injection | | | 2nd injection | | |
|---|---|---|---|---|---|---|
| | #1 | #2 | #3 | #4 | #5 | #6 |
| 1:50 | 0.3 | 0.3 | 0.4 | 0.4 | 0.5 | 0.5 |
| 1:400 | 0.1 | 0.1 | 0.1 | 0.2 | 0.2 | 0.2 |
| 1:3200 | 0.1 | 0.1 | 0.1 | 0.1 | 0.1 | 0.1 |
| 1:25600 | 0.1 | 0.1 | 0.1 | 0.1 | 0.1 | 0.1 |
| 1:204800 | 0.1 | 0.1 | 0.1 | 0.1 | 0.1 | 0.1 |
| 1:1638400 | 0.1 | 0.1 | 0.1 | 0.1 | 0.1 | 0.1 |
| 1:13107200 | 0.1 | 0.1 | 0.1 | 0.1 | 0.1 | 0.6 |
| 0 | 0.1 | 0.1 | 0.1 | 0.1 | 0.1 | 0.1 |

| Dilution | 3rd injection | | | 3 time point control | | |
|---|---|---|---|---|---|---|
| | #7 | #8 | #9 | #10 | #11 | #12 |
| 1:50 | 0.5 | 0.7 | 0.6 | 0.5 | 0.6 | 0.5 |
| 1:400 | 0.2 | 0.2 | 0.3 | 0.2 | 0.2 | 0.2 |
| 1:3200 | 0.1 | 0.1 | 0.1 | 0.1 | 0.1 | 0.1 |
| 1:25600 | 0.1 | 0.2 | 0.1 | 0.1 | 0.1 | 0.1 |
| 1:204800 | 0.1 | 0.1 | 0.1 | 0.1 | 0.1 | 0.1 |
| 1:1638400 | 0.1 | 0.1 | 0.1 | 0.1 | 0.1 | 0.1 |
| 1:13107200 | 0.1 | 0.1 | 0.1 | 0.1 | 0.1 | 0.1 |
| 0 | 0.1 | 0.1 | 0.1 | 0.1 | 0.1 | 0.2 |

TABLE 21

AAV2 binding after AAV6 injection

| | 1st injection | | | 2nd injection | | |
|---|---|---|---|---|---|---|
| Dilution | #1 | #2 | #3 | #4 | #5 | #6 |
| 1:50 | 0.3 | 0.3 | 0.3 | 0.4 | 0.4 | 0.5 |
| 1:400 | 0.1 | 0.1 | 0.1 | 0.1 | 0.2 | 0.2 |
| 1:3200 | 0.1 | 0.1 | 0.1 | 0.1 | 0.1 | 0.1 |
| 1:25600 | 0.1 | 0.1 | 0.1 | 0.1 | 0.1 | 0.1 |
| 1:204800 | 0.1 | 0.1 | 0.1 | 0.1 | 0.1 | 0.1 |
| 1:1638400 | 0.1 | 0.1 | 0.1 | 0.1 | 0.1 | 0.1 |
| 1:13107200 | 0.2 | 0.1 | 0.1 | 0.1 | 0.1 | 0.1 |
| 0 | 0.1 | 0.1 | 0.1 | 0.1 | 0.1 | 0.1 |

| | 3rd injection | | | 3 time point control | | |
|---|---|---|---|---|---|---|
| Dilution | #7 | #8 | #9 | #10 | #11 | #12 |
| 1:50 | 0.3 | 0.5 | 0.4 | 0.4 | 0.5 | 0.5 |
| 1:400 | 0.1 | 0.2 | 0.2 | 0.2 | 0.2 | 0.2 |
| 1:3200 | 0.1 | 0.1 | 0.1 | 0.1 | 0.1 | 0.1 |
| 1:25600 | 0.1 | 0.1 | 0.1 | 0.1 | 0.1 | 0.1 |
| 1:204800 | 0.1 | 0.1 | 0.1 | 0.1 | 0.1 | 0.1 |
| 1:1638400 | 0.1 | 0.1 | 0.1 | 0.1 | 0.1 | 0.1 |
| 1:13107200 | 0.1 | 0.1 | 0.1 | 0.1 | 0.1 | 0.1 |
| 0 | 0.1 | 0.1 | 0.1 | 0.1 | 0.1 | 0.1 |

TABLE 22

AAVrh10 binding after AAV6 injection

| | 1st injection | | | 2nd injection | | |
|---|---|---|---|---|---|---|
| Dilution | #1 | #2 | #3 | #4 | #5 | #6 |
| 1:50 | 0.3 | 0.3 | 0.2 | 0.3 | 0.3 | 0.4 |
| 1:400 | 0.1 | 0.1 | 0.1 | 0.1 | 0.2 | 0.2 |
| 1:3200 | 0.1 | 0.1 | 0.1 | 0.1 | 0.1 | 0.1 |
| 1:25600 | 0.1 | 0.1 | 0.1 | 0.1 | 0.1 | 0.1 |
| 1:204800 | 0.2 | 0.1 | 0.1 | 0.1 | 0.1 | 0.1 |
| 1:1638400 | 0.2 | 0.1 | 0.1 | 0.1 | 0.1 | 0.1 |
| 1:13107200 | 0.3 | 0.1 | 0.1 | 0.1 | 0.1 | 0.1 |
| 0 | 0.3 | 0.1 | 0.1 | 0.1 | 0.1 | 0.1 |

| | 3rd injection | | | 3 time point control | | |
|---|---|---|---|---|---|---|
| Dilution | #7 | #8 | #9 | #10 | #11 | #12 |
| 1:50 | 0.3 | 0.5 | 0.3 | 0.4 | 0.5 | 0.6 |
| 1:400 | 0.2 | 0.2 | 0.2 | 0.2 | 0.2 | 0.2 |
| 1:3200 | 0.1 | 0.1 | 0.1 | 0.1 | 0.1 | 0.1 |
| 1:25600 | 0.1 | 0.1 | 0.1 | 0.1 | 0.1 | 0.1 |
| 1:204800 | 0.1 | 0.1 | 0.1 | 0.1 | 0.1 | 0.1 |
| 1:1638400 | 0.1 | 0.1 | 0.1 | 0.1 | 0.1 | 0.1 |
| 1:13107200 | 0.1 | 0.1 | 0.1 | 0.1 | 0.1 | 0.1 |
| 0 | 0.10 | 0.1 | 0.1 | 0.1 | 0.1 | 0.1 |

AAVrh10 Cross Neutralization

Cross reaction: mice were injected with AAVrh10 viruses, serum samples were collected after each injection and subject to ELISA assay for testing anti-AAV-DJ, AAVrh10 and AAV2 mouse IgG. For the ELISA assay, the plates were coated with AAV-DJ, AAVrh10 mouse IgG, or AAV2, then different serum dilutions were monitored for AAVrh10 reactivity.

TABLE 23

AAV2 binding after AAVrh10 injection

| | 1st injection | | | 2nd injection | | |
|---|---|---|---|---|---|---|
| Dilution | #1 | #2 | #3 | #4 | #5 | #6 |
| 1:50 | 0.4 | 0.4 | 0.4 | 1.3 | 0.6 | 0.7 |
| 1:400 | 0.2 | 0.1 | 0.1 | 0.4 | 0.3 | 0.2 |
| 1:3200 | 0.1 | 0.1 | 0.1 | 0.1 | 0.1 | 0.1 |
| 1:25600 | 0.1 | 0.1 | 0.1 | 0.1 | 0.1 | 0.2 |
| 1:204800 | 0.1 | 0.1 | 0.1 | 0.1 | 0.1 | 0.1 |
| 1:1638400 | 0.2 | 0.1 | 0.1 | 0.2 | 0.1 | 0.1 |
| 1:13107200 | 0.1 | 0.2 | 0.1 | 0.1 | 0.1 | 0.9 |
| 0 | 0.1 | 0.1 | 0.1 | 0.1 | 0.2 | 0.1 |

| | 3rd injection | | | 3 time point control | | |
|---|---|---|---|---|---|---|
| Dilution | #7 | #8 | #9 | #10 | #11 | #12 |
| 1:50 | 0.9 | 0.9 | 1.4 | 0.3 | 0.5 | 0.9 |
| 1:400 | 0.3 | 0.3 | 1.0 | 0.1 | 0.1 | 0.3 |
| 1:3200 | 0.1 | 0.1 | 0.3 | 0.1 | 0.1 | 0.1 |
| 1:25600 | 0.1 | 0.1 | 0.1 | 0.1 | 0.1 | 0.2 |
| 1:204800 | 0.1 | 0.1 | 0.1 | 0.1 | 0.1 | 0.1 |
| 1:1638400 | 0.1 | 0.1 | 0.1 | 0.1 | 0.1 | 0.3 |
| 1:13107200 | 0.1 | 0.1 | 0.1 | 0.1 | 0.1 | 0.1 |
| 0 | 0.2 | 0.2 | 0.1 | 0.2 | 0.2 | 0.6 |

TABLE 24

AAV DJ binding after AAVrh10 injection

| | 1st injection | | | 2nd injection | | |
|---|---|---|---|---|---|---|
| Dilution | #1 | #2 | #3 | #4 | #5 | #6 |
| 1:50 | 1.0 | 0.7 | 1.0 | 1.1 | 1.0 | 1.1 |
| 1:400 | 0.3 | 0.1 | 0.3 | 1.3 | 0.6 | 0.9 |
| 1:3200 | 0.1 | 0.1 | 0.1 | 0.5 | 0.1 | 0.2 |
| 1:25600 | 0.1 | 0.1 | 0.1 | 0.1 | 0.1 | 0.1 |
| 1:204800 | 0.1 | 0.1 | 0.1 | 0.1 | 0.1 | 0.1 |
| 1:1638400 | 0.1 | 0.1 | 0.1 | 0.1 | 0.1 | 0.1 |
| 1:13107200 | 0.1 | 0.1 | 0.1 | 0.1 | 0.1 | 0.1 |
| 0 | 0.2 | 0.6 | 0.2 | 0.4 | 0.1 | 0.1 |

| | 3rd injection | | | 3 time point control | | |
|---|---|---|---|---|---|---|
| Dilution | #7 | #8 | #9 | #10 | #11 | #12 |
| 1:50 | 0.9 | 1.4 | 1.5 | 0.3 | 0.5 | 0.8 |
| 1:400 | 1.2 | 0.6 | 1.4 | 0.1 | 0.1 | 0.2 |
| 1:3200 | 0.8 | 0.1 | 1.2 | 0.1 | 0.1 | 0.1 |
| 1:25600 | 0.2 | 0.1 | 0.3 | 0.1 | 0.1 | 0.1 |
| 1:204800 | 0.1 | 0.1 | 0.1 | 0.1 | 0.1 | 0.1 |
| 1:1638400 | 0.1 | 0.1 | 0.1 | 0.1 | 0.1 | 0.1 |
| 1:13107200 | 0.2 | 0.1 | 0.1 | 0.1 | 0.1 | 0.1 |
| 0 | 0.1 | 0.1 | 0.1 | 0.1 | 0.1 | 0.1 |

TABLE 25

AAVrh10 binding and anti-AAVrh10 mouse IgG

| | 1st injection | | | 2nd injection | | |
|---|---|---|---|---|---|---|
| Dilution | #1 | #2 | #3 | #4 | #5 | #6 |
| 1:50 | 1.1 | 1.3 | 1.1 | 1.4 | 1.0 | 1.0 |
| 1:400 | 1.4 | 1.5 | 1.6 | 1.3 | 1.4 | 1.3 |
| 1:3200 | 0.9 | 0.7 | 1.7 | 2.1 | 1.9 | 2.0 |
| 1:25600 | 0.3 | 0.2 | 0.6 | 2.0 | 1.2 | 1.1 |
| 1:204800 | 0.1 | 0.1 | 0.2 | 0.9 | 0.5 | 0.4 |
| 1:1638400 | 0.2 | 0.1 | 0.2 | 0.7 | 0.3 | 0.2 |
| 1:13107200 | 0.1 | 0.1 | 0.1 | 0.3 | 0.1 | 0.2 |
| 0 | 0.1 | 0.1 | 0.1 | 0.2 | 0.2 | 0.2 |

TABLE 25-continued

AAVrh10 binding and anti-AAVrh10 mouse IgG

| | 3rd injection | | | 3 time point control | | |
|---|---|---|---|---|---|---|
| Dilution | #7 | #8 | #9 | #10 | #11 | #12 |
| 1:50 | 1.1 | 1.2 | 1.5 | 0.4 | 0.6 | 0.8 |
| 1:400 | 1.3 | 1.5 | 1.4 | 0.1 | 0.1 | 0.2 |
| 1:3200 | 2.0 | 2.1 | 1.9 | 0.1 | 0.1 | 0.1 |
| 1:25600 | 1.5 | 1.3 | 1.8 | 0.3 | 0.1 | 0.1 |
| 1:204800 | 0.6 | 0.5 | 0.9 | 0.1 | 0.1 | 0.1 |
| 1:1638400 | 0.5 | 0.3 | 0.7 | 0.1 | 0.1 | 0.1 |
| 1:13107200 | 0.4 | 0.2 | 0.4 | 0.1 | 0.1 | 0.2 |
| 0 | 0.1 | 0.2 | 0.2 | 0.2 | 0.1 | 0.1 |

AAV DJ8 Cross Neutralization

Cross reaction: mice were injected with AAV-DJ8, serum samples were collected after each injection and subject to ELISA assay for testing anti-AAV-DJ, AAVrh10, and AAV2 mouse IgG. For the ELISA assay, the plates were coated with AAV-DJ, AAVrh10 or AAV2, then different serum dilutions were monitored for AAV-DJ8 reactivity.

TABLE 26

AAV-DJ binding after AAV-DJ8 injection

| | 1st injection | | | 2nd injection | | |
|---|---|---|---|---|---|---|
| Dilution | #1 | #2 | #3 | #4 | #5 | #6 |
| 1:50 | 1.1 | 1.1 | 0.7 | 1.1 | 0.8 | 1.1 |
| 1:400 | 0.3 | 1.2 | 0.1 | 1.3 | 1.0 | 1.0 |
| 1:3200 | 0.1 | 0.8 | 0.1 | 1.3 | 1.6 | 1.5 |
| 1:25600 | 0.1 | 0.2 | 0.0 | 0.4 | 1.3 | 0.8 |
| 1:204800 | 0.1 | 0.1 | 0.1 | 0.1 | 0.4 | 0.2 |
| 1:1638400 | 0.0 | 0.0 | 0.0 | 0.1 | 0.1 | 0.1 |
| 1:13107200 | 0.1 | 0.0 | 0.0 | 0.1 | 0.1 | 0.0 |
| 0 | 0.0 | 0.0 | 0.0 | 0.0 | 0.0 | 0.0 |
| | 3rd injection | | | 3 time point control | | |
| Dilution | #7 | #8 | #9 | #10 | #11 | #12 |
| 1:50 | 1.0 | 1.2 | 1.1 | 0.4 | 0.6 | 0.8 |
| 1:400 | 1.0 | 1.1 | 0.8 | 0.1 | 0.1 | 0.2 |
| 1:3200 | 1.6 | 1.6 | 1.5 | 0.1 | 0.1 | 0.1 |
| 1:25600 | 0.6 | 1.0 | 0.9 | 0.1 | 0.0 | 0.1 |
| 1:204800 | 0.2 | 0.2 | 0.2 | 0.0 | 0.0 | 0.1 |
| 1:1638400 | 0.1 | 0.1 | 0.1 | 0.0 | 0.0 | 0.0 |
| 1:13107200 | 0.0 | 0.0 | 0.1 | 0.0 | 0.0 | 0.0 |
| 0 | 0.0 | 0.0 | 0.0 | 0.0 | 0.1 | 0.0 |

TABLE 27

AAVrh10 binding after AAV-DJ8 injection

| | 1st injection | | | 2nd injection | | |
|---|---|---|---|---|---|---|
| Dilution | #1 | #2 | #3 | #4 | #5 | #6 |
| 1:50 | 0.6 | 1.1 | 0.6 | 1.1 | 0.8 | 0.9 |
| 1:400 | 0.2 | 1.1 | 0.2 | 1.0 | 1.3 | 1.1 |
| 1:3200 | 0.1 | 0.3 | 0.1 | 0.2 | 1.8 | 0.9 |
| 1:25600 | 0.1 | 0.1 | 0.1 | 0.1 | 1.0 | 0.2 |
| 1:204800 | 0.1 | 0.1 | 0.1 | 0.1 | 0.2 | 0.1 |
| 1:1638400 | 0.1 | 0.1 | 0.1 | 0.1 | 0.1 | 0.1 |
| 1:13107200 | 0.1 | 0.1 | 0.1 | 0.1 | 0.1 | 0.1 |
| 0 | 0.1 | 0.1 | 0.1 | 0.1 | 0.1 | 0.1 |

TABLE 27-continued

AAVrh10 binding after AAV-DJ8 injection

| | 3rd injection | | | 3 time point control | | |
|---|---|---|---|---|---|---|
| Dilution | #7 | #8 | #9 | #10 | #11 | #12 |
| 1:50 | 0.9 | 1.0 | 1.0 | 0.4 | 0.6 | 0.8 |
| 1:400 | 1.5 | 1.4 | 1.1 | 0.1 | 0.2 | 0.3 |
| 1:3200 | 1.2 | 1.3 | 1.4 | 0.1 | 0.1 | 0.1 |
| 1:25600 | 0.4 | 0.5 | 0.6 | 0.1 | 0.1 | 0.1 |
| 1:204800 | 0.1 | 0.1 | 0.2 | 0.1 | 0.1 | 0.1 |
| 1:1638400 | 0.1 | 0.1 | 0.1 | 0.1 | 0.1 | 0.1 |
| 1:13107200 | 0.1 | 0.1 | 0.1 | 0.1 | 0.1 | 0.1 |
| 0 | 0.1 | 0.1 | 0.1 | 0.1 | 0.1 | 0.1 |

TABLE 28

AAV2 binding after AAV-DJ8 injection

| | 1st injection | | | 2nd injection | | |
|---|---|---|---|---|---|---|
| Dilution | #1 | #2 | #3 | #4 | #5 | #6 |
| 1:50 | 0.5 | 0.9 | 0.4 | 0.8 | 0.9 | 1.0 |
| 1:400 | 0.2 | 0.3 | 0.1 | 0.5 | 0.7 | 0.8 |
| 1:3200 | 0.1 | 0.1 | 0.1 | 0.2 | 0.3 | 0.4 |
| 1:25600 | 0.1 | 0.1 | 0.1 | 0.1 | 0.1 | 0.1 |
| 1:204800 | 0.1 | 0.1 | 0.1 | 0.1 | 0.1 | 0.1 |
| 1:1638400 | 0.1 | 0.1 | 0.1 | 0.1 | 0.1 | 0.1 |
| 1:13107200 | 0.1 | 0.1 | 0.1 | 0.1 | 0.1 | 0.1 |
| 0 | 0.1 | 0.1 | 0.1 | 0.1 | 0.1 | 0.1 |
| | 3rd injection | | | 3 time point control | | |
| Dilution | #7 | #8 | #9 | #10 | #11 | #12 |
| 1:50 | 1.1 | 1.1 | 1.1 | 0.7 | 0.6 | 0.8 |
| 1:400 | 0.6 | 0.7 | 0.5 | 0.1 | 0.2 | 0.2 |
| 1:3200 | 0.2 | 0.2 | 0.1 | 0.1 | 0.1 | 0.1 |
| 1:25600 | 0.1 | 0.1 | 0.1 | 0.1 | 0.1 | 0.1 |
| 1:204800 | 0.1 | 0.1 | 0.1 | 0.1 | 0.1 | 0.1 |
| 1:1638400 | 0.1 | 0.1 | 0.1 | 0.1 | 0.1 | 0.1 |
| 1:13107200 | 0.1 | 0.1 | 0.1 | 0.1 | 0.1 | 0.1 |
| 0 | 0.1 | 0.1 | 0.1 | 0.1 | 0.1 | 0.1 |

AAVrh10-DJ8 Mix Cross Neutralization

Cross reaction: mice were injected with a mixture of AAVrh10-DJ8, serum samples were collected after each injection and subject to ELISA assay for testing anti-AAV-DJ, AAVrh10 and AAV2 mouse IgG. For the ELISA assay, the plates were coated with AAV-DJ, AAVrh10 or AAV2, then different serum dilutions were monitored for AAVrh10-DJ8 mix reactivity.

TABLE 29

AAV-DJ binding after AAVrh10-DJ8 mix injection

| | 1st injection | | | 2nd injection | | |
|---|---|---|---|---|---|---|
| Dilution | #1 | #2 | #3 | #4 | #5 | #6 |
| 1:50 | 0.7 | 0.5 | 0.5 | 0.5 | 0.5 | 0.5 |
| 1:400 | 1.0 | 1.2 | 1.3 | 0.8 | 1.3 | 1.2 |
| 1:3200 | 0.3 | 0.5 | 0.6 | 1.5 | 1.2 | 1.5 |
| 1:25600 | 0.1 | 0.1 | 0.2 | 0.6 | 0.4 | 0.5 |
| 1:204800 | 0.1 | 0.1 | 0.1 | 0.2 | 0.2 | 0.2 |
| 1:1638400 | 0.1 | 0.1 | 0.1 | 0.1 | 0.1 | 0.1 |
| 1:13107200 | 0.2 | 0.1 | 0.1 | 0.1 | 0.1 | 0.2 |
| 0 | 0.1 | 0.1 | 0.1 | 0.2 | 0.1 | 0.1 |

TABLE 29-continued

AAV-DJ binding after AAVrh10-DJ8 mix injection

| | 3rd injection | | | 3 time point control | | |
|---|---|---|---|---|---|---|
| Dilution | #7 | #8 | #9 | #10 | #11 | #12 |
| 1:50 | 0.5 | 0.5 | 0.6 | 0.5 | 0.4 | 0.8 |
| 1:400 | 0.9 | 1.3 | 0.8 | 0.5 | 0.1 | 0.2 |
| 1:3200 | 1.7 | 1.3 | 1.6 | 0.1 | 0.1 | 0.1 |
| 1:25600 | 0.8 | 0.6 | 0.7 | 0.3 | 0.1 | 0.1 |
| 1:204800 | 0.3 | 0.2 | 0.2 | 0.1 | 0.1 | 0.1 |
| 1:1638400 | 0.2 | 0.2 | 0.2 | 0.5 | 0.1 | 0.4 |
| 1:13107200 | 0.1 | 0.3 | 0.1 | 0.6 | 0.1 | 0.3 |
| 0 | 0.1 | 0.1 | 0.1 | 0.1 | 0.1 | 0.8 |

TABLE 30

AAVrh10 binding after AAVrh10-DJ8 mix injection

| | 1st injection | | | 2nd injection | | |
|---|---|---|---|---|---|---|
| Dilution | #1 | #2 | #3 | #4 | #5 | #6 |
| 1:50 | 1.2 | 0.8 | 0.7 | 0.7 | 0.6 | 0.7 |
| 1:400 | 0.8 | 1.3 | 1.9 | 1.4 | 1.9 | 1.9 |
| 1:3200 | 0.2 | 0.3 | 0.8 | 2.0 | 1.9 | 1.4 |
| 1:25600 | 0.1 | 0.1 | 0.2 | 0.7 | 0.5 | 0.3 |
| 1:204800 | 0.1 | 0.1 | 0.1 | 0.2 | 0.2 | 0.4 |
| 1:1638400 | 0.1 | 0.1 | 0.1 | 0.1 | 1.1 | 0.1 |
| 1:13107200 | 0.1 | 0.1 | 0.1 | 0.1 | 0.1 | 0.1 |
| 0 | 0.1 | 0.1 | 0.1 | 0.1 | 0.1 | 0.1 |

| | 3rd injection | | | 3 time point control | | |
|---|---|---|---|---|---|---|
| Dilution | #7 | #8 | #9 | #10 | #11 | #12 |
| 1:50 | 0.7 | 0.8 | 0.8 | 0.7 | 0.4 | 0.7 |
| 1:400 | 2.1 | 2.2 | 1.3 | 0.1 | 0.1 | 0.2 |
| 1:3200 | 1.9 | 1.3 | 1.5 | 0.2 | 0.1 | 0.1 |
| 1:25600 | 0.5 | 0.3 | 0.8 | 0.1 | 0.1 | 0.1 |
| 1:204800 | 0.2 | 0.1 | 0.2 | 0.1 | 0.1 | 0.1 |
| 1:1638400 | 0.1 | 0.1 | 0.1 | 0.1 | 0.1 | 0.1 |
| 1:13107200 | 0.1 | 0.1 | 0.1 | 0.1 | 0.1 | 0.1 |
| 0 | 0.1 | 0.1 | 0.1 | 0.1 | 0.1 | 0.1 |

TABLE 31

AAV2 binding after AAVrh10-DJ8 mix injection

| | 1st injection | | | 2nd injection | | |
|---|---|---|---|---|---|---|
| Dilution | #1 | #2 | #3 | #4 | #5 | #6 |
| 1:50 | 0.6 | 0.4 | 0.5 | 0.6 | 0.5 | 0.5 |
| 1:400 | 0.5 | 0.5 | 0.6 | 0.4 | 0.7 | 0.8 |
| 1:3200 | 0.2 | 0.2 | 0.2 | 0.7 | 0.6 | 0.3 |
| 1:25600 | 0.1 | 0.1 | 0.1 | 0.2 | 0.2 | 0.2 |
| 1:204800 | 0.1 | 0.1 | 0.1 | 0.1 | 0.1 | 0.1 |
| 1:1638400 | 0.1 | 0.1 | 0.1 | 0.1 | 0.1 | 0.1 |
| 1:13107200 | 0.1 | 0.1 | 0.1 | 0.1 | 0.2 | 0.1 |
| 0 | 0.1 | 0.1 | 0.1 | 0.1 | 0.1 | 0.2 |

| | 3rd injection | | | 3 time point control | | |
|---|---|---|---|---|---|---|
| Dilution | #7 | #8 | #9 | #10 | #11 | #12 |
| 1:50 | 0.5 | 0.6 | 0.7 | 0.8 | 0.5 | 0.9 |
| 1:400 | 0.4 | 0.7 | 0.6 | 0.1 | 0.1 | 0.3 |
| 1:3200 | 0.9 | 0.4 | 0.7 | 0.1 | 0.1 | 0.1 |
| 1:25600 | 0.3 | 0.1 | 0.2 | 0.1 | 0.1 | 0.1 |
| 1:204800 | 0.1 | 0.2 | 0.1 | 0.1 | 0.6 | 0.1 |
| 1:1638400 | 0.1 | 0.1 | 0.2 | 0.1 | 0.1 | 0.1 |
| 1:13107200 | 0.1 | 0.1 | 0.2 | 0.1 | 0.1 | 0.1 |
| 0 | 0.1 | 0.2 | 0.2 | 0.1 | 0.1 | 0.1 |

AAV9 Cross Neutralization

Cross reaction: mice were injected with AAV9 viruses, serum samples were collected after each injection and subject to ELISA assay for testing anti-AAV-DJ, AAVrh10 and AAV2 mouse IgG. For the ELISA assay, the plates were coated with AAV-DJ, AAVrh10 or AAV2, then different serum dilutions were monitored for AAV9 reactivity.

TABLE 32

AAV-DJ binding after AAV9 injection

| | 1st injection | | | 2nd injection | | |
|---|---|---|---|---|---|---|
| Dilution | #1 | #2 | #3 | #4 | #5 | #6 |
| 1:50 | 0.9 | 1.1 | 1.1 | 1.2 | 1.3 | 1.3 |
| 1:400 | 0.2 | 0.7 | 0.3 | 0.6 | 0.6 | 0.8 |
| 1:3200 | 0.1 | 0.2 | 0.1 | 0.2 | 0.2 | 0.2 |
| 1:25600 | 0.2 | 0.1 | 0.1 | 0.1 | 0.1 | 0.1 |
| 1:204800 | 0.1 | 0.1 | 0.1 | 0.1 | 0.1 | 0.1 |
| 1:1638400 | 0.1 | 0.1 | 0.1 | 0.1 | 0.1 | 0.1 |
| 1:13107200 | 0.1 | 0.1 | 0.1 | 0.1 | 0.1 | 0.1 |
| 0 | 0.1 | 0.1 | 0.1 | 0.1 | 0.1 | 0.1 |

| | 3rd injection | | | 3 time point control | | |
|---|---|---|---|---|---|---|
| Dilution | #7 | #8 | #9 | #10 | #11 | #12 |
| 1:50 | 1.4 | 1.3 | 1.3 | 0.2 | 0.1 | 0.2 |
| 1:400 | 0.5 | 0.6 | 0.7 | 0.1 | 0.1 | 0.1 |
| 1:3200 | 0.2 | 0.2 | 0.2 | 0.1 | 0.1 | 0.1 |
| 1:25600 | 0.1 | 0.1 | 0.1 | 0.1 | 0.1 | 0.1 |
| 1:204800 | 0.1 | 0.1 | 0.1 | 0.1 | 0.1 | 0.1 |
| 1:1638400 | 0.1 | 0.1 | 0.1 | 0.1 | 0.1 | 0.1 |
| 1:13107200 | 0.1 | 0.1 | 0.1 | 0.1 | 0.1 | 0.1 |
| 0 | 0.1 | 0.1 | 0.1 | 0.1 | 0.1 | 0.1 |

TABLE 33

AAVrh10 binding after AAV9 injection

| | 1st injection | | | 2nd injection | | |
|---|---|---|---|---|---|---|
| Dilution | #1 | #2 | #3 | #4 | #5 | #6 |
| 1:50 | 0.5 | 1.6 | 0.6 | 0.9 | 1.2 | 1.2 |
| 1:400 | 0.1 | 0.5 | 0.1 | 0.2 | 0.3 | 0.3 |
| 1:3200 | 0.1 | 0.1 | 0.1 | 0.1 | 0.1 | 0.1 |
| 1:25600 | 0.1 | 0.1 | 0.1 | 0.1 | 0.1 | 0.1 |
| 1:204800 | 0.1 | 0.1 | 0.1 | 0.1 | 0.1 | 0.1 |
| 1:1638400 | 0.1 | 0.1 | 0.1 | 0.1 | 0.1 | 0.1 |
| 1:13107200 | 0.1 | 0.1 | 0.1 | 0.1 | 0.1 | 0.1 |
| 0 | 0.1 | 0.1 | 0.1 | 0.1 | 0.1 | 0.1 |

| | 3rd injection | | | 3 time point control | | |
|---|---|---|---|---|---|---|
| Dilution | #7 | #8 | #9 | #10 | #11 | #12 |
| 1:50 | 1.0 | 0.9 | 1.0 | 0.1 | 0.1 | 0.2 |
| 1:400 | 0.3 | 0.3 | 0.2 | 0.1 | 0.1 | 0.1 |
| 1:3200 | 0.1 | 0.1 | 0.1 | 0.1 | 0.1 | 0.1 |
| 1:25600 | 0.1 | 0.1 | 0.1 | 0.1 | 0.1 | 0.1 |
| 1:204800 | 0.1 | 0.1 | 0.1 | 0.1 | 0.1 | 0.1 |
| 1:1638400 | 0.1 | 0.1 | 0.1 | 0.1 | 0.1 | 0.1 |
| 1:13107200 | 0.1 | 0.1 | 0.1 | 0.1 | 0.1 | 0.1 |
| 0 | 0.1 | 0.1 | 0.1 | 0.1 | 0.1 | 0.1 |

TABLE 34

AAV2 binding after AAV9 injection

| | 1st injection | | | 2nd injection | | |
|---|---|---|---|---|---|---|
| Dilution | #1 | #2 | #3 | #4 | #5 | #6 |
| 1:50 | 0.1 | 0.1 | 0.1 | 0.2 | 0.2 | 0.2 |
| 1:400 | 0.1 | 0.1 | 0.1 | 0.1 | 0.2 | 0.1 |
| 1:3200 | 0.2 | 0.1 | 0.1 | 0.1 | 0.1 | 0.1 |
| 1:25600 | 0.1 | 0.1 | 0.1 | 0.1 | 0.1 | 0.1 |
| 1:204800 | 0.1 | 0.1 | 0.1 | 0.1 | 0.1 | 0.1 |
| 1:1638400 | 0.1 | 0.1 | 0.1 | 0.1 | 0.1 | 0.1 |
| 1:13107200 | 0.1 | 0.1 | 0.1 | 0.1 | 0.1 | 0.1 |
| 0 | 0.1 | 0.1 | 0.1 | 0.1 | 0.1 | 0.1 |

| | 3rd injection | | | 3 time point control | | |
|---|---|---|---|---|---|---|
| Dilution | #7 | #8 | #9 | #10 | #11 | #12 |
| 1:50 | 0.4 | 0.2 | 0.2 | 0.1 | 0.3 | 0.2 |
| 1:400 | 0.1 | 0.1 | 0.1 | 0.1 | 0.1 | 0.1 |
| 1:3200 | 0.1 | 0.1 | 0.1 | 0.1 | 0.1 | 0.1 |
| 1:25600 | 0.1 | 0.1 | 0.1 | 0.1 | 0.1 | 0.1 |
| 1:204800 | 0.1 | 0.1 | 0.1 | 0.1 | 0.1 | 0.1 |
| 1:1638400 | 0.1 | 0.1 | 0.1 | 0.1 | 0.1 | 0.1 |
| 1:13107200 | 0.1 | 0.1 | 0.1 | 0.1 | 0.1 | 0.1 |
| 0 | 0.1 | 0.1 | 0.1 | 0.1 | 0.1 | 0.1 |

AAV DJ Cross Neutralization

Cross reaction: mice were injected with AAV-DJ viruses, serum samples were collected after each injection and subject to ELISA assay for testing anti-AAV-DJ, AAVrh10 and AAV2 mouse IgG. For the ELISA assay, the plates were coated with AAV-DJ mouse IgG, AAVrh10 or AAV2, then different serum dilutions were monitored for AAV-DJ reactivity.

TABLE 35

AAVrh10 binding after AAV-DJ injection

| | 1st injection | | | 2nd injection | | |
|---|---|---|---|---|---|---|
| Dilution | #1 | #2 | #3 | #4 | #5 | #6 |
| 1:50 | 0.8 | 0.2 | 0.8 | 1.6 | 1.5 | 1.6 |
| 1:400 | 0.2 | 0.1 | 0.2 | 1.3 | 1.7 | 1.3 |
| 1:3200 | 0.1 | 0.1 | 0.1 | 0.4 | 1.1 | 0.4 |
| 1:25600 | 0.1 | 0.1 | 0.1 | 0.1 | 0.3 | 0.2 |
| 1:204800 | 0.1 | 0.1 | 0.1 | 0.1 | 0.2 | 0.1 |
| 1:1638400 | 0.1 | 0.1 | 0.1 | 0.1 | 0.1 | 0.1 |
| 1:13107200 | 0.1 | 0.1 | 0.1 | 0.1 | 0.1 | 0.1 |
| 0 | 0.1 | 0.1 | 0.1 | 0.1 | 0.1 | 0.1 |

| | 3rd injection | | | 3 time point control | | |
|---|---|---|---|---|---|---|
| Dilution | #7 | #8 | #9 | #10 | #11 | #12 |
| 1:50 | 1.8 | 1.8 | 1.8 | 0.1 | 0.2 | 0.3 |
| 1:400 | 1.7 | 1.7 | 1.6 | 0.1 | 0.1 | 0.1 |
| 1:3200 | 0.8 | 1.0 | 1.4 | 0.1 | 0.1 | 0.1 |
| 1:25600 | 0.3 | 0.3 | 0.6 | 0.1 | 0.1 | 0.1 |
| 1:204800 | 0.2 | 0.2 | 0.5 | 0.1 | 0.1 | 0.1 |
| 1:1638400 | 0.1 | 0.1 | 0.3 | 0.1 | 0.1 | 0.1 |
| 1:13107200 | 0.1 | 0.1 | 0.3 | 0.1 | 0.1 | 0.1 |
| 0 | 0.1 | 0.1 | 0.1 | 0.1 | 0.1 | 0.1 |

TABLE 36

AAV2 binding after AAV-DJ injection

| | 1st injection | | | 2nd injection | | |
|---|---|---|---|---|---|---|
| Dilution | #1 | #2 | #3 | #4 | #5 | #6 |
| 1:50 | 0.7 | 0.7 | 0.7 | 0.9 | 0.7 | 0.9 |
| 1:400 | 0.3 | 0.2 | 0.5 | 0.9 | 0.8 | 0.9 |
| 1:3200 | 0.1 | 0.1 | 0.2 | 0.4 | 0.6 | 0.6 |
| 1:25600 | 0.1 | 0.1 | 0.1 | 0.2 | 0.3 | 0.3 |
| 1:204800 | 0.1 | 0.1 | 0.1 | 0.1 | 0.2 | 0.2 |
| 1:1638400 | 0.1 | 0.1 | 0.1 | 0.1 | 0.1 | 0.1 |
| 1:13107200 | 0.1 | 0.1 | 0.1 | 0.1 | 0.1 | 0.1 |
| 0 | 0.1 | 0.1 | 0.1 | 0.1 | 0.1 | 0.1 |

| | 3rd injection | | | 3 time point control | | |
|---|---|---|---|---|---|---|
| Dilution | #7 | #8 | #9 | #10 | #11 | #12 |
| 1:50 | 0.9 | 0.7 | 0.9 | 0.1 | 0.1 | 0.1 |
| 1:400 | 0.9 | 0.8 | 0.8 | 0.1 | 0.1 | 0.1 |
| 1:3200 | 0.5 | 0.6 | 0.9 | 0.1 | 0.1 | 0.1 |
| 1:25600 | 0.2 | 0.3 | 0.4 | 0.1 | 0.1 | 0.1 |
| 1:204800 | 0.1 | 0.1 | 0.2 | 0.1 | 0.1 | 0.1 |
| 1:1638400 | 0.1 | 0.1 | 0.2 | 0.1 | 0.1 | 0.1 |
| 1:13107200 | 0.1 | 0.1 | 0.2 | 0.1 | 0.1 | 0.1 |
| 0 | 0.1 | 0.1 | 0.1 | 0.1 | 0.1 | 0.1 |

TABLE 37

AAV-DJ mouse IgG binding after AAV-DJ injection

| | 1st injection | | | 2nd injection | | |
|---|---|---|---|---|---|---|
| Dilution | #1 | #2 | #3 | #4 | #5 | #6 |
| 1:50 | 1.1 | 1.1 | 1.0 | 0.9 | 0.8 | 1.0 |
| 1:400 | 0.9 | 0.8 | 1.2 | 1.4 | 1.1 | 1.2 |
| 1:3200 | 0.3 | 0.3 | 0.6 | 1.2 | 1.4 | 1.3 |
| 1:25600 | 0.2 | 0.1 | 0.3 | 0.8 | 1.1 | 0.8 |
| 1:204800 | 0.1 | 0.1 | 0.2 | 0.4 | 0.7 | 0.5 |
| 1:1638400 | 0.1 | 0.1 | 0.1 | 0.3 | 0.5 | 0.3 |
| 1:13107200 | 0.1 | 0.1 | 0.1 | 0.3 | 0.5 | 0.3 |
| 0 | 0.1 | 0.1 | 0.1 | 0.1 | 0.1 | 0.2 |

| | 3rd injection | | | 3 time point control | | |
|---|---|---|---|---|---|---|
| Dilution | #7 | #8 | #9 | #10 | #11 | #12 |
| 1:50 | 0.9 | 0.9 | 0.8 | 0.1 | 0.2 | 0.2 |
| 1:400 | 1.4 | 1.3 | 1.1 | 0.1 | 0.1 | 0.1 |
| 1:3200 | 1.4 | 1.4 | 1.5 | 0.1 | 0.1 | 0.1 |
| 1:25600 | 0.8 | 0.8 | 1.3 | 0.1 | 0.1 | 0.1 |
| 1:204800 | 0.8 | 0.6 | 1.2 | 0.1 | 0.1 | 0.1 |
| 1:1638400 | 0.7 | 0.6 | 1.1 | 0.1 | 0.1 | 0.1 |
| 1:13107200 | 0.4 | 0.5 | 0.7 | 0.1 | 0.1 | 0.1 |
| 0 | 0.3 | 0.3 | 0.2 | 0.1 | 0.1 | 0.1 |

These cross-reaction studies demonstrated that administration of any AAV capsid always induces a strong antibody response to itself, though the strength of this response can vary drastically. Further, capsid responses are mutual, meaning that if a first AAV capsid induces a response to a second, the second will necessarily induce an independent response to the first, of the same magnitude. These assays provide data for grouping of AAV capsids into immunologically-related or non-related populations. Understanding these relationships is critical for AAV-repeat dosing administration paradigms, wherein immunologically non-related capsids should be used to avoid neutralizing antibody responses.

Table 38 summarizes the data of Example 9 by detailing the paired response or cross reactivity between AAV pairs. The table lists first the AAV which is contacted with serum in the assay or which would be administered in a subject, "Administered AAV." Where such administered AAVs are cross reactive with a second AAV, meaning that antibodies are generated to the second AAV when the first AAV is administered, the average binding is given for the first three dilutions in the table.

Average binding values for each cross reactive AAV pair were calculated based on the average of samples 1 thru 9 as shown in Tables 17-37, at each respective dilution. Based on the average binding values at the 1:50 dilution, the most cross-reactive pair of AAVs is AAVDJ and AAVrh10 (1:50 dilution average=1.3), and the least cross-reactive pair is AAV9 and AAV2 (1:50 dilution average=0.2). AAV pairs are listed as the AAV injected, i.e., Administered AAV, followed by the AAV used for testing of cross-reactivity, i.e., Binding AAV. Other cross reactive AAV pairs, listed in order of least cross-reactive to most cross-reactive as based on the average binding values at 1:50 dilution (and subsequently the 1:400 dilutions if needed), are as follows, AAV6 and AAVrh10 (0.3), AAV6 and AAV2 (0.4), AAV6 and AAVDJ (0.5), AAV2 and AAVrh10 (0.5), AAVrh10/DJ8 mix and AAV2 (0.5), AAVrh10/DJ8 mix and AAVDJ (0.5), AAV2 and AAV2 ms IgG (0.6), AAVrh10 and AAV2 (0.8), AAVDJ and AAV2 (0.8), AAVrh10/DJ8 mix and AAVrh10 (0.8), AAVDJ8 and AAV2 (0.9), AAVDJ8 and AAVrh10 (0.9), AAV2 and AAVDJ (0.9), AAVDJ and AAVDJ ms IgG (0.9), AAV9 and AAVrh10 (1.0), AAVDJ8 and AAVDJ (1.0), AAVrh10 and AAVDJ (1.1), AAV9 and AAVDJ (1.2), AAVrh10 and AAVrh10 ms IgG (1.2).

TABLE 38

Cross-reactivity of AAV pairs

| Administered AAV | Binding AAV | Avg binding at 1:50 dilution | Avg binding at 1:400 dilution | Avg binding at 1:3200 dilution |
|---|---|---|---|---|
| AAV2 | AAVDJ | 0.9 | 1.0 | 0.7 |
| AAV2 | AAV2 ms IgG | 0.6 | 0.4 | 0.7 |
| AAV2 | AAVrh10 | 0.5 | 0.4 | 0.1 |
| AAV6 | AAVDJ | 0.5 | 0.2 | 0.1 |
| AAV6 | AAV2 | 0.4 | 0.2 | 0.1 |
| AAV6 | AAVrh10 | 0.3 | 0.2 | 0.1 |
| AAVrh10 | AAVrh10 ms IgG | 1.2 | 1.4 | 1.7 |
| AAVrh10 | AAVDJ | 1.1 | 0.7 | 0.4 |
| AAVrh10 | AAV2 | 0.8 | 0.3 | 0.1 |
| AAVDJ8 | AAVDJ | 1.0 | 0.9 | 1.1 |
| AAVDJ8 | AAVrh10 | 0.9 | 1.0 | 0.8 |

TABLE 38-continued

Cross-reactivity of AAV pairs

| Administered AAV | Binding AAV | Avg binding at 1:50 dilution | Avg binding at 1:400 dilution | Avg binding at 1:3200 dilution |
|---|---|---|---|---|
| AAVDJ8 | AAV2 | 0.9 | 0.5 | 0.2 |
| AAVrh10/DJ8 mix | AAVrh10 | 0.8 | 1.6 | 1.3 |
| AAVrh10/DJ8 mix | AAVDJ | 0.5 | 1.1 | 1.1 |
| AAVrh10/DJ8 mix | AAV2 | 0.5 | 0.6 | 0.5 |
| AAV9 | AAVDJ | 1.2 | 0.6 | 0.2 |
| AAV9 | AAVrh10 | 1.0 | 0.3 | 0.1 |
| AAV9 | AAV2 | 0.2 | 0.1 | 0.1 |
| AAVDJ | AAVrh10 | 1.3 | 1.1 | 0.6 |
| AAVDJ | AAVDJ ms IgG | 0.9 | 1.2 | 1.0 |
| AAVDJ | AAV2 | 0.8 | 0.7 | 0.4 |

Example 10: AAV Serotype Neutralizing Antibody Screening in Normal Human Serum (NHS) (1$^{st}$ Cohort)

32 human serum samples (assigned as the first test cohort) derived from Discovery Life Science (Los Osos, Calif., USA) were tested for AAV serotype neutralizations. All donors were 19-62 years old; both female and male donors were included.

AAV-DJ Neutralizing Activity in Normal Human Serum (NHS)

Using the same test protocol as discussed in Example 2, human sera were screened for neutralizing antibodies. Similarly, Hela S3 cells were seeded at 10,000/well in a 96-well plate; maintained in Dulbecco's modified Eagle medium (DMEM) supplemented with 10% FBS (fetal bovine serum); and cultured overnight to reach a density of about 20,000/well. AAV-DJ viruses at MOI (multiplicity of infection) $10^4$ were pre-incubated with diluted human sera at a ratio of 1:16, 1:64, 1:256, or 1:4096, for 1 hour at 37° C. 32 human samples were tested. The mixture was added to the culture plate with Hela S3 cells and incubated for 3 days. At the same time, control samples were set up in parallel. After 72 hours of incubation, cells were harvested and analyzed by flow cytometry. Previous identified NHP samples with high and low neutralizing activity were used as controls to establish cut-off for the AAV-DJ assay. The assay cut-off is at 30%. For the control samples shown in Table 39, PC control indicates a sample for which level of neutralization was determined in a previous experiment, whereas NC is a sample wherein there is an absence of neutralization.

TABLE 39

AAV DJ neutralizing assay in human serum samples (MOI $10^4$) (1$^{st}$ cohort)

| | Samples (data given as %) | | | | | | | |
|---|---|---|---|---|---|---|---|---|
| Dilution | #1 | #2 | #3 | #4 | #5 | #6 | #7 | #8 |
| 1:16 | 0.9 | 1.1 | 18.8 | 3.0 | 2.5 | 3.9 | 60.0 | 39.9 |
| 1:64 | 2.1 | 37.9 | 64.2 | 1.7 | 0.7 | 1.2 | 73.4 | 56.9 |
| 1:256 | 1.7 | 74.2 | 74.1 | 25.0 | 1.6 | 16.4 | 71.8 | 54.3 |
| 1:4096 | 75.7 | 76.3 | 75.1 | 70.7 | 30.5 | 69.2 | 69.7 | 53.8 |
| | #9 | #10 | #11 | #12 | #13 | #14 | #15 | #16 |
| 1:16 | 0.7 | 84.8 | 5.0 | 89.1 | 83.2 | 4.7 | 78.0 | 46.0 |
| 1:64 | 1.9 | 82.9 | 13.3 | 81.8 | 78.2 | 1.6 | 72.6 | 52.8 |
| 1:256 | 46.2 | 72.3 | 64.1 | 74.3 | 73.0 | 3.4 | 65.8 | 50.3 |
| 1:4096 | 61.7 | 59.0 | 60.2 | 57.9 | 59.5 | 44.7 | 51.8 | 44.1 |

TABLE 39-continued

AAV DJ neutralizing assay in human serum samples (MOI $10^4$) ($1^{st}$ cohort)

| | #17 | #18 | #19 | #20 | #21 | #22 | #23 | #24 |
|---|---|---|---|---|---|---|---|---|
| 1:16 | 65.7 | 1.3 | 0.4 | 0.7 | 1.0 | 43.8 | 0.7 | 1.3 |
| 1:64 | 70.6 | 0.8 | 0.6 | 3.0 | 0.6 | 66.9 | 0.5 | 12.8 |
| 1:256 | 70.1 | 3.7 | 1.4 | 37.6 | 2.3 | 66.2 | 2.2 | 36.3 |
| 1:4096 | 68.3 | 63.8 | 45.5 | 64.7 | 56.5 | 67.9 | 59.1 | 49.4 |
| | #25 | #26 | #27 | #28 | #29 | #30 | #31 | #32 |
| 1:16 | 81.7 | 81.9 | 26.2 | 84.8 | 0.6 | 0.6 | 0.7 | 62.6 |
| 1:64 | 76.0 | 70.7 | 59.5 | 71.4 | 0.9 | 0.8 | 0.8 | 51.1 |
| 1:256 | 68.2 | 68.3 | 63.2 | 58.0 | 17.9 | 0.9 | 3.4 | 47.2 |
| 1:4096 | 53.4 | 51.6 | 50.5 | 51.3 | 49.1 | 3.8 | 41.3 | 36.7 |
| | ctl PC | ctl PC | ctl NC | ctl NC | ctl PC | ctl PC | ctl NC | ctl NC |
| 1:16 | 0.6 | 0.5 | 77.2 | 60.9 | 0.7 | 1.4 | 55.7 | 46.9 |
| 1:64 | 0.9 | 0.6 | 82.8 | 79.8 | 1.0 | 5.2 | 74.7 | 71.5 |
| 1:256 | 2.7 | 12.1 | 80.9 | 78.2 | 5.5 | 43.8 | 72.0 | 69.4 |
| 1:4096 | 37.1 | 70.4 | 80.2 | 76.2 | 40.0 | 67.4 | 70.2 | 68.3 |

Figure 2A:
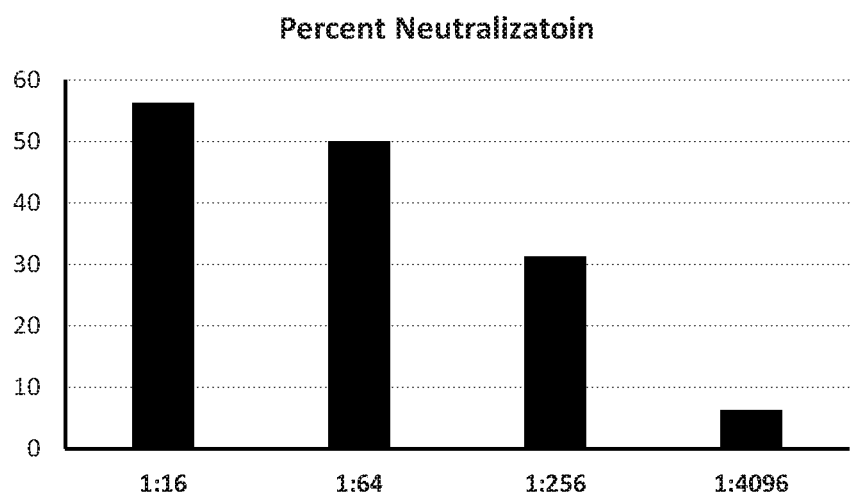
FIG. 2A shows the frequency of AAV-DJ neutralization in normal human subjects (Pt study cohort).

Among 32 human samples tested, 56% shows neutralizing activity at 1:16 dilution, 50% at 1:64 dilution, 31% at 1:256 dilution and only 6.2% at 1:4096 dilution (FIG. 2A)

AAV2 Neutralizing Antibody Screening in Normal Human Serum (NHS)

Using the same test protocol as discussed in Example 2, human sera were screened for neutralizing antibodies. Similarly, Hela S3 cells were seeded at 10,000/well in a 96-well plate; maintained in Dulbecco's modified Eagle medium (DMEM) supplemented with 10% FBS (fetal bovine serum); and cultured overnight to reach a density of about 20,000/well. AAV2 viruses at MOI (multiplicity of infection) $10^4$ were pre-incubated with diluted human sera at a ratio of 1:16, 1:64, 1:256, or 1:4096, for 1 hour at 37° C. 32 human samples were tested. The mixture was added to the culture plate with Hela S3 cells and incubated for 3 days. At the same time, control samples were set up in parallel. After 72 hours of incubation, cells were harvested and analyzed by flow cytometry. The assay cut-off is at 48%.

TABLE 40

AAV2 neutralizing assay in human serum samples (MOI $10^4$) ($1^{st}$ cohort)

| | Samples (data given as %) | | | | | | | |
|---|---|---|---|---|---|---|---|---|
| Dilution | #1 | #2 | #3 | #4 | #5 | #6 | #7 | #8 |
| 1:16 | 0.4 | 0.1 | 0.4 | 0.7 | 0.2 | 0.3 | 91.1 | 24.1 |
| 1:64 | 0.5 | 2.9 | 0.2 | 0.2 | 0.1 | 0.2 | 91.7 | 88.0 |
| 1:256 | 0.3 | 63.8 | 0.8 | 0.9 | 0.2 | 0.6 | 92.1 | 92.4 |
| 1:4096 | 55.2 | 91.2 | 71.3 | 82.6 | 3.8 | 74.1 | 91.7 | 92.0 |
| | #9 | #10 | #11 | #12 | #13 | #14 | #15 | #16 |
| 1:16 | 0.3 | 79.7 | 0.2 | 82.4 | 87.8 | 0.1 | 89.1 | 69.0 |
| 1:64 | 0.5 | 87.0 | 0.5 | 89.9 | 89.5 | 0.2 | 93.0 | 94.3 |
| 1:256 | 0.6 | 93.4 | 42.0 | 91.8 | 92.8 | 0.8 | 92.3 | 93.5 |
| 1:4096 | 79.7 | 93.3 | 92.6 | 92.9 | 93.2 | 81.6 | 92.3 | 93.2 |
| | #17 | #18 | #19 | #20 | #21 | #22 | #23 | #24 |
| 1:16 | 89.9 | 0.3 | 0.6 | 1.1 | 0.1 | 90.1 | 0.3 | 0.7 |
| 1:64 | 90.5 | 0.3 | 0.6 | 6.5 | 0.3 | 87.5 | 0.3 | 0.8 |
| 1:256 | 93.0 | 0.5 | 0.6 | 72.9 | 0.3 | 91.6 | 0.5 | 42.7 |
| 1:4096 | 92.0 | 59.2 | 17.7 | 90.2 | 63.3 | 92.1 | 69.3 | 89.1 |

TABLE 40-continued

AAV2 neutralizing assay in human serum samples (MOI $10^4$) ($1^{st}$ cohort)

| | #25 | #26 | #27 | #28 | #29 | #30 | #31 | #32 |
|---|---|---|---|---|---|---|---|---|
| 1:16 | 88.3 | 3.7 | 0.5 | 92.1 | 0.5 | 0.8 | 0.7 | 79.8 |
| 1:64 | 90.9 | 62.1 | 2.1 | 91.9 | 1.6 | 0.3 | 0.4 | 92.9 |
| 1:256 | 91.6 | 87.8 | 63.7 | 93.0 | 9.4 | 0.7 | 0.7 | 94.2 |
| 1:4096 | 92.5 | 90.3 | 90.7 | 92.3 | 88.9 | 1.8 | 79.5 | 93.9 |

Figure 2B:
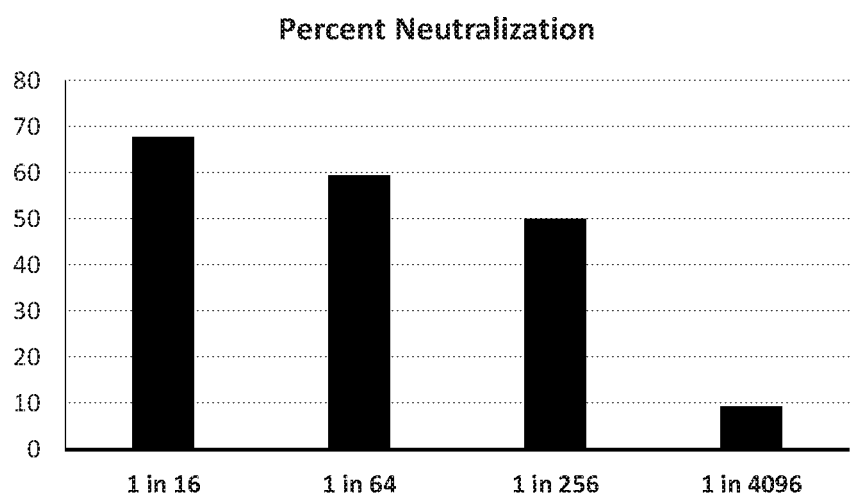
FIG. 2B shows the frequency of AAV2 neutralization in normal human subjects (1$^{st}$ study cohort).
Figure 2C:
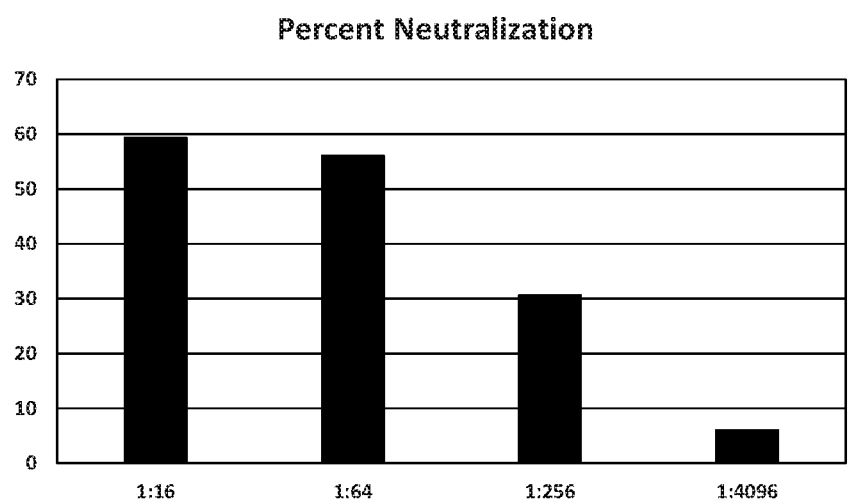
FIG. 2C shows the frequency of AAV1 neutralization in normal human subjects (1$^{st}$ study cohort).
Figure 2D:
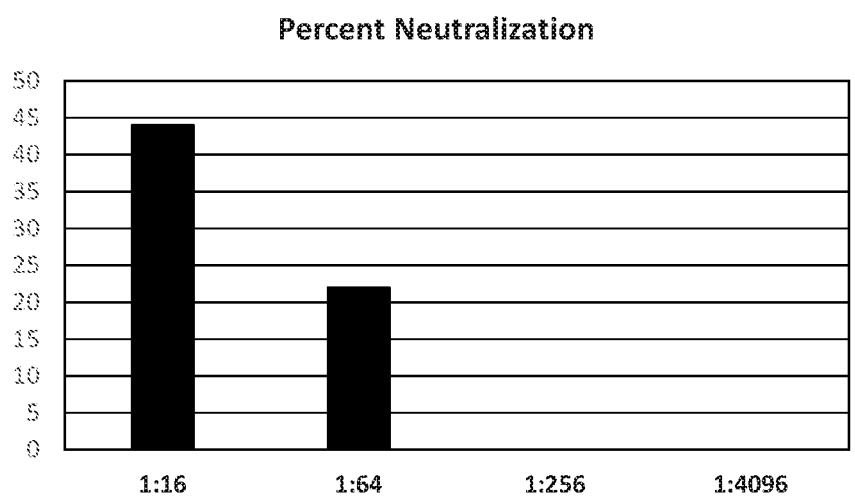
FIG. 2D shows the frequency of AAVrh10 neutralization in normal human subjects (1$^{st}$ study cohort).
Figure 3A:
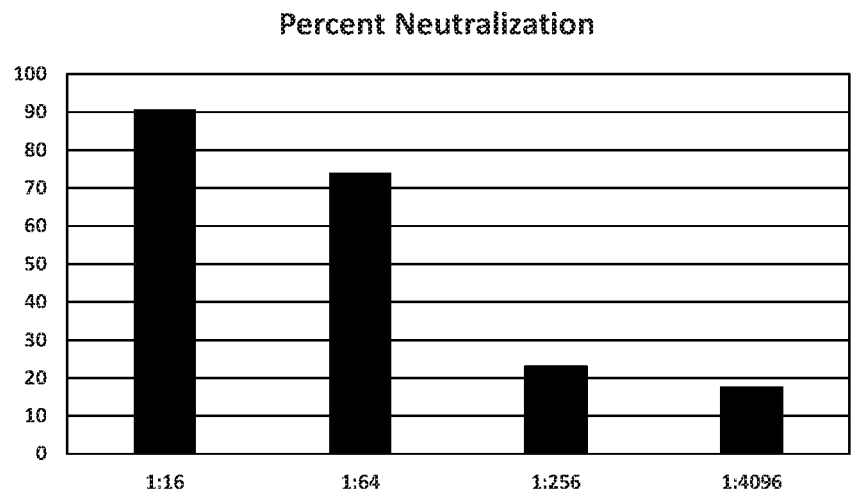
FIG. 3A shows the frequency of AAV-DJ neutralization in normal human subjects (2$^{nd}$ study cohort).
Figure 3B:
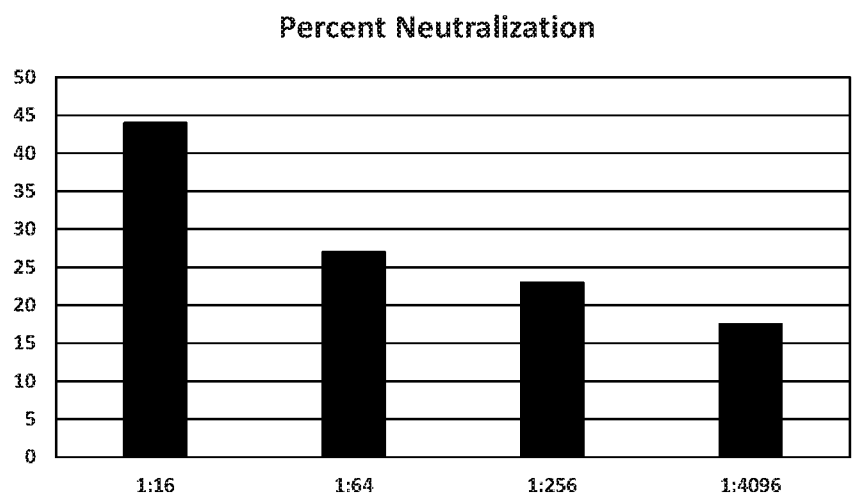
FIG. 3B shows the frequency of AAV1 neutralization in normal human subjects (2$^{nd}$ study cohort).
Figure 3C:
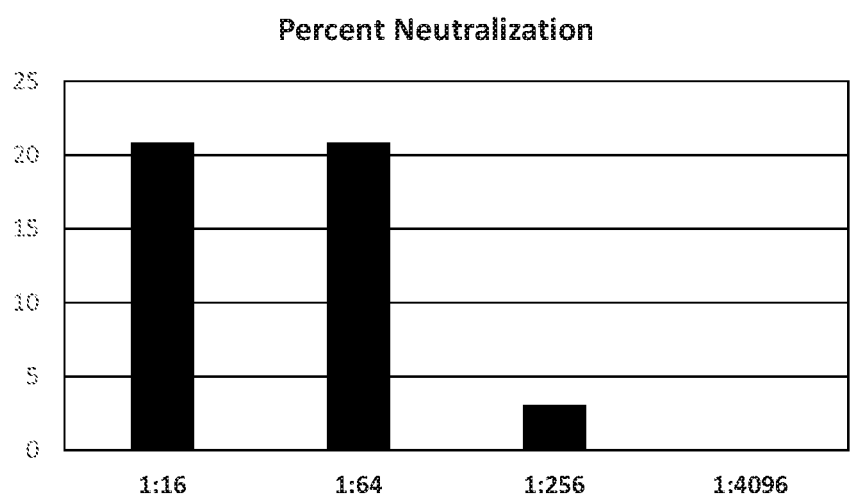
FIG. 3C the frequency of AAVrh10 neutralization in normal human subjects (2$^{nd}$ study cohort).

Among 32 human samples tested, 67.7% shows neutralizing activity at 1:16 dilution, 59.4% at 1:64 dilution, 50% at 1:256 dilution and only 9.4% at 1:4096 dilution (FIG. 2B).

As compared to AAV-DJ neutralizing titers in human serum sample, AAV2 does not score much higher than AAV-DJ in the ratio of neutralizing donors. However, AAV2 generally has a higher neutralizing titer.

AAV1 Neutralizing Antibody Screening in Normal Human Serum (NHS)

Using the same test protocol as discussed in Example 2, human sera were screened for neutralizing antibodies. Similarly, Hela S3 cells were seeded at 10,000/well in a 96-well plate; maintained in Dulbecco's modified Eagle medium (DMEM) supplemented with 10% FBS (fetal bovine serum); and cultured overnight to reach a density of about 20,000/well. AAV1 viruses at MOI (multiplicity of infection) $10^4$ were pre-incubated with diluted human sera at a ratio of 1:16, 1:64, 1:256, or 1:4096, for 1 hour at 37° C. 32 human samples were tested. The mixture was added to the culture plate with Hela S3 cells and incubated for 3 days. At the same time, control samples were set up in parallel. After 72 hours of incubation, cells were harvested and analyzed by flow cytometry. The assay cut-off is at 17%.

TABLE 41

AAV1 neutralizing assay in human serum samples (MOI $10^4$) ($1^{st}$ cohort)

| | Samples (data given as %) | | | | | | | |
|---|---|---|---|---|---|---|---|---|
| Dilution | #1 | #2 | #3 | #4 | #5 | #6 | #7 | #8 |
| 1:16 | 0.2 | 0.3 | 3.0 | 0.3 | 0.5 | 0.3 | 33.6 | 32.0 |
| 1:64 | 0.1 | 10.6 | 20.9 | 4.0 | 0.0 | 0.1 | 32.0 | 32.0 |

TABLE 41-continued

AAV1 neutralizing assay in human serum samples (MOI 10⁴) (1st cohort)

| | | | | | | | | |
|---|---|---|---|---|---|---|---|---|
| 1:256 | 1.5 | 25.1 | 25.1 | 21.0 | 0.0 | 9.6 | 29.6 | 31.4 |
| 1:4096 | 25.0 | 30.8 | 29.2 | 27.5 | 19.0 | 29.7 | 29.9 | 30.1 |

| | #9 | #10 | #11 | #12 | #13 | #14 | #15 | #16 |
|---|---|---|---|---|---|---|---|---|
| 1:16 | 0.7 | 26.8 | 1.0 | 34.1 | 36.0 | 0.1 | 29.8 | 21.3 |
| 1:64 | 0.4 | 32.3 | 8.8 | 35.4 | 35.3 | 0.0 | 33.1 | 29.1 |
| 1:256 | 12.9 | 29.1 | 23.4 | 30.5 | 29.3 | 1.0 | 28.9 | 31.3 |
| 1:4096 | 32.1 | 32.5 | 33.3 | 33.7 | 35.1 | 27.1 | 32.9 | 35.6 |

| | #17 | #18 | #19 | #20 | #21 | #22 | #23 | #24 |
|---|---|---|---|---|---|---|---|---|
| 1:16 | 35.7 | 0.7 | 0.1 | 0.3 | 0.2 | 32.6 | 0.3 | 0.5 |
| 1:64 | 36.7 | 0.4 | 0.2 | 1.9 | 0.1 | 34.0 | 0.7 | 6.2 |
| 1:256 | 29.1 | 1.9 | 0.1 | 17.1 | 0.8 | 30.4 | 0.8 | 25.9 |
| 1:4096 | 33.7 | 26.2 | 20.0 | 31.1 | 27.2 | 32.2 | 26.4 | 35.4 |

| | #25 | #26 | #27 | #28 | #29 | #30 | #31 | #32 |
|---|---|---|---|---|---|---|---|---|
| 1:16 | 38.3 | 35.5 | 0.8 | 41.8 | 0.5 | 0.5 | 0.2 | 40.7 |
| 1:64 | 38.2 | 37.5 | 17.6 | 37.2 | 1.3 | 0.1 | 0.1 | 37.1 |
| 1:256 | 30.5 | 30.3 | 29.6 | 32.2 | 11.2 | 0.2 | 1.2 | 33.7 |
| 1:4096 | 38.4 | 38.4 | 37.5 | 37.5 | 35.7 | 27.6 | 29.4 | 37.6 |

AAVrh10 Neutralizing Antibody Screening in Normal Human Serum (NHS)

Using the same test protocol as discussed in Example 2, human sera were screened for neutralizing antibodies. Similarly, Hela S3 cells were seeded at 10,000/well in a 96-well plate; maintained in Dulbecco's modified Eagle medium (DMEM) supplemented with 10% FBS (fetal bovine serum); and cultured overnight to reach a density of about 20,000/well. AAVrh10 viruses at MOI (multiplicity of infection) $10^5$ were pre-incubated with diluted human sera at a ratio of 1:16, 1:64, 1:256, or 1:4096, for 1 hour at 37° C. 32 human samples were tested. The mixture was added to the culture plate with Hela S3 cells and incubated for 3 days. At the same time, control samples were set up in parallel. After 72 hours of incubation, cells were harvested and analyzed by flow cytometry. The assay cut-off is 25%.

TABLE 42

AAVrh10 neutralizing assay in human serum samples (MOI $10^{\times 5}$) (1st cohort)

| | Samples (data given as %) | | | | | | | |
|---|---|---|---|---|---|---|---|---|
| Dilution | #1 | #2 | #3 | #4 | #5 | #6 | #7 | #8 |
| 1:16 | 1.2 | 38.1 | 40.0 | 29.9 | 1.1 | 21.1 | 44.9 | 43.2 |
| 1:64 | 32.4 | 46.9 | 47.8 | 44.7 | 16.4 | 44.3 | 46.6 | 44.1 |
| 1:256 | 46.9 | 48.0 | 48.1 | 48.5 | 39.3 | 47.1 | 51.5 | 47.0 |
| 1:4096 | 48.8 | 49.0 | 48.3 | 50.0 | 49.2 | 50.2 | 49.4 | 46.3 |

| | #9 | #10 | #11 | #12 | #13 | #14 | #15 | #16 |
|---|---|---|---|---|---|---|---|---|
| 1:16 | 16.1 | 46.1 | 44.9 | 49.7 | 50.3 | 1.6 | 49.3 | 45.1 |
| 1:64 | 42.0 | 49.5 | 49.7 | 51.5 | 52.0 | 29.5 | 48.8 | 45.3 |
| 1:256 | 45.7 | 47.7 | 46.7 | 47.5 | 48.6 | 43.0 | 47.9 | 45.2 |
| 1:4096 | 48.8 | 47.0 | 47.7 | 48.7 | 47.6 | 48.7 | 50.9 | 49.6 |

| | #17 | #18 | #19 | #20 | #21 | #22 | #23 | #24 |
|---|---|---|---|---|---|---|---|---|
| 1:16 | 48.7 | 4.0 | 0.4 | 22.1 | 1.6 | 45.3 | 1.7 | 29.4 |
| 1:64 | 50.0 | 33.4 | 10.8 | 44.4 | 27.9 | 47.6 | 26.5 | 44.4 |
| 1:256 | 50.9 | 46.7 | 37.7 | 48.5 | 45.1 | 50.5 | 45.1 | 48.1 |
| 1:4096 | 52.8 | 49.2 | 51.7 | 52.0 | 52.8 | 52.5 | 50.2 | 49.6 |

TABLE 42-continued

AAVrh10 neutralizing assay in human serum samples (MOI $10^{\times 5}$) (1st cohort)

| | #25 | #26 | #27 | #28 | #29 | #30 | #31 | #32 |
|---|---|---|---|---|---|---|---|---|
| 1:16 | 54.1 | 53.2 | 45.6 | 58.4 | 20.0 | 0.3 | 0.8 | 47.4 |
| 1:64 | 52.1 | 52.6 | 49.5 | 55.3 | 45.7 | 13.7 | 29.3 | 46.8 |
| 1:256 | 48.1 | 48.7 | 47.7 | 50.0 | 46.4 | 40.6 | 42.9 | 47.2 |
| 1:4096 | 46.6 | 46.5 | 46.7 | 46.3 | 46.8 | 48.3 | 47.4 | 47.6 |

| | control | control |
|---|---|---|
| 1:16 | 50.4 | 50.2 |
| 1:64 | 50.6 | 52.0 |
| 1:256 | 50.9 | 50.9 |
| 1:4096 | 49.5 | 53.2 |

Comparison in neutralization of AAV-DJ, AAV2, AAV1 and AAVrh10 in human samples from California tested (as shown in Tables 39-42), suggests that stronger neutralizers (individuals) have titers that are capable of neutralization across AAV serotypes. Among 32 subjects tested, 2 have very high concentration of neutralizing antibodies against AAV-DJ, which exhibit complete neutralizing activity at 1:4096 dilution; 3 subjects exhibit complete neutralizing activity against AAV2 at 1:4096 dilution; and 2 subjects exhibit near complete neutralizing activity against AAV1 at 1:4096 dilution.

It is also observed that at 1:16 dilution, about 56% of subjects tested exhibit neutralizing activity to AAV-DJ; about 67% of subjects tested can neutralize AAV2; and about 60% subjects tested can neutralize AAV1. In general the neutralization rate and strength to AAVrh10 is much lower among the tested donors.

Example 11: AAV Serotypes Neutralizing Antibody Screening in Normal Human Serum (NHS) (2nd Cohort)

In this second test cohort, 34 human serum samples derived from Research Blood Components (Boston, Mass., USA) were tested for AAV serotype neutralizations. The same protocol as Example 10 was used to study neutralization activity in normal human subjects.

In general, Hela S3 cells were seeded at 10,000/well in a 96-well plate; maintained in Dulbecco's modified Eagle medium (DMEM) supplemented with 10% FBS (fetal bovine serum); and cultured overnight to reach a density of about 20,000/well. AAV viruses at a MOI (multiplicity of infection) $10^4$ were pre-incubated with diluted human sera at a ratio of 1:16, 1:64, 1:256, or 1:4096, for 1 hour at 37° C. 34 human samples were tested. The mixture was added to the culture plate with Hela S3 cells and incubated for 3 days. At the same time, control samples were set up in parallel. After 72 hours of incubation, cells were harvested and analyzed by flow cytometry.

AAV-DJ at a MOI (multiplicity of infection) $10^4$ was tested using diluted human sera at a ratio of 1:16, 1:64, 1:256, or 1:4096.

TABLE 43

AAV DJ neutralizing assay in human serum samples (MOI $10^4$) ($2^{nd}$ cohort)

| Dilution | Samples (data given as %) | | | | | | | | |
|---|---|---|---|---|---|---|---|---|---|
| | #1 | #2 | #3 | #4 | #5 | #6 | #7 | #8 | #9 |
| 1:16 | 7.2 | 6.1 | 5.3 | 0.8 | 0.2 | 7.7 | 6.3 | 6.2 | 1.0 |
| 1:64 | 38.9 | 32.4 | 24.4 | 33.2 | 0.1 | 38.5 | 29.1 | 32.5 | 0.1 |
| 1:256 | 69.2 | 65.9 | 59.0 | 62.4 | 0.4 | 67.6 | 62.4 | 61.0 | 0.9 |
| 1:4096 | 75.1 | 74.9 | 73.4 | 73.8 | 55.7 | 76.2 | 74.8 | 73.0 | 50.6 |
| | #10 | #11 | #12 | #13 | #14 | #15 | #16 | #17 | #18 |
| 1:16 | 7.2 | 0.4 | 5.7 | 10.9 | 12.6 | 20.2 | 7.6 | 13.0 | 3.7 |
| 1:64 | 35.0 | 0.1 | 32.9 | 33.9 | 41.3 | 50.4 | 35.1 | 38.0 | 15.9 |
| 1:256 | 66.2 | 0.2 | 60.3 | 60.2 | 63.3 | 67.2 | 62.5 | 63.6 | 41.3 |
| 1:4096 | 59.4 | 22.6 | 61.6 | 60.6 | 61.9 | 60.6 | 59.9 | 59.1 | 43.6 |
| | #19 | #20 | #21 | #22 | #23 | #24 | #25 | #26 | #27 |
| 1:16 | 0.2 | 0.3 | 0.4 | 1.8 | 3.9 | 39.3 | 35.7 | 0.8 | 51.2 |
| 1:64 | 0.2 | 0.2 | 0.2 | 45.4 | 50.6 | 37.0 | 39.1 | 8.8 | 39.3 |
| 1:256 | 0.6 | 1.0 | 0.7 | 65.7 | 68.6 | 56.7 | 70.6 | 28.4 | 48.8 |
| 1:4096 | 53.1 | 62.4 | 45.3 | 69.2 | 61.5 | 56.3 | 76.2 | 74.2 | 62.8 |
| | #28 | #29 | #30 | #31 | #32 | #33 | #34 | control | control |
| 1:16 | 6.6 | 24.2 | 16.1 | 33.2 | 44.5 | 44.1 | 23.4 | 77.8 | 65.5 |
| 1:64 | 21.7 | 53.7 | 65.7 | 27.9 | 43.4 | 44.1 | 49.1 | 68.4 | 59.1 |
| 1:256 | 55.5 | 71.3 | 60.5 | 51.0 | 55.2 | 62.7 | 68.9 | 77.8 | 62.2 |
| 1:4096 | 58.9 | 63.4 | 63.0 | 64.2 | 56.2 | 62.1 | 64.4 | 56.6 | 45.5 |

AAV1 at MOI (multiplicity of infection) $10^5$ was pre-incubated with diluted human sera at a ratio of 1:16, 1:64, 1:256, or 1:4096, for 1 hour at 37° C. The mixture was added to the culture plate with Hela S3 cells and incubated for 3 days. At the same time, control samples were set up in parallel. After 72 hours of incubation, cells were harvested and analyzed by flow cytometry. The cut-off for analysis is at 10%.

AAVrh10 at MOI (multiplicity of infection) $10^4$ was pre-incubated with diluted human sera at a ratio of 1:16, 1:64, 1:256, or 1:4096, for 1 hour at 37° C. The mixture was added to the culture plate with Hela S3 cells and incubated for 3 days. At the same time, control samples were set up in parallel. After 72 hours of incubation, cells were harvested and analyzed by flow cytometry. The cut-off for analysis is at 7.5%.

TABLE 44

AAV1 neutralizing assay in human serum samples (MOI $10^5$) ($2^{nd}$ cohort)

| Dilution | Samples (data given as %) | | | | | | | | |
|---|---|---|---|---|---|---|---|---|---|
| | #1 | #2 | #3 | #4 | #5 | #6 | #7 | #8 | #9 |
| 1:16 | 20.7 | 18.2 | 22.6 | 1.5 | 0.3 | 12.3 | 19.3 | 18.2 | 0.5 |
| 1:64 | 23.3 | 22.0 | 20.5 | 13.8 | 0.4 | 19.2 | 20.5 | 20.2 | 0.5 |
| 1:256 | 23.6 | 21.4 | 21.5 | 19.6 | 0.9 | 21.0 | 18.4 | 22.3 | 0.8 |
| 1:4096 | 22.5 | 22.4 | 20.1 | 23.7 | 9.4 | 21.7 | 24.8 | 21.9 | 9.1 |
| | #10 | #11 | #12 | #13 | #14 | #15 | #16 | #17 | #18 |
| 1:16 | 24.6 | 0.1 | 27.6 | 27.0 | 21.8 | 16.6 | 14.6 | 21.7 | 16.1 |
| 1:64 | 22.4 | 0.2 | 24.3 | 25.1 | 22.9 | 17.4 | 19.5 | 19.1 | 17.6 |
| 1:256 | 20.5 | 0.3 | 19.7 | 19.8 | 22.8 | 20.7 | 19.8 | 19.3 | 18.8 |
| 1:4096 | 22.1 | 3.2 | 21.9 | 25.5 | 21.7 | 22.2 | 23.5 | 21.8 | 23.2 |
| | #19 | #20 | #21 | #22 | #23 | #24 | #25 | #26 | #27 |
| 1:16 | 0.2 | 0.2 | 0.4 | 2.6 | 1.2 | 3.7 | 21.4 | 0.9 | 15.0 |
| 1:64 | 0.1 | 0.1 | 0.1 | 15.1 | 12.6 | 13.1 | 20.8 | 0.3 | 20.6 |
| 1:256 | 0.1 | 0.3 | 0.1 | 19.8 | 19.2 | 19.1 | 20.3 | 5.5 | 18.6 |
| 1:4096 | 7.7 | 9.0 | 1.3 | 21.1 | 20.7 | 22.7 | 22.2 | 21.5 | 21.7 |
| | #28 | #29 | #30 | #31 | #32 | #33 | #34 | control | control |
| 1:16 | 20.1 | 10.4 | 3.1 | 6.3 | 21.4 | 20.2 | 19.1 | 24.0 | 24.7 |
| 1:64 | 20.4 | 20.5 | 13.4 | 5.7 | 23.1 | 23.6 | 19.9 | 22.8 | 25.3 |
| 1:256 | 19.3 | 19.3 | 18.3 | 4.8 | 21.0 | 21.3 | 20.4 | 20.9 | 22.4 |
| 1:4096 | 23.5 | 24.3 | 23.7 | 22.5 | 21.6 | 23.6 | 23.2 | 23.9 | 24.4 |

TABLE 45

AAVrh10 neutralizing assay in human serum samples (MOI $10^5$) ($2^{nd}$ cohort)

| Dilution | Samples (data given as %) | | | | | | | | |
|---|---|---|---|---|---|---|---|---|---|
| | #1 | #2 | #3 | #4 | #5 | #6 | #7 | #8 | #9 |
| 1:16 | 11.0 | 10.9 | 10.8 | 8.7 | 0.3 | 5.9 | 9.7 | 9.9 | 0.5 |
| 1:64 | 8.2 | 12.9 | 12.3 | 10.5 | 5.1 | 7.5 | 12.9 | 11.5 | 5.4 |
| 1:256 | 10.2 | 12.5 | 11.7 | 10.2 | 8.2 | 6.6 | 12.2 | 11.1 | 10.1 |
| 1:4096 | 9.0 | 14.3 | 12.1 | 10.8 | 10.6 | 15.7 | 14.2 | 11.8 | 11.5 |
| | #10 | #11 | #12 | #13 | #14 | #15 | #16 | #17 | #18 |
| 1:16 | 13.7 | 0.4 | 11.7 | 12.2 | 8.0 | 12.8 | 10.5 | 9.7 | 10.7 |
| 1:64 | 16.0 | 6.0 | 11.4 | 10.5 | 9.4 | 14.2 | 12.1 | 10.2 | 10.4 |
| 1:256 | 18.1 | 9.1 | 11.7 | 9.6 | 9.8 | 12.7 | 10.6 | 9.4 | 10.9 |
| 1:4096 | 16.1 | 12.3 | 12.3 | 11.5 | 11.2 | 13.5 | 12.7 | 11.4 | 11.5 |
| | #19 | #20 | #21 | #22 | #23 | #24 | #25 | #26 | #27 |
| 1:16 | 0.6 | 0.5 | 0.2 | 8.0 | 9.1 | 8.4 | 9.4 | 6.4 | 8.4 |
| 1:64 | 6.8 | 5.7 | 2.3 | 9.4 | 9.7 | 10.1 | 10.2 | 8.5 | 10.0 |
| 1:256 | 8.5 | 11.2 | 7.5 | 10.7 | 10.4 | 9.5 | 11.4 | 9.3 | 10.4 |
| 1:4096 | 10.2 | 12.4 | 11.9 | 11.5 | 11.0 | 10.7 | 11.6 | 10.6 | 9.6 |
| | #28 | #29 | #30 | #31 | #32 | #33 | #34 | control | control |
| 1:16 | 8.4 | 10.4 | 11.4 | 7.2 | 9.6 | 10.1 | 11.1 | 11.5 | 12.0 |
| 1:64 | 10.0 | 11.2 | 11.6 | 11.2 | 11.3 | 11.1 | 11.7 | 11.8 | 11.8 |
| 1:256 | 9.9 | 13.2 | 11.2 | 12.0 | 10.4 | 12.5 | 12.0 | 12.3 | 11.2 |
| 1:4096 | 12.8 | 13.0 | 12.0 | 11.4 | 12.4 | 13.4 | 11.3 | 11.4 | 11.5 |

Similar to the result obtained from the first test cohort, stronger neutralizers (individuals) have titers that are capable of neutralization across AAV serotypes.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

We claim:

1. A method of determining the titer of adeno-associated virus (AAV) neutralizing antibodies in a human serum sample, said method comprising:
   (a) incubating a recombinant AAV vector comprising a heterologous sequence with a human serum sample to form a serum/vector mixture;
   (b) exposing AAV permissive cells to the serum/vector mixture to produce AAV transduced cells which have been transduced with the recombinant AAV vectors from the serum/vector mixture;
   (c) measuring the quantity of the AAV transduced cells; and
   (d) determining the AAV neutralizing antibody titer in the serum sample based on the measured quantity of the AAV transduced cells;
   wherein the serum sample is collected from a patient in need of an AAV mediated gene therapy, a patient after a dose of AAV gene therapy, or a patient suspected of exposure to an AAV vector.

2. The method of claim 1, wherein the recombinant AAV vector comprises a GFP tag.

3. The method of claim 2, wherein the AAV permissive cells are selected from Huh7 cells, human cancer cell line HeLa cells, HeLa S3 cells, murine hepatoma Hepal-6 cells, HEK293, human hepatoma cells HepG2 and IMY-N9.

4. The method of claim 2, wherein the AAV permissive cells are HeLa S3 cells.

5. The method of claim 2, wherein the AAV transduced cells are measured for GFP signal using flow cytometry to identify GFP-positive AAV transduced cells.

6. The method of claim 5, wherein the GFP-positive AAV transduced cells are evaluated to determine the AAV neutralizing antibody titers in the serum sample.

7. The method of claim 1, wherein the step of exposing the AAV permissive cells to the serum/vector mixture does not include an adenovirus or another helper virus to facilitate transduction.

8. A method of determining the titer of adeno-associated virus (AAV) neutralizing antibodies in a human serum sample, said method comprising
   (a) incubating an AAV vector with a human serum sample to form a serum/vector mixture;
   (b) exposing AAV permissive whole cells to the serum/vector mixture to produce AAV transduced cells which have been transduced with the AAV vectors from the serum/vector mixture;
   (c) measuring the quantity of whole cells transduced by AAV; and
   (d) determining the AAV neutralizing antibody titer in the serum sample based on the measured quantity of the AAV transduced whole cells.

9. The method of claim 8, wherein the AAV vector comprises a GFP tag.

10. The method of claim 9, wherein the AAV permissive whole cells are selected from Huh7 cells, human cancer cell line HeLa cells, HeLa S3 cells, murine hepatoma Hepal-6 cells, HEK293, human hepatoma cells HepG2 and IMY-N9.

11. The method of claim 9, wherein the AAV permissive whole cells are HeLa S3 cells.

12. The method of claim 9, wherein the AAV transduced cells are measured for GFP signal using flow cytometry to identify GFP-positive AAV transduced cells.

13. The method of claim 12, wherein the GFP-positive AAV transduced cells are evaluated to determine the AAV neutralizing antibody titers in the serum sample.

14. The method of claim 12, wherein the GFP positive AAV transduced cells are evaluated as whole cells to determine the AAV neutralizing antibody titers in the serum sample.

15. The method of claim 13, wherein the serum sample is collected from a patient in need of an AAV mediated gene therapy, a patient after a dose of AAV gene therapy, or a subject suspected of exposure to AAV.

16. A method of determining the titer of adeno-associated virus (AAV) neutralizing antibodies in a human cerebrospinal fluid (CSF) sample, said method comprising
    (a) incubating an AAV vector with a human cerebrospinal fluid (CSF) sample to form a CSF/vector mixture;
    (b) exposing AAV permissive cells to the CSF/vector mixture to produce AAV transduced cells which have been transduced with the AAV vectors from the CSF/vector mixture;
    (c) measuring the quantity of the AAV transduced cells; and
    (d) determining the AAV neutralizing antibody titer in the CSF sample based on the measured quantity of the AAV transduced cells.

17. The method of claim 16, wherein the AAV vector comprises a GFP tag.

18. The method of claim 17, wherein the AAV permissive whole cells are HeLa S3 cells.

19. The method of claim 18, wherein the AAV transduced cells are measured for GFP signal using flow cytometry to identify GFP-positive AAV transduced cells.

20. The method of claim 19, wherein the CSF sample is collected from a patient in need of an AAV mediated gene therapy, a patient after a dose of AAV gene therapy, or a subject suspected of exposure to AAV.

21. The method of claim 16, wherein the AAV vector is a recombinant AAV vector comprising a heterologous sequence.

22. The method of claim 8, wherein the AAV vector is a recombinant AAV vector comprising a heterologous sequence.

* * * * *